(12) United States Patent
Tsantrizos et al.

(10) Patent No.: US 8,816,082 B2
(45) Date of Patent: Aug. 26, 2014

(54) HETEROCYCLYL-PYRIDINYL-BASED BIPHOSPHONIC ACID, PHARMACEUTICALLY ACCEPTABLE SALT THEREOF, COMPOSITION THEREOF AND METHOD OF USE THEREOF

(75) Inventors: Youla S. Tsantrizos, Montreal (CA); Joris Wim De Schutter, Montreal (CA); Yih-Shyan Lin, Montreal (CA)

(73) Assignee: The Royal Institution for the Advancement of Learning/McGill University, Montreal, Quebec (CA)

( * ) Notice: Subject to any disclaimer, the term of this patent is extended or adjusted under 35 U.S.C. 154(b) by 0 days.

(21) Appl. No.: 13/700,192

(22) PCT Filed: May 27, 2011

(86) PCT No.: PCT/CA2011/050322
§ 371 (c)(1),
(2), (4) Date: Jan. 29, 2013

(87) PCT Pub. No.: WO2011/147038
PCT Pub. Date: Dec. 1, 2011

(65) Prior Publication Data
US 2013/0203702 A1    Aug. 8, 2013

Related U.S. Application Data

(60) Provisional application No. 61/349,442, filed on May 28, 2010, provisional application No. 61/487,323, filed on May 18, 2011.

(51) Int. Cl.
| | | |
|---|---|---|
| C07F 9/6558 | (2006.01) | |
| A61K 31/675 | (2006.01) | |
| A61P 19/10 | (2006.01) | |
| A61P 3/06 | (2006.01) | |
| A61P 31/12 | (2006.01) | |
| A61P 35/00 | (2006.01) | |
| C07F 9/58 | (2006.01) | |

(52) U.S. Cl.
USPC ............. 546/22; 546/232; 546/243; 546/337; 514/89; 514/85; 514/86; 514/87

(58) Field of Classification Search
USPC ................................................ 514/89; 546/22
See application file for complete search history.

(56) References Cited

U.S. PATENT DOCUMENTS

2008/0255070 A1*  10/2008  Oldfield et al. ................. 514/89
2009/0143337 A1    6/2009  Weiler et al.

FOREIGN PATENT DOCUMENTS

| WO | 9324497 | 12/1993 |
|---|---|---|
| WO | 9324499 | 12/1993 |

(Continued)

OTHER PUBLICATIONS

Wolff, Manfred E. "Burger's Medicinal Chemistry, 5ed, Part I", John Wiley & Sons, 1995, pp. 975-977.*

(Continued)

*Primary Examiner* — John Mabry
*Assistant Examiner* — Daniel Carcanague
(74) *Attorney, Agent, or Firm* — Norton Rose Fulbright Canada LLP

(57) ABSTRACT

The present invention relates to novel compounds, compositions containing same and methods for inhibiting human farnesyl pyrophosphate synthase or for the treatment or prevention of disease conditions using said compounds;

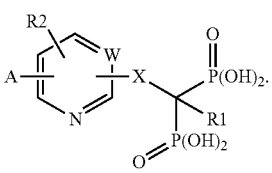

13 Claims, 1 Drawing Sheet

(56) References Cited

FOREIGN PATENT DOCUMENTS

| WO | 9631124 | 10/1996 |
|---|---|---|
| WO | 9743437 | 11/1997 |
| WO | 2005002590 | 1/2005 |
| WO | 2008075165 | 6/2008 |
| WO | 2008076417 | 6/2008 |
| WO | 2008128056 | 10/2008 |
| WO | 2010033978 | 3/2010 |
| WO | 2010033980 | 3/2010 |
| WO | 2010033981 | 3/2010 |
| WO | 2011147038 | 12/2011 |

OTHER PUBLICATIONS

Banker, G.S. et al, "Modern Pharmaceutics, 3ed.", Marcel Dekker, New York, 1996, pp. 451 and 596.*
Dorwald; "Side Reactions in Organic Synthesis: A Guide to Successful Synthesis Design" 2005 Wiley-VCH Verlag GmbH & Co. KGaA, Wienheim, Chapter 1.*
Chen; J. Med. Chem. 2008, 51, 5594-5607.*
Song; Bioorganic & Medicinal Chemistry 16 (2008) 8959-8967.*
Silverman; The Organic Chemistry of Drug Design and Drug Action, Second Edition, 2004, Elsevier, pp. 29-34.*
Wermuth; "Analogue-based Drug Discovery", 2006, Wiley, pp. 3-23.*
Breccia, R et al. "Thiopyrophosphoantigens: Solid-phase Synthesis and in Vitro Characterization of a New Class of Vγ9 Vδ2 T Cells Activators". J. Med. Chem. vol. 52, 2009. pp. 3716-3722.
Caraglia, M. et al. "Emerging anti-cancer molecular mechanisms of aminobisphosphonates". Endocrine-Related Cancer. vol. 13. 2006. pp. 7-26.
Coleman, R.E. "Adjuvant bisphosphonates in breast cancer: Are we witnessing the emergence of a new therapeutic strategy?". Eur. J. Cancer. vol. 45. 2009. pp. 1909-1915.
Corbet, J.P. & Mignani, G. "Selected Pateneted Cross-Coupling Reaction Technologies". Chem. Rev. vol. 106. 2006. pp. 2651-2710.
De Schutter et al. "Novel Bisphosphonate Inhibitors of the Human Farnesyl Pyrophosphate Synthase". Bio. Med. Chem. Letters. vol. 20. 2010. pp. 5781-5786.
Dunford, J.E. et al. "Structure-Activity Relationships for Inhibition of Farnesyl Diphosphate Synthase in Vitro and Inhibition of Bone Resorption in Vivo by Nitrogen-Containing Bisphosphonates." J. Pharmacol. Exp. Ther. vol. 296. 2001. pp. 235-242.
Dunford, J.E. et al. "Structure-Activity Relationships Among the Nitrogen Containing Bisphosphonates in Clinical Use and Other Analogues: Time-Dependent Inhibition of Human Farnesyl Pyrophosphate Synthase". J. Med. Chem. vol. 51. 2008. pp. 2187-2195.
Ellis, C.A. et al. "Rig is a novel Ras-related protein and potential neural tumor suppressor". PNAS. vol. 99, No. 15. pp. 9876-9881, 2002.
Forlani, G. et al. "Plant P5C Reductase as a New Target for Aminomethylenebisphospohnates". J. Agric. Food Chem. 2007. vol. 55. pp. 4340-4347.
Laggner, U. et al. "Regression of melanoma metastases following treatment with the n-bisphosphonate zoledronate and localised radiotherapy". Clin. Immunol. vol. 131. 2009. pp. 367-373.
Leon, A. et al. "Isoprenoid Biosynthesis as a Drug Target: Bisphosphonate Inhibition of *Escherichia coli* K12 Growth and Synergistic Effects of Fosmidomycin". J. Med. Chem. vol. 49. 2006. pp. 7331-7341.
Li, J. et al. "Reduced Expression of the Mevalonate Pathway Enzyme Farnesyl Pyrophosphate Synthase Unveils Recognition of Tumor Cells by V γ9Vδ2 T Cells". J. Immunol. vol. 182. 2009. pp. 8118-8124.
Marma, M.S. et al. "Synthesis and Biological Evaluation of r-Halogenated Bisphosphonate and Phosphonocarboxylate Analogues of Risedronate". J. Med. Chem. vol. 50. 2007. pp. 5967-5975.
Martin, M.B. et al. "Activity of Bisphosphonates against *Trypanosoma brucei* rhodesiense". J. Med. Chem. Vo. 45. 2002. pp. 2904-2914.
Matczak-Jon E. et al. "Specificity of the Zinc(II), Magnesium(II) and Calcium(II) Complexation by (pyridine-2-yl) aminomethane-1,1-diphosphonic acids and related 1,3-(thiazol-2-yl) and 1,3-(benzothiazol-2-yl) derivatives". Dalton Transaction. vol. 39. 2010. pp. 1207-1221.
Morita, C.T. et al. "Nonpeptide antigens, presentation mechanisms, and immunological memory of human Vg2Vd2 T cells: discriminating friend from foe through the recognition of prenyl pyrophosphate antigens". Immunological Reviews. vol. 215. 2007. pp. 59-76.
Nguyen U.T.T. et al. "Analysis of the eukaryotic prenylome by isoprenoid affinity tagging". Nat. Chem. Biol. vol. 5, No. 4. 2009. pp. 227-235.
Notarnicola, M. et al. "Higher Farnesyl Diphosphate Synthase Activity in Human Colorectal Cancer Inhibition of Cellular Apoptosis". Oncology. vol. 67. 2004. pp. 351-358.
Sanders, J.M. et al. "3-D QSAR Investigations of the Inhibition of Leishmania Major Farnesyl Pyrophosphate Synthase by Bisphosphonates". J. Med. Chem. 2003. 46, (pp. 5171-5183).
Sanders, J.M. et al. "Quantitative Structure—Activity Relationships for γδ T Cell Activation by Bisphosphonates". J. Med. Chem. 2004. 47, (pp. 375-384).
Schroeder, G. et al. "Mass Spectrometric and PM5 Study of N-(2-pyridyl)-aminomethyldiphoshonic Acids and their Complexes with Alkali Cations". J. Mol. Str. 2005. 750, (pp. 142-151).
Walsh C.T. et al. "Protein Posttranslational Modifications: The Chemistry of Proteome Diversifications". Angew. Chem. Int. Ed. vol. 44. 2005. pp. 7342-7372.
Zhang Y. et al. "Activity of Nitrogen-Containing and Non-Nitrogen-Containing Bisphosphonates on Tumor Cell Lines". J. Med. Chem. vol. 49. 2006. pp. 5804-5814.
Zhang Y. et al. "Activity of Sulfonium Bisphosphonates on Tumor Cell Lines". J. Med. Chem. vol. 50. 2007. pp. 6067-6079.
Zhang Y. et al. "Lipophilic Bisphosphonates as Dual Farnesyl/Geranylgeranyl Diphosphate Synthase Inhibitors: An X-ray and NMR Investigation". J. Am. Chem. Soc. vol. 131. 2009. pp. 5153-5162.
Tsantrizos, Y.S. "Inhibitors of human Farnesyl Pyrophosphate Synthase" (#10114). Presentation at The Crossroad for BioTransfer. May 19, 2011. pp. 1-12.
Tsantrizos, Y.S. et al. "Novel Inhibitors of Human Farnesyl Pyrophosphate Synthase; in Silico Design, Synthesis and Biological Evaluation", Presentation at the 93rd Canadian Chemistry Conference and Exhibition May 30, 2010. pp. 1-23.

* cited by examiner

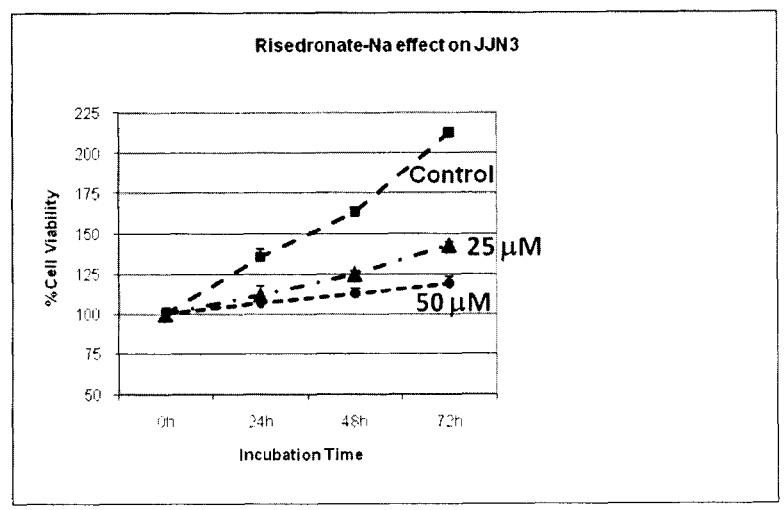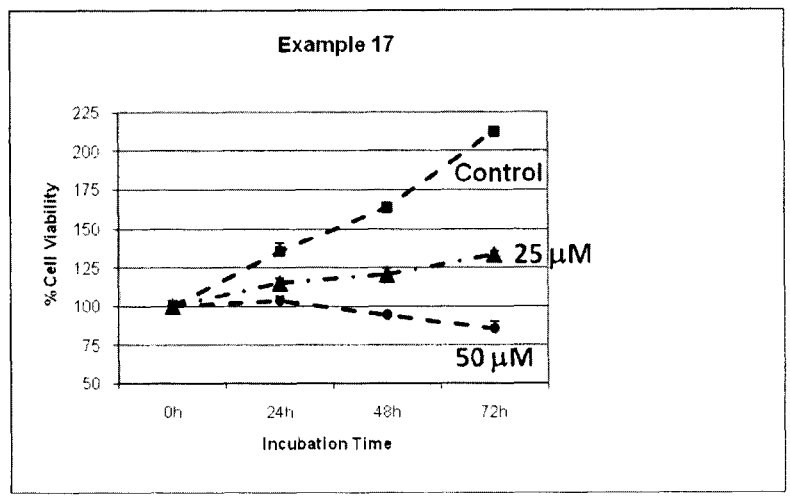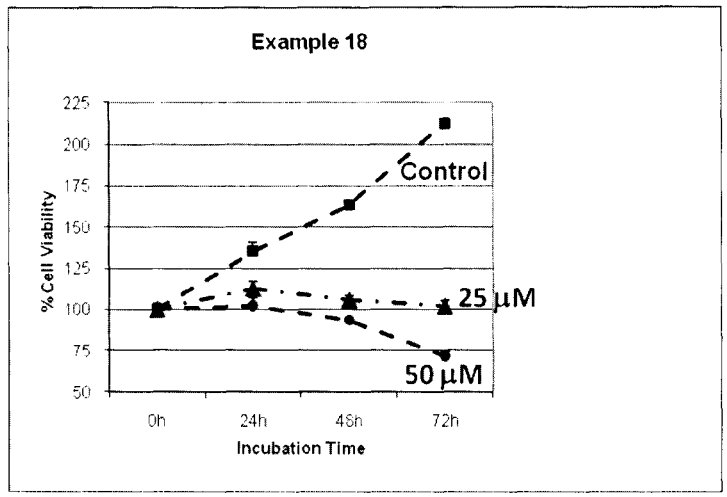

HETEROCYCLYL-PYRIDINYL-BASED BIPHOSPHONIC ACID, PHARMACEUTICALLY ACCEPTABLE SALT THEREOF, COMPOSITION THEREOF AND METHOD OF USE THEREOF

CROSS-REFERENCE TO RELATED APPLICATIONS

This application is the 371 national phase entry of PCT/CA2011/050322 filed May 27, 2011, the content of which is hereby incorporated in its entirety. The present application also claims priority on U.S. Provisional Application No. 61/349,442, filed May 28, 2010, and U.S. Provisional Application No. 61/487,323, filed on May 18, 2011, which are incorporated herein by reference.

FIELD OF THE DISCLOSURE

The present invention relates to novel compounds, compositions containing same and methods for inhibiting human farnesyl pyrophosphate synthase or for the treatment or prevention of disease conditions using said compounds.

BACKGROUND OF THE DISCLOSURE

The human farnesyl pyrophosphate synthase (hFPPS) enzyme is responsible for the catalytic elongation of dimethylallyl pyrophosphate (DMAPP) to geranyl pyrophosphate (GPP) and then to farnesyl pyrophosphate (FPP) via the successive condensation of two isopentenyl pyrophosphate IPP units (Scheme 1).

Furthermore, farnesyl pyrophosphate (FPP) is the key metabolic precursor for the biosynthesis of geranylgeranyl pyrophosphate (GGPP), which is catalyzed by geranylgeranyl pyrophosphate synthase (GGPPS). Consequently, inhibition of FPPS would result in decreased levels of both FPP and GGPP in a mammalian host, including a human host. Post-translational prenylation with FPP or GGPP of conserved cysteine residues at (or near) the C-termini of over 300 known human proteins plays a crucial for their biological activity.

Rap, is also required in order to regulate the proliferation, invasive properties, and pro-angiogenic activity in human cancers (see Caraglia, M. et al. *Endocrine-Related Cancer* 2006, 13, 7-26 and Zhang, Y. et al. *J. Am. Chem. Soc.* 2009, 131, 5153-5162).

The role of hFPPS in protein prenylation in osteoclasts is known (see for example Dunford, J. E. et al. *J. Pharmacol. Exp. Ther.* 2001, 296, 235-242; Marma, M. S. et al. *J. Med. Chem.* 2007, 50, 5967-5975. Dunford, J. E. et al. *J. Med. Chem.* 2008, 51, 2187-2195) and nitrogen-containing bisphosphonate (N-BP) inhibitors of hFPPS are commonly used in the treatment of osteoporosis, tumor-induced hypercalcemia, Paget's disease and osteolytic metastases (see Caraglia, M. et al, supra).

Inhibitors of hFPPS have also been reported to stimulate the immune system by indirectly activating Vγ2Vδ2 T cells (also known as Vγ9Vδ2 T cells), thus mediating antitumor and antimicrobial effects, more specifically broad-spectrum antiviral and antibacterial effects (see for example Sanders, J. M. et al. *J. Med. Chem.* 2004, 47, 375-384; Zhang, Y. et al. *J. Med. Chem.* 2007, 50, 6067-6079; Morita, C. T. et al. *Immunological Reviews* 2007, 215, 59-76; Breccia, P. et al. *J. Med. Chem.* 2009, 52, 3716-3722 and Li, J. et al. *J. Immunol.* 2009, 182, 8118-8124. Evidence for the stimulation of Vγ2Vδ2-bearing T cells by N-BPs has been observed in multiple myeloma (MM) patients (Kunzmann, V.; Bauer, E.; Wilhelm, M. *New Engl. J. Med.* 1999, 340, 737) and prostate cancer patients (Naoe, M.; Ogawa, Y.; Takeshita, K.; Morita, J.; Shichijo, T.; Fuji, K.; Fukagai, T.; Iwamoto, S.; Terao, S. *Oncology, Res.* 2010, 18, 493) treated with N-BPs. The antitumor effects of bisphosphonates inhibiting hFPPS (and/or its related enzyme hGGPPS) have been implicated in a variety of cancers (see Caraglia, M. et al, supra), including colorectal (see Notarnicola, M. et al. *Oncology* 2004, 67, 351-358), prostate, melanoma (see Laggner, U. et al. *Clin. Immunol.* 2009, 131, 367-373), breast (see for example Coleman, R. E. *Eur. J. Cancer* 2009, 45, 1909-1915), ovarian, and brain (see Ellis, C. A. et al. *Proc. Natl. Acad. Sci. USA* 2002, 99, 9876-9881) cancers.

Scheme 1: Pathway of human farnesyl pyrophosphate

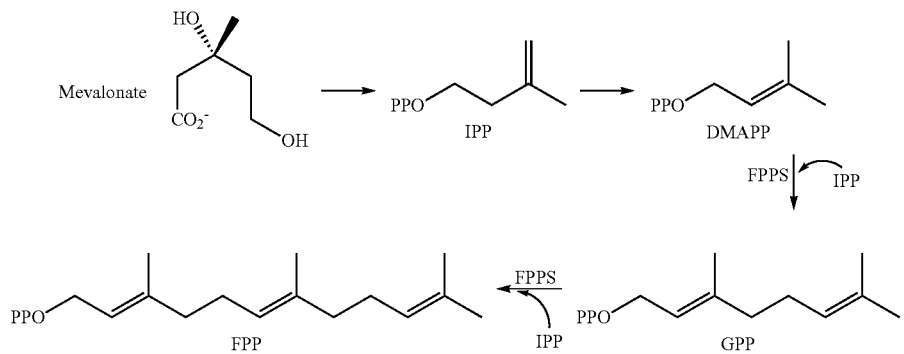

The farnesylation or geranylgeranylarion of proteins confers membrane localization, promotes specific protein-protein interactions and is believed to play a critical role in intracellular trafficking and signal transduction (see for example Nguyen U. T. T. et al. *Nat. Chem. Biol.* 2009, 5, 227-235 and Walsh C. T. et al. *Angew. Chem. Int. Ed.* 2005, 44, 7342-7372). Addition of the FPP or GGPP lipidic moiety to the GTP-binding proteins, including Ras, Rho, Rac and In addition, current literature strongly suggests that the prenylation pathway leading from FPP to the prenylation of the small GTPase protein RhoA-cdc42, leads to accumulation of the phospho-Tau protein in the human brain, which is implicated in neuronal damage and the progression of Alzheimer's disease (AD) (see Eckert, G. P. et al. *Neurobiol. Disease* 2009, 35, 252; Hooff, G. P. et al. *Biochim. Biophys. Acta* 2010, 1801, 896; Chauhan, N. B. *J. Ethnopharmacol.* 2006, 108, 385; Ohm, T. G. et al. *Pharmacopsychiatry* 2003b, 36 Suppl 2, S120; Sayas. C. L. et al. *J. Biol. Chem.* 1999, 274, 37046.)

Bisphosphonates of this disclosure that target the human FPPS may also be used for lowering cholesterol. However, such compounds may also be capable of inhibiting the FPPS enzymes of microorganisms and protozoan parasites, such as the groups of *Leishmania, Plasmodium, Trypanosoma, Toxoplasma, Cryptosporidium*.

SUMMARY

In an aspect of the disclosure, there is provided a compound of formula I

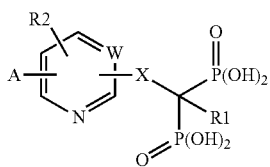

or a pharmaceutically acceptable salt, solvate or prodrug thereof, wherein

A is an halogen, or an optionally substituted 3-11 membered heterocycle or an optionally substituted C6-10 aryl;

W is CH or N;

X is each independently CR10R11 or NR10;

R1 is H, OH, or F;

R2 is hydrogen, or one or more substituent each independently selected from halogen, amino, amidino, amido, azido, cyano, guanido, hydroxyl, nitro, nitroso, urea, —OS(O)$_2$R20, —OS(O)$_2$OR21, —S(O)$_2$OR21, S(O)$_{0-2}$R21, —OP(O)OR22OR23, —P(O)OR22OR23, C1-6alkyl, C6-10aryl-C1-6alkyl, optionally substituted C6-10aryl, C1-6alkoxy, C6-10aryl-C1-6alkyloxy, C6-10aryloxy, optionally substituted 3-10 membered heterocycle, —C(O)R24, —C(O)OR24, —NR25C(O)R26 and —SO$_2$NR24R27;

R10 and R11 are each independently H or C1-6 alkyl;

R20 is each independently C1-6 alkyl, C6-10 aryl or 3-10 membered heterocycle;

R21 is each independently H, C1-6 alkyl, C6-10 aryl or 3-10 membered heterocycle;

R22 and R23 are each independently H or C1-6 alkyl;

R24 and R27 are each independently H, C1-6 alkyl, C6-10 aryl, C6-10aryl-C1-6alkyl or 3-10 membered heterocycle;

R25 is H or C1-6 alkyl; and

R26 is each independently H, C1-6 alkyl, C6-10 aryl, C6-10aryl-C1-6alkyl or 3-10 membered heterocycle;

or R25 and R26 are taken together with the atoms to which they are attached to form a 3 to 10 membered heterocycle.

In another aspect of the disclosure, there is provided a pharmaceutical composition comprising a compound as defined herein or a pharmaceutically acceptable salt, solvate or prodrug thereof, and an acceptable excipient.

In another aspect of the disclosure, there is provided a method for inhibiting human farnesyl pyrophosphate synthase, comprising administering a therapeutically effective amount of a compound as defined herein or a pharmaceutically acceptable salt, solvate or prodrug thereof, to a patient.

In yet another aspect of the disclosure, there is provided a method for treating or preventing osteoporosis, viral infection, cancer or lowering of cholesterol, comprising administering a therapeutically effective amount of a compound as defined herein, or a pharmaceutically acceptable salt, solvate or prodrug thereof, to a patient.

In another aspect of the disclosure, there is provided the use of a compound as defined herein or a pharmaceutically acceptable salt, solvate or prodrug thereof, in the manufacture of a medicament for inhibiting human farnesyl pyrophosphate synthase.

In another aspect of the disclosure, there is provided the use of a compound as defined herein or a pharmaceutically acceptable salt, solvate or prodrug thereof, in the manufacture of a medicament for treating or preventing osteoporosis, viral infection, cancer, or lowering of cholesterol.

In yet another aspect of the disclosure, there is provided the use of a compound as defined herein or a pharmaceutically acceptable salt, solvate or prodrug thereof, for inhibiting human farnesyl pyrophosphate synthase.

In another aspect of the disclosure, there is provided the use of a compound as defined herein or a pharmaceutically acceptable salt, solvate or prodrug thereof, for treating or preventing osteoporosis, viral infection, cancer or lowering of cholesterol.

In another aspect of the disclosure, there is provided a pharmaceutical composition as defined herein for use in inhibiting human farnesyl pyrophosphate synthase.

In yet another aspect of the disclosure, there is provided a pharmaceutical composition as defined herein for use in treating or preventing osteoporosis, viral infection, cancer or lowering of cholesterol.

In one aspect, there is provided a process for preparing a compound of formula I as defined herein.

BRIEF DESCRIPTION OF THE DRAWINGS

FIG. 1 is graphs illustrating the anti-proliferation effects in multiple myeloma JJN3 cells of Risedronate-Na, compounds 17 and 18.

DESCRIPTION OF THE EMBODIMENTS

In accordance with one embodiment, the disclosure provides a compound of formula I

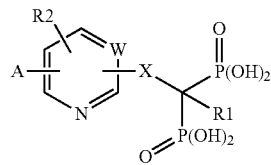

or a pharmaceutically acceptable salt, solvate or prodrug thereof, wherein

A is a halogen, or an optionally substituted 3-11 membered heterocycle or an optionally substituted C6-10 aryl;

W is CH or N;

X is each independently CR10R11 or NR10;

R1 is H, OH, or F;

R2 is hydrogen, or one or more substituent each independently selected from halogen, amino, amidino, amido, azido, cyano, guanido, hydroxyl, nitro, nitroso, urea, —OS(O)$_2$R20, —OS(O)$_2$OR21, —S(O)$_2$OR21, S(O)$_{0-2}$R21, —OP(O)OR22OR23, —P(O)OR22OR23, C1-6alkyl, C6-10aryl-C1-6alkyl, optionally substituted C6-10aryl, C1-6alkoxy, C6-10aryl-C1-6alkyloxy. C6-10aryloxy, optionally substituted 3-10 membered heterocycle, —C(O)R24, —C(O)OR24, —NR25C(O)R26 and —SO₂NR24R27;

R10 and R11 are each independently H or C1-6 alkyl;

R20 is each independently C1-6 alkyl, C6-10 aryl or 3-10 membered heterocycle;

R21 is each independently H, C1-6 alkyl, C6-10 aryl or 3-10 membered heterocycle;

R22 and R23 are each independently H or C1-6 alkyl;

R24 and R27 are each independently H, C1-6 alkyl, C6-10 aryl, C6-10aryl-C1-6alkyl or 3-10 membered heterocycle;

R25 is H or C1-6 alkyl; and

R26 is each independently H, C1-6 alkyl, C6-10 aryl, C6-10aryl-C1-6alkyl or 3-10 membered heterocycle.

or R25 and R26 are taken together with the atoms to which they are attached to form a 3 to 10 membered heterocycle.

In accordance with one embodiment, the disclosure provides a compound of formula I:

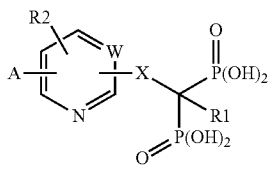

I or a pharmaceutically acceptable salt or solvate thereof, wherein

A is an optionally substituted 3-11 membered heterocycle or an optionally substituted C6-10 aryl;

W is CH or N;

X is CR10R11 or NR10;

R1 is H, OH, or F;

R2 is one or more substituents, each independently selected from halogen, amino, amidino, amido, azido, cyano, guanido, hydroxyl, nitro, nitroso, urea, —OS(O)₂R20, —OS(O)₂OR21, —S(O)₂OR21, —S(O)₀₋₂R21, —OP(O)OR22OR23, —P(O)OR22OR23, C1-6 alkyl, C6-10aryl-C1-6alkyl, C6-10aryl, C1-6alkoxy. C6-10aryl-C1-6alkoxy. C6-10aryloxy, 3-10 membered heterocycle, —C(O)R24, —C(O)OR24, —NR25C(O)R26 and —SO₂NR24R27:

R10 and R11 are each independently H or C1-6alkyl;

R20 are each independently C1-6 alkyl, C6-10aryl or 3-10 membered heterocycle;

R21 are each independently H, C1-6 alkyl, C6-10aryl or 3-10 membered heterocycle;

R22 and R23 are each independently H or C1-6alkyl;

R24 and R27 are each independently H, C1-6alkyl, C6-10aryl. C6-10aryl-C1-6alkyl or 3-10 membered heterocycle;

R25 is H or C1-6alkyl;

R26 are each independently H, C1-6alkyl, C6-10aryl, C6-10aryl-C1-6alkyl or 3-10 membered heterocycle;

or R25 and R26 are taken together with the atoms to which they are attached to form a 3 to 10 membered heterocycle.

In one embodiment, there is provided a compound of formula I or a pharmaceutically acceptable salt or solvate thereof, wherein A is an optionally substituted 3-11 membered heterocycle or an optionally substituted C6-10 aryl; W is CH; X is CR10R11 or NR10 wherein R10 and R11 are each independently H or C1-3 alkyl; R1 is H, or F; and R2 is as defined above.

In one embodiment, there is provided a compound of formula I or a pharmaceutically acceptable salt or solvate thereof, wherein A is an optionally substituted 3-11 membered heterocycle or an optionally substituted C6-10 aryl; W is CH; X is CR10R11 or NR10 wherein R10 and R11 are each independently H or methyl, ethyl, isopropyl or propyl; R1 is H, or F; and R2 is as defined above.

In one embodiment, there is provided a compound of formula I or a pharmaceutically acceptable salt or solvate thereof, wherein A is an optionally substituted monocyclic 3-6 membered heterocycle, an optionally substituted bicyclic 9-10 membered heterocycle or an optionally substituted phenyl or naphthyl; W is CH; X is CR10R11 or NR10 wherein R10 and R11 are each independently H or methyl, ethyl, isopropyl or propyl; R1 is H, or F; and R2 is as defined above.

In one embodiment, there is provided a compound of formula I or a pharmaceutically acceptable salt or solvate thereof, wherein A is an optionally substituted 3-11 membered heterocycle or an optionally substituted C6-10 aryl; W is CH; X is CH₂ or NH; R1 is H, or F; and R2 is as defined above.

In one embodiment, there is provided a compound of formula I or a pharmaceutically acceptable salt or solvate thereof, wherein A is an optionally substituted monocyclic 3-6 membered heterocycle, an optionally substituted bicyclic 9-10 membered heterocycle or an optionally substituted phenyl or naphthyl; W is CH; X is CH₂ or NH; R1 is H, or F; and R2 is as defined above.

In one embodiment, there is provided a compound of formula I or a pharmaceutically acceptable salt or solvate thereof, wherein A is an optionally substituted 3-11 membered heterocycle or an optionally substituted C6-10 aryl; W is CH; X is CH₂ or NH; R1 is H, or F; and R2 is one or more substituent each independently selected from halogen, amino, amido, cyano, hydroxyl, C1-6alkyl, C6-10aryl, C1-6alkoxy, C6-10aryloxy, 3-10 membered heterocycle, —C(O)R24, —C(O)OR24, —NR25C(O)R26 and —SO₂NR24R27; R24 and R27 are each independently H. C1-6 alkyl, C6-10 aryl; R25 is H or C1-6 alkyl; R26 is each independently H, C1-6 alkyl.

In one embodiment, there is provided a compound of formula I or a pharmaceutically acceptable salt or solvate thereof, wherein A is an optionally substituted monocyclic 3-6 membered heterocycle, an optionally substituted bicyclic 9-10 membered heterocycle or an optionally substituted phenyl or naphthyl; W is CH; X is CH₂ or NH; R1 is H, or F; and R2 is one or more substituent each independently selected from halogen, amino, amido, cyano, hydroxyl, C1-6alkyl, C6-10aryl, C1-6alkoxy, C6-10aryloxy, 3-10 membered heterocycle, —C(O)R24, —C(O)OR24, —NR25C(O)R26 and —SO₂NR24R27; R24 and R27 are each independently H, C1-6 alkyl, C6-10 aryl; R25 is H or C1-6 alkyl; R26 is each independently H, C1-6 alkyl.

In one embodiment, there is provided a compound of formula I or a pharmaceutically acceptable salt or solvate thereof, wherein A is an optionally substituted monocyclic 3-6 membered heterocycle, an optionally substituted bicyclic 9-10 membered heterocycle or an optionally substituted phenyl or naphthyl; W is CH; X is CH₂ or NH; R1 is H, or F; and R2 is hydrogen or one or more substituent each independently selected from halogen, amino, amido, cyano, hydroxyl, C1-6alkyl, optionally substituted C6-10aryl, C1-6alkoxy, C6-10aryloxy, optionally substituted 3-10 membered heterocycle, —C(O)R24, —C(O)OR24, —NR25C(O)R26 and —SO₂NR24R27; R24 and R27 are each independently H, C1-6 alkyl, C6-10 aryl; R25 is H or C1-6 alkyl; R26 is each independently H, C1-6 alkyl.

In one embodiment, there is provided a compound of formula I or a pharmaceutically acceptable salt or solvate thereof, wherein A is an optionally substituted 3-11 membered heterocycle or an optionally substituted C6-10 aryl; W is CH; X is CH$_2$ or NH; R1 is H, or F; and R2 is one or more substituent each independently selected from halogen, amino, amido, cyano, hydroxyl, C1-6alkyl, C6-10aryl, C1-6alkoxy, 3-10 membered heterocycle.

In one embodiment, there is provided a compound of formula I or a pharmaceutically acceptable salt or solvate thereof, wherein A is an optionally substituted 3-11 membered heterocycle or an optionally substituted C6-10 aryl; W is CH; X is CH$_2$ or NH; R1 is H, or F; and R2 is one or more substituent each independently selected from halogen, amino, amido, cyano, hydroxyl, optionally substituted C1-6alkyl, C6-10aryl. C1-6alkoxy, optionally substituted 3-10 membered heterocycle.

In one embodiment, there is provided a compound of formula I or a pharmaceutically acceptable salt or solvate thereof, wherein A is an optionally substituted 3-11 membered heterocycle or an optionally substituted C6-10 aryl; W is CH; X is CH$_2$ or NH; R1 is H, or F; and R2 is hydrogen or one or more substituent each independently selected from halogen, amino, amido, cyano, hydroxyl, optionally substituted C1-6alkyl, C6-10aryl, C1-6alkoxy, optionally substituted 3-10 membered heterocycle.

In one embodiment, there is provided a compound of formula I or a pharmaceutically acceptable salt or solvate thereof, wherein A is an optionally substituted monocyclic 3-6 membered heterocycle, an optionally substituted bicyclic 9-10 membered heterocycle or an optionally substituted phenyl or naphthyl; W is CH; X is CH$_2$ or NH; R1 is H, or F; and R2 is one or more substituent each independently selected from halogen, amino, amido, cyano, hydroxyl, C1-6alkyl, C6-10aryl, C1-6alkoxy, 3-10 membered heterocycle.

In one embodiment, there is provided a compound of formula I or a pharmaceutically acceptable salt or solvate thereof, wherein A is an optionally substituted monocyclic 3-6 membered heterocycle, an optionally substituted bicyclic 9-10 membered heterocycle or an optionally substituted phenyl or naphthyl; W is CH; X is CH$_2$ or NH; R1 is H, or F; and R2 is hydrogen or one or more substituent each independently selected from halogen, amino, amido, cyano, hydroxyl, optionally substituted C1-6alkyl, C6-10aryl, C1-6alkoxy, optionally substituted 3-10 membered heterocycle.

In one embodiment, there is provided a compound of formula I or a pharmaceutically acceptable salt or solvate thereof, wherein A is halogen, and W, X, R1 and R2 are as defined above.

In one embodiment, there is provided a compound of formula I or a pharmaceutically acceptable salt or solvate thereof, wherein A is halogen, preferably bromo, R2 is hydrogen, and W, X, and R1 are as defined above.

In another embodiment, there is also provided a compound of formula I as defined above or a pharmaceutically acceptable salt, solvate or prodrug thereof.

In another embodiment, there is also provided a compound of formula II

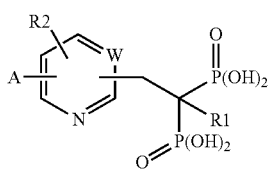

or a pharmaceutically acceptable salt or solvate thereof.

In another embodiment, there is provided a compound of formula IIa, formula IIb or formula IIc

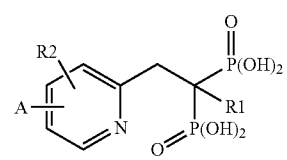

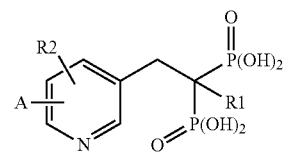

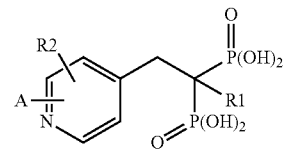

or a pharmaceutically acceptable salt or solvate thereof.

In another embodiment, there is provided a compound of formula III

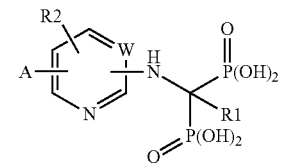

or a pharmaceutically acceptable salt or solvate thereof.

In another embodiment, there is provided a compound of formula IIIa, formula IIIb or formula IIIc

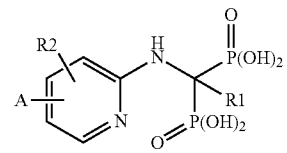

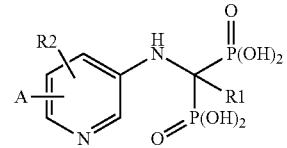

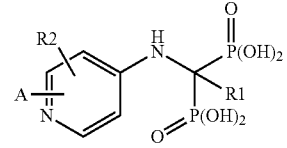

or a pharmaceutically acceptable salt or solvate thereof.

In yet another embodiment, there is provided a compound of formula IVa, formula IVb, formula IVc or formula IVd

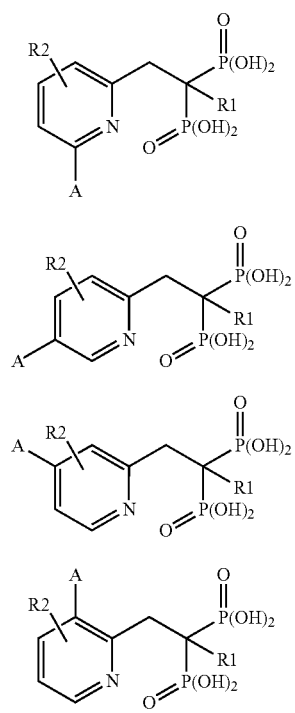

or a pharmaceutically acceptable salt or solvate thereof.

In yet another embodiment, there is provided a compound of formula Va, formula Vb, formula Vc or formula Vd

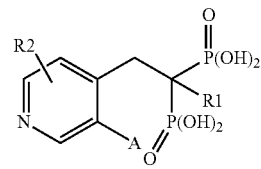

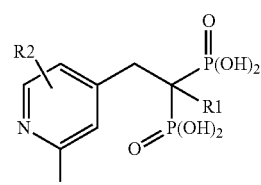

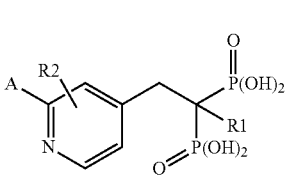

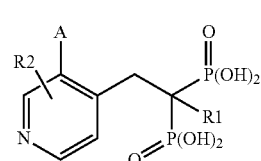

or a pharmaceutically acceptable salt or solvate thereof.

In yet another embodiment, there is provided a compound of formula VIa, formula VIb, formula VIc, formula VId or a pharmaceutically acceptable salt or solvate thereof.

In yet another embodiment, there is provided a compound of formula VIIIa, formula VIIb, formula VIIc or formula VIId

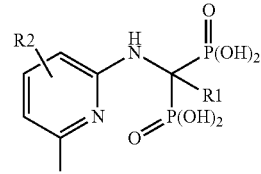

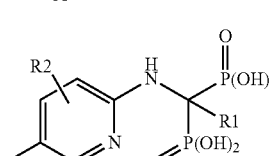

or a pharmaceutically acceptable salt or solvate thereof.

In yet another embodiment, there is provided a compound of formula VIIIa, formula VIIIb, formula VIIIc or formula VIIId

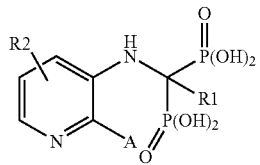
VIIIa

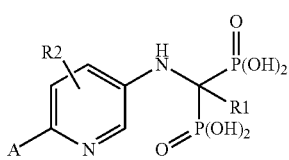
VIIIb

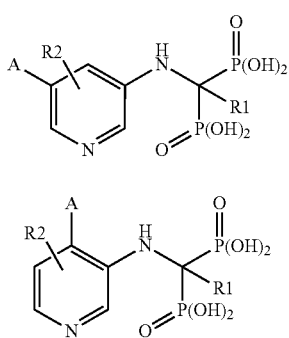
VIIIc

VIIId or a pharmaceutically acceptable salt or solvate thereof.

In yet another embodiment, there is provided a compound of formula IXa, formula IXb, formula IXc, or formula IXd

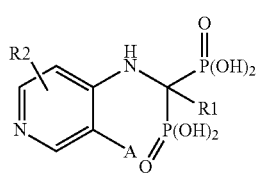
IXa

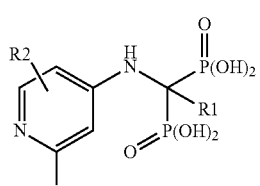
IXb

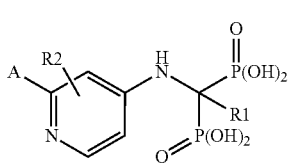
IXc

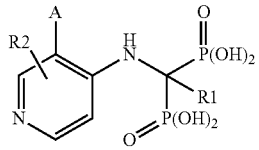
IXd or a pharmaceutically acceptable salt or solvate thereof.

In one embodiment, there is provided a compound of formula I or a pharmaceutically acceptable salt or solvate thereof, wherein X is $CH_2$ or NH.

In one embodiment, there is provided a compound of formula I, II, III, IIa, IIb, IIc, IIIa, IIIb, IIIc, IVa, IVb, IVc, IVd, Va, Vb, Vc, Vd, VIa, VIb, VIc, VIId, VIIa, VIIb, VIIc, VIId, VIIIa, VIIIb, VIIIc, VIIId, IXa, IXb, IXc or IXd or a pharmaceutically acceptable salt or solvate thereof, wherein A is an optionally substituted 3-11 membered heterocycle.

In another embodiment, there is provided a compound of formula I, II, III, IIa, IIb, IIc, IIIa, IIIb, IIIc, IVa, IVb, IVc, IVd, Va, Vb, Vc, Vd, VIa, VIIb, VIIc, VIId, VIIa, VIIb, VIIc, VIId, VIIIa, VIIIb, VIIIc, VIIId, IXa, IXb, IXc or IXd or a pharmaceutically acceptable salt or solvate thereof, wherein A is an optionally substituted C6-10 aryl.

In another embodiment, there is provided a compound of formula I, II, III, IIa, IIb, IIc, IIIa, IIIb, IIIc, IVa, IVb, IVc, IVd, Va, Vb, Vc, Vd, VIa, VIIb, VIIc, VIId, VIIa, VIIb, VIIc, VIId, VIIIa, VIIIb, VIIIc, VIIId, IXa, IXb, IXc or IXd or a pharmaceutically acceptable salt or solvate thereof, wherein A is an optionally substituted 3-11 membered heterocycle and R1 is F.

In another embodiment, there is provided a compound of formula I, II, III, IIa, IIb, IIc, IIIa, IIIb, IIIc, IVa, IVb, IVc, IVd, Va, Vb, Vc, Vd, VIa, VIb, VIc, VIId, VIIa, VIIb, VIIc, VIId, VIIIa, VIIIb, VIIIc, VIIId, IXa, IXb, IXc or IXd or a pharmaceutically acceptable salt or solvate thereof, wherein A is an optionally substituted 3-11 membered heterocycle and R1 is OH.

In another embodiment, there is provided a compound of formula I, II, III, IIa, IIb, IIc, IIIa, IIIb, IIIc, IVa, IVb, IVc, IVd, Va, Vb, Vc, Vd, VIa, VIIb, VIIc, VIId, VIIa, VIIb, VIIc, VIId, VIIIa, VIIIb, VIIIc, VIIId, IXa, IXb, IXc or IXd or a pharmaceutically acceptable salt or solvate thereof, wherein A is an optionally substituted 3-11 membered heterocycle and R1 is H.

In another embodiment, there is provided a compound of formula I, II, III, IIa, IIb, IIc, IIIa, IIIb, IIIc, IVa, IVb, IVc, IVd, Va, Vb, Vc, Vd, VIa, VIb, VIc, VIId, VIIa, VIIb, VIIc, VIId, VIIIa, VIIIb, VIIIc, VIIId, IXa, IXb, IXc or IXd or a pharmaceutically acceptable salt or solvate thereof, wherein A is an optionally substituted C6-10 aryl and R1 is F.

In another embodiment, there is provided a compound of formula I, II, III, IIa, IIb, IIc, IIIa, IIIb, IIIc, IVa, IVb, IVc, IVd, Va, Vb, Vc, Vd, VIa, VIIb, VIIc, VIId, VIIa, VIIb, VIIc, VIId, VIIIa, VIIIb, VIIIc, VIIId, IXa, IXb, IXc or IXd or a pharmaceutically acceptable salt or solvate thereof, wherein A is an optionally substituted C6-10 aryl and R1 is H.

In another embodiment, there is provided a compound of formula I, II, III, IIa, IIb, IIc, IIIa, IIIb, IIIc, IVa, IVb, IVc, IVd, Va, Vb, Vc, Vd, VIa, VIb, VIc, VId, VIIa, VIIb, VIIc, VIId, VIIIa, VIIIb, VIIIc, VIIId, IXa, IXb, IXc or IXd or a pharmaceutically acceptable salt or solvate thereof, wherein A is an optionally substituted C6-10 aryl and R1 is OH.

In one embodiment, there is provided a compound of formula I, II or III or a pharmaceutically acceptable salt or solvate thereof, wherein W is N.

In another embodiment, there is provided a compound of formula I, II or III or a pharmaceutically acceptable salt or solvate thereof, wherein W is N and A is an optionally substituted 3-11 membered heterocycle.

In yet another embodiment, there is provided a compound of formula I, II or III or a pharmaceutically acceptable salt or solvate thereof, wherein W is N and A is an optionally substituted C6-10 aryl.

In another embodiment, there is provided a compound of formula I, II or III or a pharmaceutically acceptable salt or solvate thereof, wherein W is N, A is an optionally substituted 3-11 membered heterocycle and R1 is F.

In another embodiment, there is provided a compound of formula I, II or III or a pharmaceutically acceptable salt or solvate thereof, wherein W is N, A is an optionally substituted 3-11 membered heterocycle and R1 is OH.

In another embodiment, there is provided a compound of formula I, II or III or a pharmaceutically acceptable salt or solvate thereof, wherein W is N, A is an optionally substituted 3-11 membered heterocycle and R1 is H.

In yet another embodiment, there is provided a compound of formula I, II or III or a pharmaceutically acceptable salt or solvate thereof, wherein W is N, A is an optionally substituted C6-10 aryl and R1 is F.

In yet another embodiment, there is provided a compound of formula I, II or III or a pharmaceutically acceptable salt or solvate thereof, wherein W is N, A is an optionally substituted C6-10 aryl and R1 is OH.

In yet another embodiment, there is provided a compound of formula I, II or III or a pharmaceutically acceptable salt or solvate thereof, wherein W is N, A is an optionally substituted C6-10 aryl and R1 is H.

In another embodiment, there is also provided a compound of formula I, II, III, IIa, IIb, IIc, IIIa, IIIb, IIIc, IVa, IVb, IVc, IVd, Va, Vb, Vc, Vd, VIa, VIIb, VIIc, VIId, VIIa, VIIb, VIIc, VIId, VIIIa, VIIIb, VIIIc, VIIId, IXa, IXb, IXc or IXd as defined above or a pharmaceutically acceptable salt, solvate or prodrug thereof.

In accordance with one embodiment, the present disclosure provides a compound of formula I, II or III or a pharmaceutically acceptable salt or solvate thereof, wherein W is N and R2 and A may be attached at the following positions as indicated by the arrows in any combination, all of which are being contemplated:

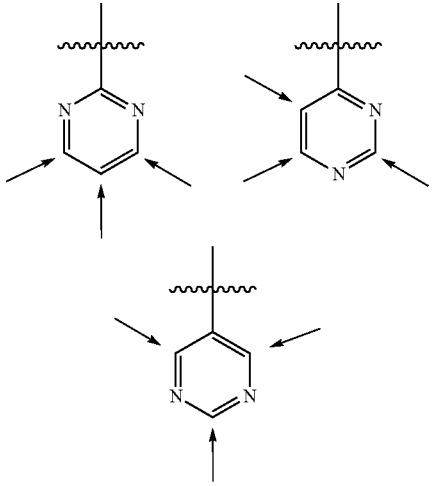

In accordance with another embodiment, there is provided a compound of the present disclosure or a pharmaceutically acceptable salt or solvate thereof, wherein A is an optionally substituted 3-6 membered monocyclic heterocycle.

In accordance with another embodiment, there is provided a compound of the present disclosure or a pharmaceutically acceptable salt or solvate thereof, wherein A is an optionally substituted 5-6 membered monocyclic heterocycle.

In accordance with another embodiment, there is provided a compound of the present disclosure or a pharmaceutically acceptable salt or solvate thereof, wherein A is an optionally substituted 7 to 12 membered bicyclic heterocycle.

In accordance with another embodiment, there is provided a compound of the present disclosure or a pharmaceutically acceptable salt or solvate thereof, wherein A is an optionally substituted 9 to 10 membered bicyclic heterocycle.

In accordance with another embodiment, there is provided a compound of the present disclosure or a pharmaceutically acceptable salt or solvate thereof, wherein A is an optionally substituted azepinyl, aziridinyl, azetyl, azetidinyl, diazepinyl, dithiadiazinyl, dioxazepinyl, dioxolanyl, dithiazolyl, furanyl, isooxazolyl, isothiazolyl, imidazolyl, morpholinyl, morpholino, oxetanyl, oxadiazolyl, oxiranyl, oxazinyl oxazolyl, piperazinyl, pyrazinyl, pyridazinyl, pyrimidinyl, piperidyl, piperidino, pyridyl, pyranyl, pyrazolyl, pyrrolyl, pyrrolidinyl, thiatriazolyl, tetrazolyl, thiadiazolyl, triazolyl, thiazolyl, thienyl, tetrazinyl, thiadiazinyl, triazinyl, thiazinyl and thiopyranyl, furoisoxazolyl, imidazothiazolyl, thienoisothiazolyl, thienothiazolyl, imidazopyrazolyl, cyclopentapyrazolyl, pyrrolopyrrolyl, thienothienyl, thiadiazolopyrimidinyl, thiazolothiazinyl, thiazolopyrimidinyl, thiazolopyridinyl, oxazolopyrimidinyl, oxazolopyridyl, benzoxazolyl, benzisothiazolyl, benzothiazolyl, imidazopyrazinyl, purinyl, pyrazolopyrimidinyl, imidazopyridinyl, benzimidazolyl, indazolyl, benzoxathiolyl, benzodioxolyl, benzodithiolyl, indolizinyl, indolinyl, isoindolinyl, furopyrimidinyl, furopyridyl, benzofuranyl, isobenzofuranyl, thienopyrimidinyl, thienopyridyl, benzothienyl, cyclopentaoxazinyl, cyclopentafuranyl, benzoxazinyl, benzothiazinyl, quinazolinyl, naphthyridinyl, quinolinyl, isoquinolinyl, benzopyranyl, pyridopyridazinyl and pyridopyrimidinyl.

In accordance with another embodiment, there is provided a compound of the present disclosure or a pharmaceutically acceptable salt or solvate thereof, wherein A is an optionally substituted azepinyl, aziridinyl, azetyl, azetidinyl, diazepinyl, dithiadiazinyl, dioxazepinyl, dioxolanyl, dithiazolyl, furanyl, isooxazolyl, isothiazolyl, imidazolyl, morpholinyl, morpholino, oxetanyl, oxadiazolyl, oxiranyl, oxazinyl oxazolyl, piperazinyl, pyrazinyl, pyridazinyl, pyrimidinyl, piperidyl, piperidino, pyridyl, pyranyl, pyrazolyl, pyrrolyl, pyrrolidinyl, thiatriazolyl, tetrazolyl, thiadiazolyl, triazolyl, thiazolyl, thienyl, tetrazinyl, thiadiazinyl, triazinyl, thiazinyl and thiopyranyl.

In accordance with another embodiment, there is provided a compound of the present disclosure or a pharmaceutically acceptable salt or solvate thereof, wherein A is an optionally substituted, diazepinyl, furanyl, isooxazolyl, isothiazolyl, imidazolyl, morpholinyl, morpholino, oxadiazolyl, oxazolyl, piperazinyl, pyrazinyl, pyridazinyl, pyrimidinyl, piperidyl, piperidino, pyridyl, pyranyl, pyrazolyl, pyrrolyl, pyrrolidinyl, thiatriazolyl, tetrazolyl, thiadiazolyl, triazolyl, thiazolyl, thienyl, tetrazinyl, thiadiazinyl, triazinyl, thiazinyl and thiopyranyl.

In accordance with another embodiment, there is provided a compound of the present disclosure or a pharmaceutically acceptable salt or solvate thereof, wherein A is an optionally substituted furoisoxazolyl, imidazothiazolyl, thienoisothiazolyl, thienothiazolyl, imidazopyrazolyl, cyclopentapyrazolyl, pyrrolopyrrolyl, thienothienyl, thiadiazolopyrimidinyl, thiazolothiazinyl, thiazolopyrimidinyl, thiazolopyridinyl, oxazolopyrimidinyl, oxazolopyridyl, benzoxazolyl, benzisothiazolyl, benzothiazolyl, imidazopyrazinyl, purinyl, pyrazolopyrimidinyl, imidazopyridinyl, benzimidazolyl, indazolyl, benzoxathiolyl, benzodioxolyl, benzodithiolyl, indolizinyl, indolinyl, isoindolinyl, furopyrimidinyl, furopyridyl, benzofuranyl, isobenzofuranyl, thienopyrimidinyl, thienopyridyl, benzothienyl, cyclopentaoxazinyl, cyclopentafuranyl, benzoxazinyl, benzothiazinyl, quinazolinyl, naphthyridinyl, quinolinyl, isoquinolinyl, benzopyranyl, pyridopyridazinyl and pyridopyrimidinyl.

In accordance with another embodiment, there is provided a compound of the present disclosure or a pharmaceutically acceptable salt or solvate thereof, wherein A is an optionally substituted benzoxazolyl, benzisothiazolyl, benzothiazolyl, benzimidazolyl, benzoxathiolyl, benzodioxolyl, benzodithiolyl, benzofuranyl, isobenzofuranyl, benzothienyl, benzoxazinyl, benzothiazinyl, benzopyranyl, quinolinyl and isoquinolinyl.

In accordance with another embodiment, there is provided a compound of the present disclosure or a pharmaceutically acceptable salt or solvate thereof, wherein A is an optionally substituted furoisoxazolyl, imidazothiazolyl, thienoisothiazolyl, thienothiazolyl, imidazopyrazolyl, pyrrolopyrrolyl, thienothienyl, thiadiazolopyrimidinyl, thiazolothiazinyl, thiazolopyrimidinyl, thiazolopyridinyl, oxazolopyrimidinyl, oxazolopyridyl, imidazopyrazinyl, pyrazolopyrimidinyl, imidazopyridinyl, furopyrimidinyl, furopyridyl, thienopyrimidinyl, thienopyridyl, quinazolinyl, naphthyridinyl, pyridopyridazinyl and pyridopyrimidinyl.

In accordance with another embodiment, there is provided a compound of the present disclosure or a pharmaceutically acceptable salt or solvate thereof, wherein A is an optionally substituted C6-8aryl.

In accordance with another embodiment, there is provided a compound of the present disclosure or a pharmaceutically acceptable salt or solvate thereof, wherein A is an optionally substituted phenyl, tolyl, dimethylphenyl, aminophenyl, anilinyl, naphthyl, anthryl, phenanthryl or biphenyl.

In accordance with another embodiment, there is provided a compound of the present disclosure or a pharmaceutically acceptable salt or solvate thereof, wherein A is an optionally substituted phenyl.

In accordance with another embodiment, there is provided a compound of the present disclosure or a pharmaceutically acceptable salt or solvate thereof, wherein A is as defined above and is optionally substituted with at least one of C1-4 alkyl, perfluoro C1-3 alkyl, C1-4 alkoxy and halogen; preferably $CH_3$, $CF_3$, $OCH_3$, $OCHCH_3CH_3$, fluoro, chloro or bromo.

In accordance with another embodiment, there is provided a compound of the present disclosure or a pharmaceutically acceptable salt or solvate thereof, wherein R2 is one or more substituents and each is independently selected from halogen, C1-6alkyl, C2-6alkenyl, C2-6alkynyl, C1-6 alkoxy, C2-6alkenyloxy, C2-6alkynyloxy, —NR30R31, —C(O)NR30R31, —NR30COR31, carboxy, azido, cyano, hydroxyl, nitro, nitroso, —OR30, —SR30, —S(O)$_{0-2}$R30, —C(O)R30, —C(O)OR30 and —SO$_2$NR30R31; wherein R30 and R31 are each independently H, halogen, C1-6alkyl, C2-6alkenyl or C2-6alkynyl.

In accordance with another embodiment, there is provided a compound of the present disclosure or a pharmaceutically acceptable salt or solvate thereof, wherein R2 is hydrogen.

In accordance with another embodiment, there is provided a compound of the present disclosure or a pharmaceutically acceptable salt or solvate thereof, wherein R2 is optionally substituted 3-membered heterocycle.

In accordance with another embodiment, there is provided a compound of the present disclosure or a pharmaceutically acceptable salt or solvate thereof, wherein R2 is 3-10 membered heterocycle.

In accordance with another embodiment, there is provided a compound of the present disclosure or a pharmaceutically acceptable salt or solvate thereof, wherein R2 is 3-10 membered heterocycle or C6-10aryl optionally substituted with at least one of C1-4 alkyl, perfluoro C1-3 alkyl, C1-4 alkoxy and halogen; preferably $CH_3$, $CF_3$, $OCH_3$, $OCHCH_3CH_3$, fluoro, chloro or bromo.

In accordance with another embodiment, there is provided the compounds of Table 1, or a pharmaceutically acceptable salt or solvate thereof.

In accordance with another embodiment, there is provided the compounds of Table 1, or a pharmaceutically acceptable salt, solvate or prodrug thereof.

In one embodiment, there is provided a method or use for treating or preventing osteoporosis, viral infection, cancer, preventing or slowing the progression of Phospho-Tau-dependent neurodegenerative diseases such as Alzheimer's, or lowering of cholesterol, comprising administering a therapeutically effective amount of a compound as defined herein, or a pharmaceutically acceptable salt or solvate thereof to a patient.

At least some the compounds described herein may advantageously provide selectivity toward hFPPS which means that they may inhibit to a lesser extent other related enzymes. In one embodiment, at least some of the compounds defined herein have a selective inhibition having regard to GGPPS (geranylgeranyl pyrophosphate synthase) and/or and hSQS (human squalene synthase).

The term "alkyl" represents a linear or branched moiety. Examples of "alkyl" groups include but are not limited to methyl, ethyl, propyl, isopropyl, butyl, isobutyl, sec-butyl, tert-butyl, pentyl, isopentyl, neopentyl, tert-pentyl, hexyl, isohexyl or neohexyl. The term "alkyl" is also meant to include alkyls in which one or more hydrogen atoms are replaced by a halogen, ie. an alkylhalide. Examples include but are not limited to trifluoromethyl, difluoromethyl, fluoromethyl, trichloromethyl, dichloromethyl, chloromethyl, trifluoroethyl, difluoroethyl, fluoroethyl, trichloroethyl, dichloroethyl, chloroethyl, chlorofluoromethyl, chlorodifluoromethyl, dichlorofluoroethyl.

The terms "alkenyl" and "alkynyl" represent a linear or branched hydrocarbon moiety which has one or more double bonds or triple bonds in the chain. Examples of alkenyl, and alkynyl groups include but are not limited to, allyl, vinyl, acetylenyl, ethylenyl, propenyl, isopropenyl, butenyl, isobutenyl, hexenyl, butadienyl, pentenyl, pentadienyl, hexenyl, hexadienyl, hexatrienyl, heptenyl, heptadienyl, heptatrienyl, octenyl, octadienyl, octatrienyl, octatetraenyl, propynyl, butynyl, pentynyl and hexynyl.

The terms "alkoxy," "alkenyloxy," and "alkynyloxy" represent an alkyl, alkenyl or alkynyl moiety, respectively, which is covalently bonded to the adjacent atom through an oxygen atom. Examples include but are not limited to methoxy, ethoxy, propoxy, isopropoxy, butoxy, isobutoxy, sec-butoxy, tert-butoxy, pentyloxy, isopentyloxy, neopentyloxy, tert-pentyloxy, hexyloxy, isohexyloxy, trifluoromethoxy and neohexyloxy.

As used herein, amino include amino which are unsubstituted such as —NH$_2$, or substituted with one or two C1-6alkyl or aryl such as —NH(C$_{1-6}$alkyl), —N(C$_{1-6}$alkyl)$_2$, —N(C$_{1-6}$alkyl)(aryl) and —N(aryl)$_2$.

The term "aryl" represents a carbocyclic moiety containing at least one benzenoid-type ring (i.e., may be monocyclic or polycyclic), Examples include but are not limited to phenyl, tolyl, dimethylphenyl, aminophenyl, anilinyl, naphthyl, anthryl, phenanthryl or biphenyl.

The term "aryloxy" represents an aryl moiety, which is covalently bonded to the adjacent atom through an oxygen atom. Examples include but are not limited to phenoxy, dimethylphenoxy, aminophenoxy, anilinoxy, naphthoxy, anthroxy, phenanthroxy or biphenoxy.

The term "arylalkyl" represents an aryl group attached to the adjacent atom by an alkyl, alkenyl or alkynyl. Examples include but are not limited to benzyl, benzhydryl, trityl, phenethyl, 3-phenylpropyl, 2-phenylpropyl, 4-phenylbutyl and naphthylmethyl.

The term "arylalkyloxy" represents an arylalkyl moiety, which is covalently bonded to the adjacent atom through an oxygen atom. Examples include but are not limited to benzyloxy, benzhydroxy, trityloxy, phenethyloxy, 3-phenylpropoxy, 2-phenylpropoxy, 4-phenylbutoxy and naphthylmethoxy.

The term "heterocycle" represents a 3 to 11 membered optionally substituted saturated, unsaturated, partially saturated or aromatic cyclic moiety wherein said cyclic moiety is interrupted by at least one heteroatom selected from oxygen (O), sulfur (S) or nitrogen (N). Heterocycles may be monocyclic or polycyclic rings. Heterocycles may be 3 to 6 membered monocyclic ring or 5 to 6 membered monocyclic ring. Heterocycles may be 7 to 12 membered bicyclic ring or 9 to 10 membered bicyclic ring. Examples of heterocycles include but are not limited to azepinyl, aziridinyl, azetyl, azetidinyl, diazepinyl, dithiadiazinyl, dioxazepinyl, dioxolanyl, dithiazolyl, furanyl, isooxazolyl, isothiazolyl, imidazolyl, morpholinyl, morpholino, oxetanyl, oxadiazolyl, oxiranyl, oxazinyl oxazolyl, piperazinyl, pyrazinyl, pyridazinyl, pyrimidinyl, piperidyl, piperidino, pyridyl, pyranyl, pyrazolyl, pyrrolyl, pyrrolidinyl, thiatriazolyl, tetrazolyl, thiadiazolyl, triazolyl, thiazolyl, thienyl, tetrazinyl, thiadiazinyl, triazinyl, thiazinyl and thiopyranyl, furoisoxazolyl, imidazothiazolyl, thienoisothiazolyl, thienothiazolyl, imidazopyrazolyl, cyclopentapyrazolyl, pyrrolopyrrolyl, thienothienyl, thiadiazolopyrimidinyl, thiazolothiazinyl, thiazolopyrimidinyl, thiazolopyridinyl, oxazolopyrimidinyl, oxazolopyridyl, benzoxazolyl, benzisothiazolyl, benzothiazolyl, imidazopyrazinyl, purinyl, pyrazolopyrimidinyl, imidazopyridinyl, benzimidazolyl, indazolyl, benzoxathiolyl, benzodioxolyl, benzodithiolyl, indolizinyl, indolinyl, isoindolinyl, furopyrimidinyl, furopyridyl, benzofuranyl, isobenzofuranyl, thienopyrimidinyl, thienopyridyl, benzothienyl, cyclopentaoxazinyl, cyclopentafuranyl, benzoxazinyl, benzothiazinyl, quinazolinyl, naphthyridinyl, quinolinyl, isoquinolinyl, benzopyranyl, pyridopyridazinyl and pyridopyrimidinyl.

When heterocycle is a polycyclic ring, the rings comprise at least one ring comprising the heteroatom and the other rings may be cycloalkyl, aryl or heterocycle and the point of attachment may be on any available atom. For example if the heterocycle is a bicyclic moiety such as illustrated below, the point of attachment can be on any available carbon atom:

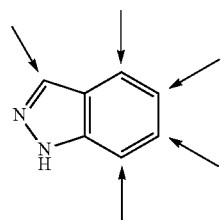

"Halogen atom" is specifically a fluorine atom, chlorine atom, bromine atom or iodine atom.

The term "optionally substituted" represents at each occurance and independently, one or more halogen, amino, amidino, amido, azido, cyano, guanido, hydroxyl, nitro, nitroso, urea, OS(O)$_2$Rm (wherein Rm is selected from C1-6alkyl, C6-10aryl or 3-10 membered heterocycle), OS(O)$_2$ORn (wherein Rn is selected from H, C1-6alkyl, C6-110aryl or 3-10 membered heterocycle), S(O)$_2$ORp (wherein Rp is selected from H, C1-6alkyl, C6-10aryl and 3-10 membered heterocycle), S(O)O$_{0-2}$Rq (wherein Rq is selected from H, C1-6alkyl, C6-10aryl or 3-10 membered heterocycle), OP(O)ORsORt, P(O)ORsORt (wherein Rs and Rt are each independently selected from H or C1-6alkyl), C1-6alkyl, C6-10aryl-C1-6alkyl, C6-10aryl, C1-6alkoxy, C6-10aryl-C1-6alkyloxy, C6-10aryloxy, 3-10 membered heterocycle, C(O)Ru (wherein Ru is selected from H, C1-6alkyl, C6-10aryl, C6-10aryl-C1-6alkyl or 3-10 membered heterocycle), C(O)ORv (wherein Rv is selected from H, C1-6alkyl, C6-10aryl, C6-10aryl-C1-6alkyl or 3-10 membered heterocycle), NRxC(O)Rw (wherein Rx is H or C1-6alkyl and Rw is selected from H, C1-6alkyl, C6-10aryl, C6-10aryl-C1-6alkyl or 3-10 membered heterocycle, or Rx and Rw are taken together with the atoms to which they are attached to form a 3 to 10 membered heterocycle) or SO2NRyRz (wherein Ry and Rz are each independently selected from H, C1-6alkyl, C6-10aryl, C3-10heterocycle or C6-10aryl-C1-6alkyl). In another embodiment, the term "optionally substituted" represents halogen, C1-6alkyl, C2-6alkenyl, C2-6alkynyl, C1-6 alkoxy, C2-6alkenyloxy, C2-6alkynyloxy, —NR40R41, —C(O)NR40R41, —NR40COR41, carboxy, azido, cyano, hydroxyl, nitro, nitroso, —OR40, —SR40, —S(O)$_{0-2}$R40, —C(O)R40, —C(O)OR40 and —SO$_2$NR40R41; wherein R40 and R41 are each independently H, halogen, C1-6alkyl, C2-6alkenyl or C2-6alkynyl.

The term "independently" means that a substituent can be the same or a different definition for each item.

The excipient(s) must be "pharmaceutically acceptable" in the sense of being compatible with the other ingredients of the formulation and not being deleterious to the recipient thereof.

In one embodiment, compounds as defined herein also include prodrugs. The term "prodrug" as used herein refers to a derivative of said compound which may be in an inactive or less active form and that, when administered to a biological system, generates or liberates the biologically active compound as a result of spontaneous chemical reaction(s), enzyme catalyzed chemical reactions(s), metabolic chemical reaction(s) or a combination thereof. The expression "prodrug" includes, but is not limited to, bisphosphate ester of a compound as described herein, such the tetrakispivaloyloxymethyl ester.

In a further embodiment, the expression "viral infection" includes, but is not limited to hepatitis A, B and C, human immunodeficiency virus (HIV), human cytomegalovirus (HCMV) and respiratory syncytial virus (RSV). As used herein, the term "viral infection" refers to any stage of a viral infection, including incubation phase, latent or dormant phase, acute phase, and development and maintenance of immunity towards a virus. Viral infections include, but are not limited to those caused by Adenovirus, Lassa fever virus (Arenavirus), Astroviras, Hantavirus, Rift Valley Fever virus (Phlebovirus), Caliciviras, Ebola virus, Marburg Virus, Japanese encephalitis virus, Dengue virus, Yellow fever virus, Hepatitis A virus, Hepatitis C virus, Hepatitis G virus, Hepatitis B virus, Hepatitis D virus, Herpes simplex virus 1, Herpes simplex virus 2, Cytomegalovirus, Epstein Barr virus, Varicella Zoster virus, Human Herpesvirus 7, Human Herpesvirus 8, Influenza virus, Parainfluenza virus, Rubella virus, Mumps virus, Morbillivirus, Measles virus, Respiratory Syncytial virus, Papillomaviruses, JC virus (Polyomavirus), BK virus (Polyomavirus), Parvovirus, Coxsackie virus (A and B), Polioviruses, Rhinoviruses, Reovirus, Rabies Virus (Lyssavirus), Human Immunodeficiency virus 1 and 2, and Human T-cell Leukemia virus. Examples of viral infections include Adenovirus acute respiratory disease, Lassa fever, Astrovirus enteritis, Hantavirus pulmonary syndrome, Rift valley fever, Ebola hemorrhagic fever, Marburg hemorrhagic fever, Japanese encephalitis, Dengue fever, Yellow fever, Hepatitis C, Hepatitis G, Hepatitis B, Hepatitis D, Hepatitis E, cold sores, genital sores, Cytomegalovirus infection, Mononucleosis, Chicken Pox, Shingles, Human Herpesvirus infection 7, Kaposi Sarcoma, Influenza, Brochiolitis, German measles (rubeola), Mumps, Measles, Brochiolitis, Papillomas (Warts), cervical cancer, progressive multifocal leukoencephalopathy, kidney disease, Erythema infectiosum, viral myocarditis, meninigitis, entertitis, Hepatitis, Poliomyelitis, the common cold, diarrhoea, Rabies, AIDS and Leukemia.

In another embodiment, the expression "cancer" includes, but is not limited to, multiple myeloma, tumors of mesenchymal origin, including fibrosarcoma and rhabdomyosarcoma; and other tumors, including melanoma, seminoma, tetratocarcinoma, neuroblastoma and glioma. Examples of cancer include: carcinoma, including that of the bladder, breast, colon, kidney, liver, lung, ovary, pancreas, stomach, cervix, thyroid and skin; hematopoietic tumors of lymphoid lineage, including acute lymphocytic leukemia, B-cell lymphoma and Burketts lymphoma; hematopoietic tumors of myeloid lineage, including acute and chronic myelogenous leukemias and promyelocytic leukemia; tumors of mesenchymal origin, including fibrosarcoma and rhabdomyosarcoma; and other tumors, including melanoma, seminoma, tetratocarcinoma, neuroblastoma and glioma.

In another embodiment, the present invention provides a combination comprising a therapeutically effective amount of a compound, as defined herein, and a therapeutically effective amount of at least one or more therapeutic agents useful in the method of the present disclosure.

It will be clear to a person of ordinary skill that if a further additional therapeutic agent is required or desired, ratios will be readily adjusted. It will be understood that the scope of combinations described herein is not particularly limited, but includes in principle any therapeutic agent useful for the prevention and treatment of osteoporosis (including but not limited to alendronate, risedronate or zoledronate), cancer (including but not limited to imatinib, taxol, cisplatin, doxorubicine, vinblastine, zoledronate and/or in conjunction with antimetastatic agents, antiangionevic agents such as avastatin, and antiapoptotic compounds such as Valcade), viral infection (for example in the treatment of HIV, the combination could include, inhibitors of virally encoded enzymes such as nucleoside or non-nucleoside reverse transcriptase inhibitors, protease inhibitors, integrase inhibitors, or inhibitors of viral fusion, entry inhibitors or any other step of the viral life cycle), or lowering of cholesterol. For immunomodulation, the combination may include NDAIDS, glucocorticoids or methotrexate. For prevention or treatment of neurodegenerative diseases, such as Alzheimer's, it may include acetylcholinesterase inhibitors.

It will be appreciated that the amount of a compound of the invention required for use in treatment will vary not only with the particular compound selected but also with the route of administration, the nature of the condition for which treatment is required and the age and condition of the patient and will be ultimately at the discretion of the attendant physician. Generally, the amount administered will be empirically determined, typically in the range of about 10 µg to 100 mg/kg body weight of the recipient.

The desired dose may conveniently be presented in a single dose or as divided dose administered at appropriate intervals, for example as two, three, four or more doses per day.

Pharmaceutical compositions include, without limitation, those suitable for oral, (including buccal and sub-lingual), transdermal, or parenteral (including intramuscular, sub-cutaneous and intravenous) administration or in a form suitable for administration by inhalation.

The formulations may, where appropriate, be conveniently presented in discrete dosage units and may be prepared by any of the methods well known in the art of pharmacy. The methods for preparing a pharmaceutical composition can include the steps of bringing into association the compound as defined herein and pharmaceutically acceptable excipients and then, if necessary, shaping the product into the desired formulation, including applying a coating when desired.

Pharmaceutical compositions suitable for oral administration may conveniently be presented as discrete units such as capsules, cachets or tablets each containing a predetermined amount of the active ingredient; as a powder or granules; as a solution, a suspension or as an emulsion. Tablets and capsules for oral administration may contain conventional excipients such as binding agents, fillers, lubricants, disintegrants, or wetting agents. The tablets may be coated according to methods well known in the art. Oral liquid preparations may be in the form of, for example, aqueous or oily suspensions, solutions, emulsions, syrups or elixirs, or may be presented as a dry product for constitution with water or other suitable vehicle before use. Such liquid preparations may contain conventional additives such as suspending agents, emulsifying agents, non-aqueous vehicles (which may include edible oils), or preservatives.

The compounds and combinations as defined herein may also be formulated for parenteral administration (e.g. by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, and may contain formulatory agents such as suspending, stabilizing and/or dispersing agents. Alternatively, the active ingredient may be in powder form, obtained by aseptic isolation of sterile solid or by lyophilisation from solution, for constitution with a suitable vehicle, e.g. sterile water or saline, before use.

Compositions suitable for topical administration in the mouth include lozenges comprising the active ingredient in a flavoured base, usually sucrose and acacia or tragacanth; pastilles comprising the active ingredient in an inert base such as gelatin and glycerin or sucrose and acacia; and mouthwashes comprising the active ingredient in a suitable liquid carrier.

For administration by inhalation, the compounds and combinations as defined herein may take the form of a dry powder composition, for example a powder mix of the compound and a suitable powder base such as lactose or starch. The powder composition may be presented in unit dosage form in, for example, capsules or cartridges or e.g. gelatin or blister packs from which the powder may be administered with the aid of an inhalator or insufflator.

The compounds as defined herein may include a chiral center which gives rise to enantiomers. The compounds may thus exist in the form of two different optical isomers, that is (+) or (−) enantiomers. All such enantiomers and mixtures thereof, including racemic or other ratio mixtures of individual enantiomers, are included within the scope of the invention. The single enantiomer can be obtained by methods well known to those of ordinary skill in the art, such as chiral HPLC, enzymatic resolution and chiral auxiliary derivatization.

It will also be appreciated that the compounds in accordance with the present disclosure can contain more than one chiral centre. The compounds of the present invention may thus exist in the form of different diastereomers. All such diastereomers and mixtures thereof are included within the scope of the invention. The single diastereomer can be obtained by methods well known in the art, such as HPLC, crystalisation and chromatography.

There is also provided pharmaceutically acceptable salts of the compounds of the present invention. What is meant by the term pharmaceutically acceptable salts of the compounds is that they are derived from pharmaceutically acceptable inorganic and organic acids and bases. Examples of suitable acids include but are not limited to hydrochloric, hydrobromic, sulphuric, nitric, perchloric, fumaric, maleic, phosphoric, glycollic, lactic, salicylic, succinic, toleune-p-sulphonic, tartaric, acetic, trifluoroacetic, citric, methanesulphonic, formic, benzoic, malonic, naphthalene-2-sulphonic and benzenesulphonic acids. Other acids such as oxalic, while not in themselves pharmaceutically acceptable, may be useful as intermediates in obtaining the compounds of the invention and their pharmaceutically acceptable acid addition salts. Salts derived from appropriate bases include alkali metal, alkaline earth metal or ammonium salts. The salt(s) must be "acceptable" in the sense of not being deleterious to the recipient thereof.

The term "Solvate" means that a compound as defined herein incorporates one or more pharmaceutically acceptable solvents including water to give rise to hydrates. The solvate may contain one or more molecules of solvent per molecule of compound or may contain one or more molecules of compound per molecule of solvent. Illustrative non-limiting examples of hydrates include monohydrate, dihydrate, trihydrate and tetrahydrate or semi-hydrate. In one embodiment, the solvent may be held in the crystal in various ways and thus, the solvent molecule may occupy lattice positions in the crystal, or they may form bonds with salts of the compounds as described herein. The solvate(s) must be "acceptable" in the sense of not being deleterious to the recipient thereof. The solvation may be assessed by methods known in the art such as Loss on Drying techniques (LOD).

It will be appreciated by those skilled in the art that the compounds in accordance with the present invention can exist in several different crystalline forms due to a different arrangement of molecules in the crystal lattice. This may include solvate or hydrate (also known as pseudopolymorphs) and amorphous forms. All such crystalline forms and polymorphs are included within the scope of the invention.

The polymorphs may be characterized by methods well known in the art. Examples of analytical procedures that may be used to determine whether polymorphism occurs include: melting point (including hot-stage microscopy), infrared (not in solution), X-ray powder diffraction, thermal analysis methods (e.g. differential scanning calorimetry (DSC) differential thermal analysis (DTA), thermogravimetric analysis (TGA)), Raman spectroscopy, comparative intrinsic dissolution rate, scanning electron microscopy (SEM).

When there is a sulfur atom present, the sulfur atom can be at different oxidation levels, ie. S, SO, or $SO_2$. All such oxidation levels are within the scope of the present invention.

When there is a nitrogen atom present, the nitrogen atom can be at different oxidation levels, ie. N or NO. All such oxidation levels are within the scope of the present invention.

In another embodiment, there is provided a compound of Table 1, or a pharmaceutically acceptable salt or solvate thereof.

TABLE 1

Compounds of Formula Ia

| No. | Compounds |
| --- | --- |
| 1 | |
| 2 | |
| 3 | |
| 4 | |

TABLE 1-continued

Compounds of Formula Ia

| No. | Compounds |
|---|---|
| 5 | (4-(1H-indazol-4-yl)pyridin-2-yl)methyl-substituted fluoro-bisphosphonic acid structure |
| 6 | (5-(1H-indazol-4-yl)pyridin-3-yl)methyl-substituted fluoro-bisphosphonic acid structure |
| 7 | (5-(1H-indazol-5-yl)pyridin-3-yl)methyl-substituted fluoro-bisphosphonic acid structure |
| 8 | (5-(1H-indazol-5-yl)pyridin-2-yl)methyl-substituted fluoro-bisphosphonic acid structure |
| 9 | (5-(1H-indazol-6-yl)pyridin-3-yl)methyl-substituted fluoro-bisphosphonic acid structure |
| 10 | (5-(3,5-dimethylisoxazol-4-yl)pyridin-3-yl)methyl-substituted fluoro-bisphosphonic acid structure |
| 11 | 3-cyano-6-(thiophen-2-yl)pyridin-2-yl aminomethylene-bisphosphonic acid structure |
| 12 | 6-phenylpyridin-2-yl aminomethylene-bisphosphonic acid structure |
| 13 | 6-(1H-indazol-5-yl)pyridin-2-yl aminomethylene-bisphosphonic acid structure |
| 14 | 4-(1H-indazol-5-yl)pyridin-2-yl aminomethylene-bisphosphonic acid structure |
| 15 | 6-(thiophen-2-yl)pyridin-2-yl aminomethylene-bisphosphonic acid structure |
| 16 | 6-(thiophen-3-yl)pyridin-2-yl aminomethylene-bisphosphonic acid structure |
| 17 | 4-phenylpyridin-2-yl aminomethylene-bisphosphonic acid structure |

TABLE 1-continued

Compounds of Formula Ia

| No. | Compounds |
|---|---|
| 18 | 4-(thiophen-3-yl)pyridin-2-yl aminomethylenebisphosphonic acid |
| 19 | 4-(thiophen-2-yl)pyridin-2-yl aminomethylenebisphosphonic acid |
| 20 | 4-(3-(trifluoromethyl)phenyl)pyridin-2-yl aminomethylenebisphosphonic acid |
| 21 | 4-(3,5-bis(trifluoromethyl)phenyl)pyridin-2-yl aminomethylenebisphosphonic acid |
| 22 | 4-(pyridin-3-yl)pyridin-2-yl aminomethylenebisphosphonic acid |
| 23 | 4-(2-methoxyphenyl)pyridin-2-yl aminomethylenebisphosphonic acid |
| 24 | 4-(3-methoxyphenyl)pyridin-2-yl aminomethylenebisphosphonic acid |
| 25 | 4-(4-methoxyphenyl)pyridin-2-yl aminomethylenebisphosphonic acid |
| 26 | 4-(naphthalen-2-yl)pyridin-2-yl aminomethylenebisphosphonic acid |
| 27 | 5-(1H-indazol-5-yl)pyridin-2-yl aminomethylenebisphosphonic acid |
| 28 | 5-phenylpyridin-2-yl aminomethylenebisphosphonic acid |
| 29 | 5-(thiophen-3-yl)pyridin-2-yl aminomethylenebisphosphonic acid |
| 30 | 3-phenylpyridin-2-yl aminomethylenebisphosphonic acid |
| 31 | 5-(1H-pyrazol-4-yl)-2-(thiophen-3-yl)pyridin-3-yl ethylidenebisphosphonic acid |
| 32 | 5-(1H-indazol-5-yl)-2-(thiophen-3-yl)pyridin-3-yl ethylidenebisphosphonic acid |

TABLE 1-continued

Compounds of Formula Ia

| No. | Compounds |
|---|---|
| 33 | 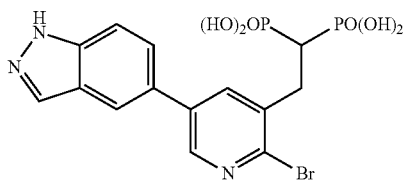 |
| 34 | 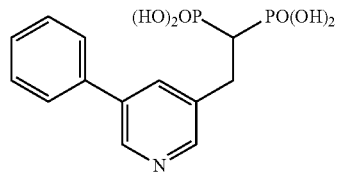 |
| 35 | 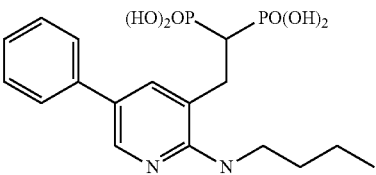 |
| 36 | 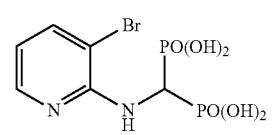 |
| 37 | 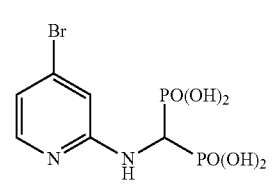 |
| 38 | 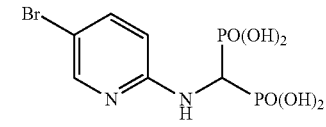 |
| 39 | 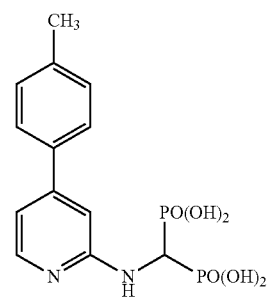 |
| 40 | 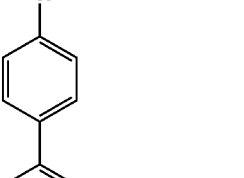 |
| 41 | 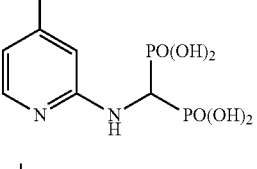 |
| 42 | 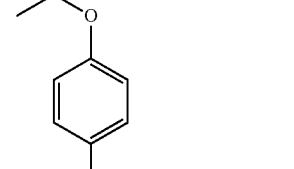 |
| 43 | 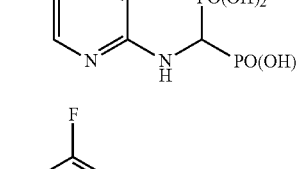 |

Abbreviations Used in the Description of the Preparation of the Compounds of the Present Disclosure:
Bu Butyl
CDCl$_3$ Deuterated chloroform
DCM Dichloromethane
DMAP N,N dimethylaminopyridine
DME 1,2-dimethoxyethane
DMEM Dulbecco's Modified Eagle Medium
DMF N,N-Dimethylformamide
DMSO Dimethyl sulfoxide
Et Ethyl
EtOAc Ethyl acetate
HMQC Heteronuclear multiple quantum coherence
mCPBA meta-chloroperbenzoic acid
HRMS High resolution mass spectrum
Me Methyl
MeOH Methanol NEt₃ Triethylamine
NFSI N-fluorobenzenesulfonimide
NMR Nuclear magnetic resonance
Ph Phenyl
RT Room temperature
THF Tetrahydrofuran
TBAF tetrabutylammonium fluoride
TFA trifluoroacetic acid
TMSBr trimethylsilyl bromide
RBF Round bottom flask Preparation of the Compounds of the Invention The compounds of the present disclosure can be prepared according to the procedures denoted in the following reaction A boronic acid-containing compound (or boronate derivative) is then coupled on the pyridine of compound 14 (X for example being Cl or Br) to obtain compound 15. Alternative synthetic methods (that are similar to the Suzuki reaction described herein) can be used to achieve a similar cross-coupling reaction using the heteroaryl halide 14 and suitable coupling fragments and catalysts, including but not limited to cross coupling reactions using Stille, Neghishi, Sonogashira and many other metal-catalyzed conditions; for a recent review article summarizing these types of reaction refer to Corbet, J.-P. and Mignani, G. *Chem. Rev.* 2006, 106, 2651-2710. The final compound 16 is obtained by subjecting product 15 to an acid or by firstly reacting compound 15 with trimethylsilyl bromide followed by methanol.

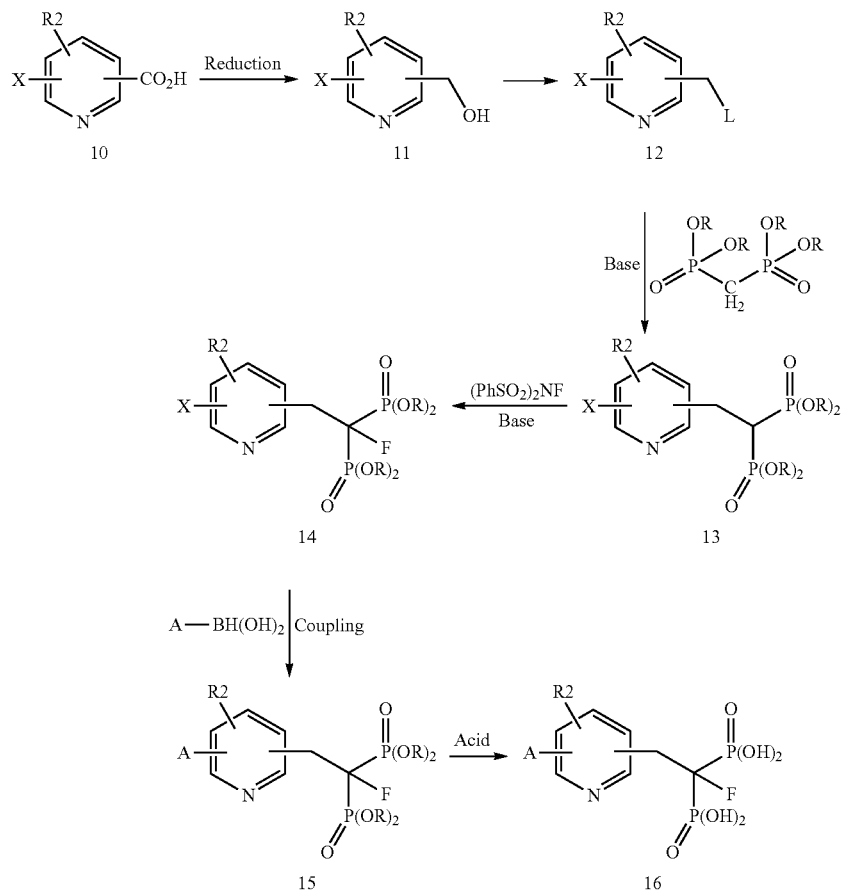

Scheme 2: General synthesis of pyridinyl fluoroethanyl bisphosphonate analogs

Schemes 2 to 4 and Examples or modifications thereof using readily available starting materials, reagents, and conventional procedures or variations thereof well-known to a practitioner of ordinary skill in the art of synthetic organic chemistry. Specific definitions of variables in the Schemes are given for illustrative purposes only and are not intended to limit the procedures described.

As illustrated in Scheme 2, reduction of the carboxylic moiety of 10 results in compound 11. Then, compound 11 is converted to obtain 12 having a leaving group L (eg. a bromide using a bromination reaction). Compound 12 is coupled with a methylene bisphonate tetraester (such as an ethyl or i-propyl tetraester) in the presence of base to produce compound 13. Compound 13 is fluorinated to form compound 14.

As illustrated in Scheme 3, pyridinylamino bisphosphonate of general formula 24 and 26 may be obtained following several different synthetic routes. For example, trimethylsilylethanone can be reacted with malononitrile to first produce 2-(1-(trimethylsilyl)ethylidene)malononitrile, as shown in Scheme 3, path (a). This intermediate can then be reacted with dimethyl cyanocarbonimidodithioate under basic conditions to give the 2-aminopyridinyl intermediate 21.

The trimethylsilyl group (which serves a protecting group at C4) may be removed with fluoride (following procedures well known in the art) to produce compound 22, the exocyclic amine protected as a bis-ter-t-butylcarbamate (Boc) and then the —SMe group displaced by an aryl or heteroaryl moiety, appropriately activated as an organo zinc reagent (as previously described by Knochel's group; *Org. Lett.* 2009, 11, 4228-4231) to obtain compounds such as 23. Hydrolysis of the Boc groups with acid (TFA) followed by reacting with a compound of general formula HPO(OR)$_2$ (such as HPO(OEt)$_2$) and HC(OEt)$_3$ gives the ester protected bisphosphonates. Finally, the desired bisphosphonic acid compound 24 is produced by subjecting the ester precursor to an acid, or by, for example, firstly reacting the ester compound with trimethylsilyl bromide followed by methanol [Scheme 3 path (a)].

A modified approach shown in Scheme 3, pathway (b), a 2-aminopyridinyl derivative compound 25, having a halo substituent can be coupled with a boronic acid-containing compound (or boronate derivative) using an appropriate catalyst, for example, Pd(PPh$_3$)$_4$ in presence of Na$_2$CO$_3$ to obtain compound 26. Alternative synthetic methods (that are similar to the Suzuki reaction described herein) can be used to achieve a similar cross-coupling reaction using the heteroaryl halide 25 and suitable coupling fragments and catalysts, including but not limited to cross coupling reactions using Stille, Negishi, Sonogashira and many other metal-catalyzed conditions; for a recent review article summarizing these types of reaction refer to Corbet, J.-P. and Mignani, G. *Chem. Rev.* 2006, 106, 2651-2710.

Scheme 3: General synthesis of pyridinylamino bisphosphonate analogs

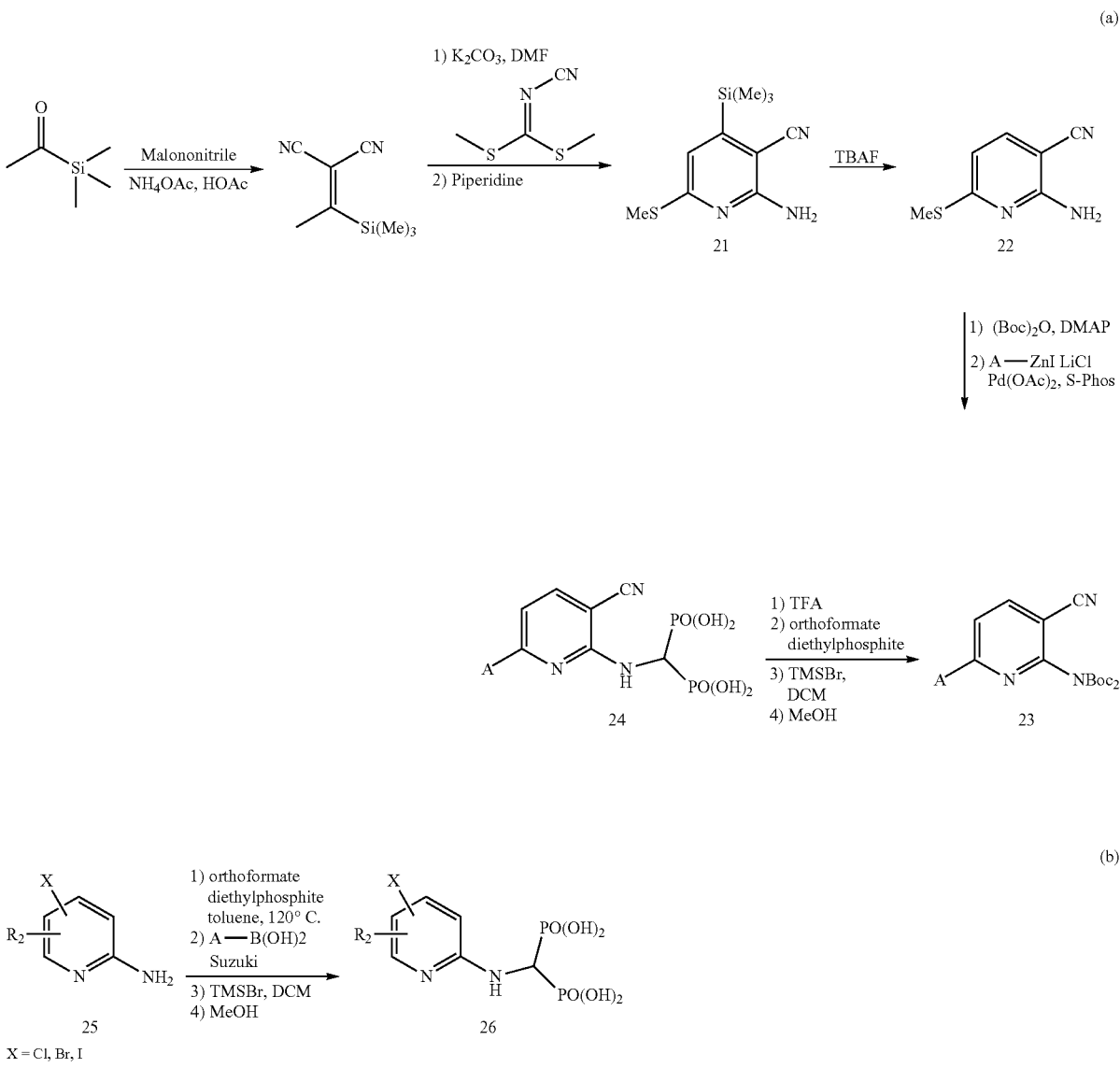

As illustrated in Scheme 4, the commercially available compound 27 can be selectively brominated by first treating with PBr₃ to give compound 28 and then with NBS and a radical initiator to give intermediate 29. The branched pyridinyl bisphosphonate of the general structures 32, 34 and 37 may then be obtained from the common intermediate 30 (prepared in the same way as shoen in Scheme 2 for the conversion of compound 12 to compound 13), following a series of reactions that can include, but are not limited to, selective reductions for the nitro group of the corresponding amine and formation of a diazonium salt which can be displaced with a halide (for example conversion of nitro intermediate 30 to the iodide intermediate 31); however, those skilled in the art of organic synthesis would realize that it can also be bromide), and subsequent metal-catalyzed cross coupling reactions with amines (e.g. Buchwald-Hartwig cross coupling to intermediate 35), boronic acid-containing compound (or boronate derivative; Suzuki reactions) using an appropriate catalyst, for example, Pd(PPh₃)₄ in presence of Na₂CO₃. Alternative synthetic methods (that are similar to the Suzuki reaction described herein) can be used to achieve a similar cross-coupling reaction using the heteroaryl halide 31, 33 and 36 and suitable coupling fragments and catalysts, including but not limited to cross coupling reactions using Suzuki, Stille, Heck, Negishi, Sonogashira and many other metal-catalyzed conditions; for a recent review article summarizing these types of reaction refer to Corbet, J.-P. and Mignani, G. *Chem. Rev.* 2006, 106, 2651-2710.

Finally, the desired bisphosphonic acid compounds 32, 34 and 37 are produced by subjecting the corresponding precursor tetraesters to an acid, or by, for example, firstly reacting the esters with trimethylsilyl bromide followed by methanol.

Scheme 4: General synthesis of selectively branched pyridinyl bisphosphonate analogs

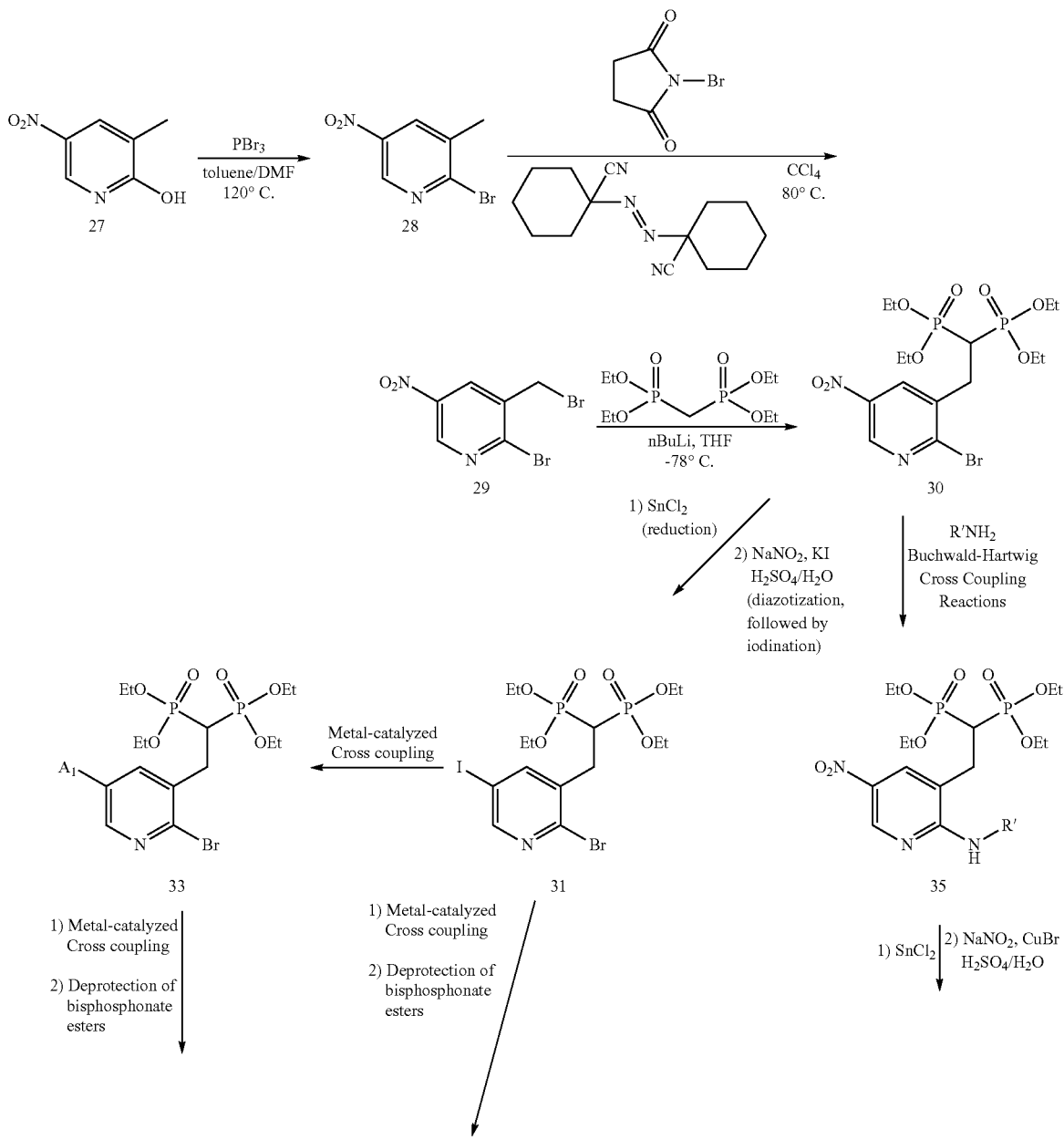

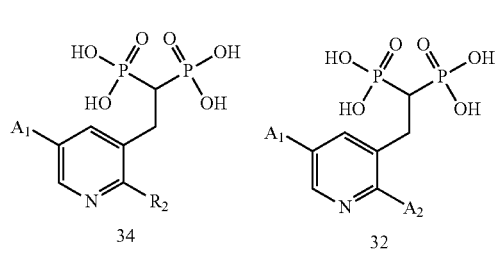
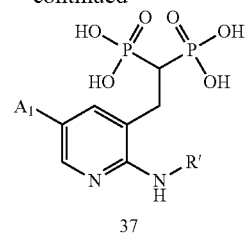
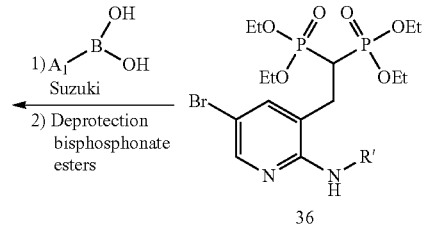

The following examples are provided to further illustrate details for the preparation and use of the compounds of the present invention. They are not intended to be limitations on the scope of the instant invention in any way, and they should not be so construed. Furthermore, the compounds described in the following examples are not to be construed as forming the only genus that is considered as the invention, and any combination of the compounds or their moieties may itself form a genus. Those skilled in the art will readily understand that known variations of the conditions and processes of the following preparative procedures can be used to prepare these compounds. All temperatures are in degrees Celsius unless noted otherwise.

Example 1

(2-(5-(1H-indazol-5-yl)pyridin-3-yl)-1-fluoroethane-1,1-diyl)diphosphonic acid, monosodium salt Step 1a: Synthesis of (5-bromopyridin-3-yl)methanol

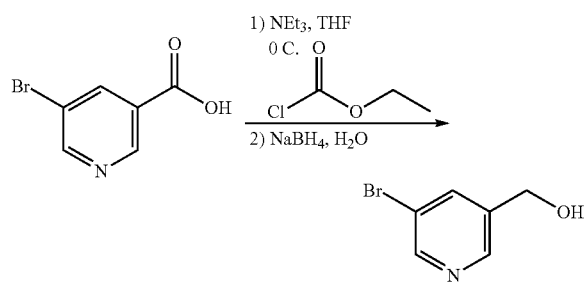

5-Bromonicotinic acid (1.00 g; 4.95 mmol) is dissolved in 30 mL anhydrous THF and triethylamine (0.76 mL; 5.44 mmol) is added by syringe, the flask is flushed with argon and cooled to 0° C. Ethylchloroformate (0.52 mL; 5.44 mmol) is then added dropwise by syringe and the mixture is stirred at RT for 60 min. The crude mixture is filtered and the residue is washed twice with 5 mL THF, the filtrate is transferred to a 100 mL RBF and cooled to 0° C. Sodium borohydride (468 mg: 12.4 mmol) is added in portions, followed by 5 mL $H_2O$ which is added dropwise via a syringe. The mixture is stirred at RT overnight and then concentrated in vacuo. The crude product is extracted 6 times with EtOAc, the organic layers are combined and dried over anhydrous sodium sulfate, concentrated in vacuo and deposited on silica. Purification by column chromatography on silica gel (pre washed with 1% $NEt_3$ in hexanes) using a solvent gradient from hexanes to EtOAc and then to 50% MeOH in EtOAc, led to the isolation of the product as a clear, colorless oil (426 mg, 46% yield).

$^1$H NMR (300 MHz, CDCl$_3$) δ 8.60 (d, J=2.2 Hz, 1H), 8.50 (s, 1H), 7.89 (s, 1H), 4.74 (d, J=5.8 Hz, 2H), 1.96 (t, J=5.7 Hz, 1H).

Step 1b: 3-bromo-5-(bromomethyl)pyridine

(5-Bromopyridin-3-yl)methanol (1.41 g; 7.5 mmol) is dissolved in 20 mL DCM and the flask is flushed with argon and cooled to 0° C. Phosphorus tribromide (0.70 mL; 7.5 mmol) is added dropwise via a syringe and reaction mixture is stirred at RT for 2 h. $NEt_3$ (1 mL) is added by syringe and the reaction mixture is stirred for 1 h. The mixture is cooled to 0° C. and quenched with the slow addition of 5 mL water, followed by the addition of 2M $K_2CO_3$ until mixture is neutral (pH=~7). The mixture is partitioned between water and EtOAc, the aqueous phase is washed three times with EtOAc and the organic layers are combined, dried over anhydrous sodium sulfate, filtered and deposited on silica. Purification by column chromatography on silica gel (pre-washed with 1% $NEt_3$) using a solvent gradient of hexanes to EtOAc led to the isolation of the desired product as white crystals (1.29 g, 69% yield).

$^1$H NMR (300 MHz, CDCl$_3$) δ 8.61 (d, J=2.2 Hz, 1H), 8.54 (d, J=2.0 Hz, 1H), 7.89 (t, J=2.1 Hz, 1H), 4.42 (s, 2H).

Step 1c: Synthesis of tetraisopropyl (2-(5-bromopyridin-3-yl)ethane-1,1-diyl)bis(phosphonate)

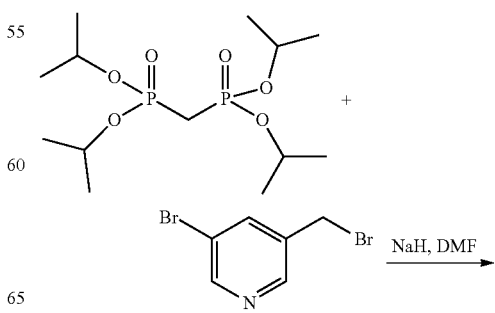

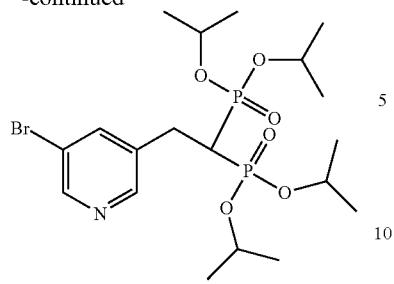
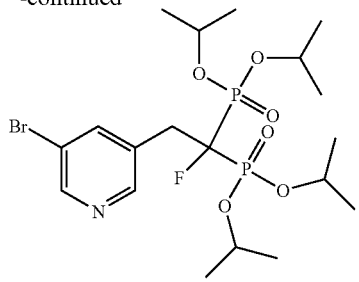

The tetra-iPr-methylene bisphonate ester (1.10 g; 3.19 mmol) is dissolved in 20 mL DMF and cooled to 0° C. NaH (153 mg; 3.83 mmol) is added in one portion and stirred at RT for 1 h. The reaction mixture is cooled to 0° C. and 3-bromo-5-(bromomethyl)pyridine (800 mg; 3.19 mmol) is added by syringe as a solution in 10 mL DMF. The reaction mixture is stirred overnight. The mixture is then diluted with DCM and quenched with 5 mL of saturated NH$_4$Cl solution. The layers are separated and the aqueous layer is extracted twice with DCM. The combined organic layers are dried over anhydrous magnesium sulfate and evaporated to dryness. The residue is redissolved in EtOAc and washed five times with water and once with brine. The organic layers are dried over magnesium sulfate and evaporated to dryness. Purification by column chromatography on silica gel using a solvent gradient from hexanes to EtOAc and then to 10% MeOH in EtOAc let to the isolation of the product (912 mg) contaminated with 27% of starting material (estimated by $^{31}$P-NMR). The crude product is redissolved in EtOAc and extracted five times with 1M HCl. The combined aqueous layers are neutralized with sodium bicarbonate and washed three times with DCM. The combined DCM layers are dried over anhydrous magnesium sulfate and evaporated to dryness to obtain the product as a colorless oil (776 mg, still contaminated with ~6% starting bisphosphonate; a yield of 47% is estimated based on $^{31}$P-NMR).

$^1$H NMR (300 MHz, CDCl$_3$) δ 8.52 (d, J=2.0 Hz, 1H), 8.43 (s, 1H), 7.79 (t, J=2.0 Hz, 1H), 4.77 (m, 4H), 3.19 (td, J=16.1, 6.4 Hz, 2H), 2.43 (ddd, J=23.9, 20.7, 5.8 Hz, 1H), 1.42-1.18 (m, 24H). $^{31}$P NMR (81 MHz, CDCl$_3$) δ 17.57.

Step 1d: Synthesis of tetraisopropyl (2-(5-bromopyridin-3-yl)-1-fluoroethane-1,1-diyl)bis(phosphonate)

Tetraisopropyl (2-(5-bromopyridin-3-yl)ethane-1,1-diyl)bis(phosphonate) (1.19 g; 2.31 mmol) is dissolved in 40 mL THF and cooled to −78° C. n-BuLi (1.6 M in hexanes; 1.59 mL; 2.54 mmol) is added via a syringe, the solution is stirred for 10 min at −78° C., for 1 h at 0° C. The mixture is cooled back to −78° C. and NFSI (800 mg; 2.58 mmol, predissolved in 5 mL THF and cooled to 0° C.) is added dropwise via syringe. The reaction mixture is stirred at −78° C. for 10 min and left to stir overnight. The reaction mixture is quenched with 1 mL of saturated NH$_4$Cl, and concentrated in vacuo. The residue is redissolved in EtOAc, washed three times with water and once with brine, dried over anhydrous magnesium sulfate and evaporated to dryness. Purification by column chromatography on silica gel using a solvent gradient from hexanes to EtOAc and then to 10% MeOH in EtOAc led to the isolation of pure product as a pale brown oil (790 mg; 73% yield based on recovered starting material).

$^1$H NMR (300 MHz, CDCl$_3$): δ 8.55 (d, J=2.1 Hz, 1H), 8.43 (s, 1H), 7.81 (s, 1H), 4.82 (m, 4H), 3.57-3.27 (m, 2H), 1.29 (m, 24H).

$^{13}$C NMR (126 MHz, CDCl$_3$) δ 150.13 (s), 148.96 (s), 141.23 (s), 132.21 (t, J=8.1 Hz), 119.74 (s), 94.21 (dt, J=192.9, 157.7 Hz), 73.06 (dt, J=61.8, 3.4 Hz), 35.70 (d, J=19.4 Hz), 24.24 (d, J=31.7 Hz), 23.63 (dt, J=45.3, 3.0 Hz).

$^{19}$F NMR (470 MHz, CDCl$_3$) δ −192.85 (tt, J=74.5, 26.7 Hz).

$^{31}$P NMR (81 MHz, CDCl$_3$) δ 9.25 (d, J=74.6 Hz).

Step 1e: Synthesis of tetraisopropyl (2-(5-(1H-indazol-5-yl)pyridin-3-yl)-1-fluoroethane-1,1-diyl)bis(phosphonate)

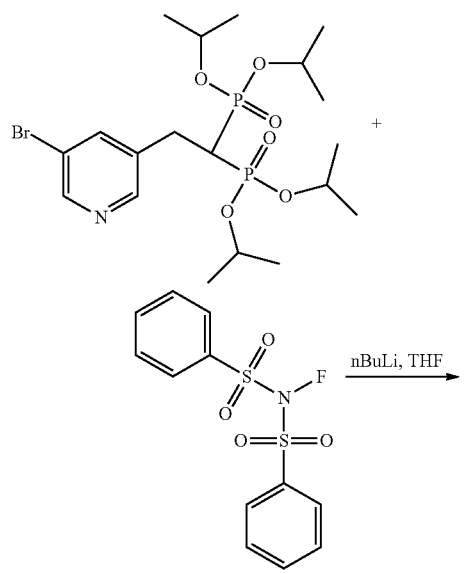

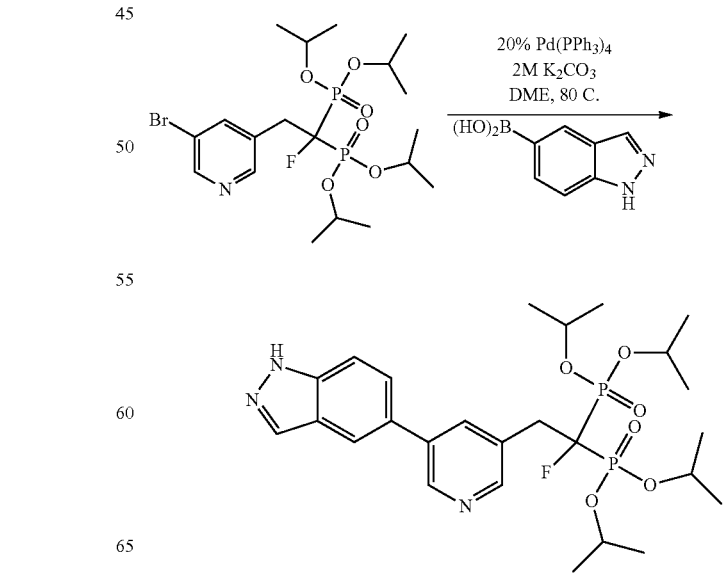

Tetraisopropyl (2-(5-bromopyridin-3-yl)-1-fluoroethane-1,1-diyl)bis(phosphonate) (85 mg; 0.16 mmol), Pd(PPh$_3$)$_4$ (36.9 mg; 0.032 mmol) and (1H-indazol-5-yl)boronic acid (39 mg; 0.24 mmol) are added to the vial and the vial is capped with a septum. DME (4 mL) is added and the vial is flushed with argon, an aqueous solution of potassium carbonate (2.5 eq.) is added and the mixture is flushed again with argon. The reaction mixture is stirred at 80° C. for 36 h under an atmosphere of argon. The mixture was cooled to RT, diluted with EtOAc and filtered through Celite™, the Celite™ is washed three times with EtOAc/MeOH (1:1). The filtrate is deposited on silica gel and purified by column chromatography (on pre washed silica with 1% NEt$_3$ in hexanes) using a solvent gradient from hexanes to EtOAc and then to 50% MeOH in EtOAc. The pure product is isolated as a brown oil (41 mg, 45% yield).

$^1$H NMR (300 MHz, CDCl$_3$) δ 8.77 (d, J=2.2 Hz, 1H), 8.50 (s, 1H), 8.15 (s, 1H), 7.95 (s, 1H), 7.92 (s, 1H), 7.61 (s, 2H), 4.84 (m, 4H), 3.69-3.44 (m, 2H), 1.43-1.13 (m, 24H).

$^{31}$P NMR (81 MHz, CDCl$_3$) δ 9.54 (d, J=74.8 Hz).

Step 1f: Synthesis of (2-(5-(1H-indazol-5-yl)pyridin-3-yl)-1-fluoroethane-1,1-diyl)diphosphonic acid, monosodium salt

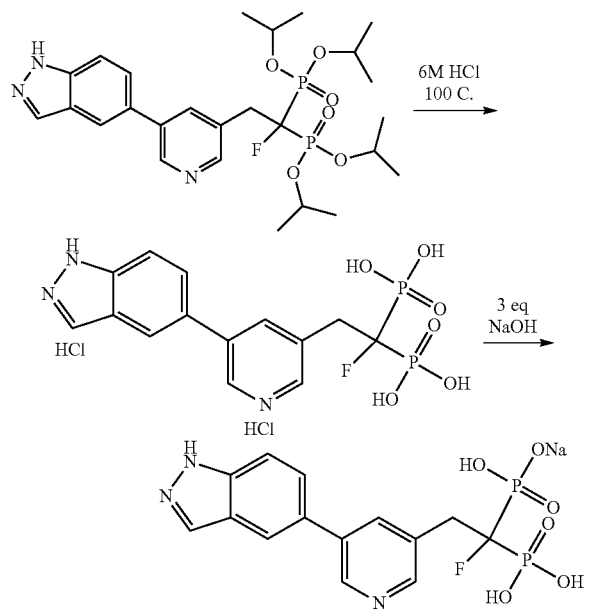

Tetraisopropyl (2-(5-(1H-indazol-5-yl)pyridin-3-yl)-1-fluoroethane-1,1-diyl)bis(phosphonate) (41 mg; 0.72 mmol) is transferred to a pressure vessel and 4 mL of 6M HCl is added. The reaction mixture is stirred overnight at 105° C. The crude is cooled to RT, filtered through a small cotton plug, concentrated in vacuo and lyophilized to dryness to obtain 25.0 mg (0.053 mmol) of the bis-HCl salt. To this solid, 0.5 μL of deionized water is added followed by the addition 3 equivalents of NaOH (3×51 μL of 1.030 M NaOH solution). The solution is purified by C$^{18}$ reversed phase chromatography, and lyophilized to give a white powder of the monosodium salt containing 2 equivalents of NaCl (23.4 mg; 60% yield).

$^1$H NMR (500 MHz, D$_2$O) δ 8.34 (s, 1H), 8.24 (s, 1H), 7.95 (s, 1H), 7.94 (s, 1H), 7.81 (s, 1H), 7.47 (dd, J=26.9, 8.7 Hz, 2H), 3.41-3.28 (m, 2H).

$^{13}$C NMR (126 MHz, D$_2$O) δ 149.01 (s), 143.57 (s), 142.80 (s), 138.17 (s), 135.60 (s), 135.02-134.83 (m), 134.42 (s), 129.36 (s), 125.40 (s), 123.16 (s), 118.91 (s), 112.30 (s), 99.63 (dt, J=177.2, 136.0 Hz), 36.64 (d, J=18.1 Hz).

{$^{19}$F, $^{13}$C} HMQC NMR (470 MHz, D$_2$O) δ −185 correlates with 99

$^{31}$P NMR (81 MHz, D$_2$O) δ 12.86 (d, J=66.7 Hz).

$^{19}$F NMR (470 MHz, D$_2$O) δ −184.77--185.26 (m).

HRMS (ESI$^-$): calcd 400.02691 (C$_{14}$H$_{13}$O$_6$N$_3$FP$_2$), found (m/z) 400.02650 [M−H+]$^-$ Example 2

Synthesis of (2-(5-(3,5-dimethylisoxazol-4-yl)pyridin-3-yl)-1-fluoroethane-1,1-diyl)diphosphonic acid Step 2a: Synthesis of tetraisopropyl (2-(5-(3,5-dimethylisoxazol-4-yl)pyridin-3-yl)-1-fluoroethane-1,1-diyl)bis(phosphonate)

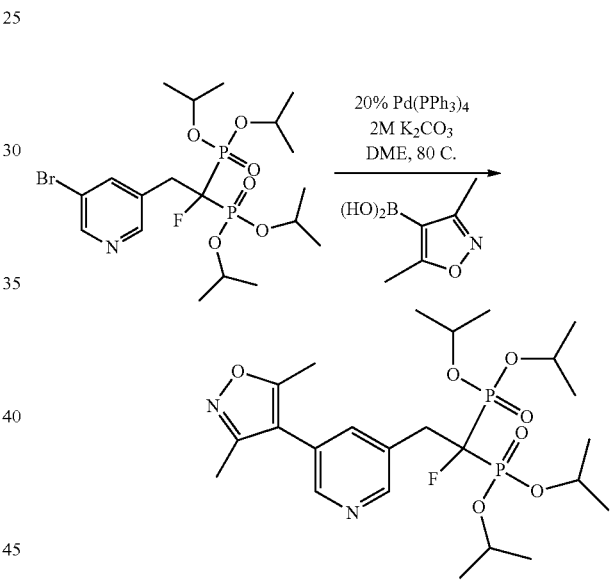

The synthesis of the starting material for this step, tetraisopropyl (2-(5-bromopyridin-3-yl)-1-fluoroethane-1,1-diyl)bis(phosphonate), is described in Example 1, Step 1a-d.

A sample of tetraisopropyl (2-(5-bromopyridin-3-yl)-1-fluoroethane-1,1-diyl)bis(phosphonate) (85 mg; 0.16 mmol), Pd(Ph$_3$)$_4$ (36.9 mg; 0.032 mmol) and (3,5-dimethylisoxazol-4-yl)boronic acid (34 mg; 0.24 mmol) are added in a vial, the vial is capped with a septum and added DME (4 mL) is added. The mixture is immediately flushed with argon, potassium carbonate solution (2.5 eq.) is added and flushed again with argon. The reaction mixture is stirred at 80° C. for 36 h under argon. The mixture is cooled, diluted with EtOAc and filtered through Celite™, the Celite™ is rinsed 3× with EtOAc/MeOH (1:1). The combined filtrate is concentrated under vacuum and deposited on silica gel. Purification by column chromatography on silica gel (pre washed with 1% NEt$_3$ in hexanes) using a solvent gradient from hexanes to EtOAc, and then to 50% MeOH in EtOAc lead to the isolation of the product as a brown oil (41 mg; 47% yield).

¹H NMR (300 MHz, CDCl₃) δ 8.53 (s, 1H), 8.42 (d, J=2.2 Hz, 1H), 7.57 (s, 1H), 4.95-4.73 (m, 4H), 3.61-3.35 (m, 2H), 2.44 (s, 3H), 2.30 (s, 3H), 1.42-1.10 (m, 24H).

³¹P NMR (81 MHz, CDCl₃) δ 9.46 (d, J=74.2 Hz).

Step b: Synthesis of (2-(5-(3,5-dimethylisoxazol-4-yl)pyridin-3-yl)-1-fluoroethane-1,1-diyl)diphosphonic acid, monosodium salt

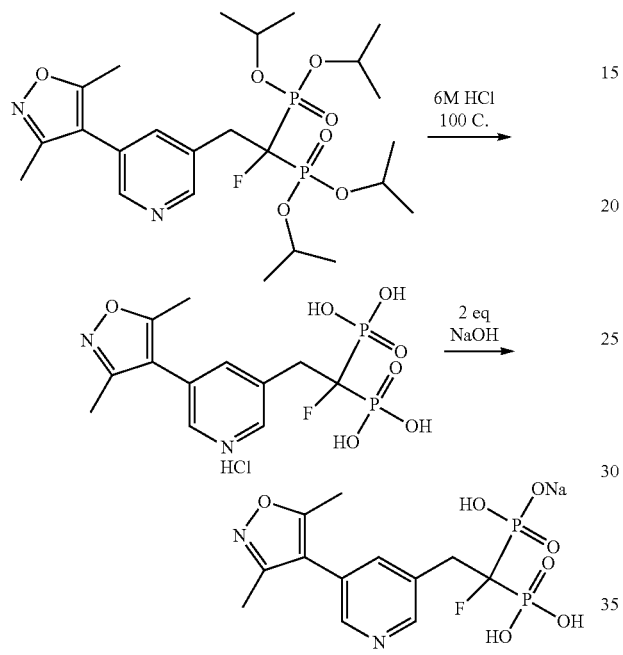

A sample of tetraisopropyl (2-(5-(3,5-dimethylisoxazol-4-yl)pyridin-3-yl)-1-fluoroethane-1,1-diyl)bis(phosphonate) (41 mg; 0.75 mmol) and 4 mL 6M HCl are transferred into a pressure vessel and stirred overnight at 105° C. The reaction mixture is cooled, filtered through a small cotton plug, and partly concentrated (to remove excess HCl) under vacuum. The crude product is lyophilized to dryness to obtain 26.7 mg (0.075 mmol) of the mono-HCl salt. The solid sample is suspended in deionized water (500 μL) and 2 equivalents of NaOH are added (2×62 μL of a 1.030 M solution). The sample is purified by C18 reversed phase chromatography and lyophilized to give the final product as a white powder that contained 1 equivalent of NaCl (25.5 mg; 74% yield).

¹H NMR (500 MHz, D₂O) δ 8.39 (s, 1H), 8.24 (d, J=1.9 Hz, 1H), 7.85 (s, 1H), 3.38 (dt, J=16.1, 11.7 Hz, 2H), 2.27 (s, 3H), 2.11 (s, 3H).

¹³C NMR (75 MHz, D₂O) δ 167.30 (s), 160.15 (s), 150.12 (s), 145.34 (s), 140.45 (s), 135.21-134.94 (m), 125.03 (s), 113.49 (s), 36.40 (d, J=18.2 Hz), 10.66 (s), 9.69 (s).

{¹⁹F, ¹³C} HMQC NMR (470 MHz, D₂O) δ −185 correlates with 99

³¹P NMR (81 MHz, D₂O) δ 14.02 (d, J=66.3 Hz).

¹⁹F NMR (470 MHz, D₂O) δ −184.88-−185.55 (m).

HRMS (ESI⁻): calcd 379.02658 (C₁₂H₁₄O₇N₂FP₂), found (m/z) 379.02674 [M−H⁺]⁻

Example 3

(2-(5-(1H-pyrazol-4-yl)pyridin-3-yl)-1-fluoroethane-1,1-diyl)diphosphonic acid, monosodium salt Step 3a: Synthesis of tetraisopropyl (2-(5-(1H-pyrazol-4-yl)pyridin-3-yl)-1-fluoroethane-1,1-diyl)bis(phosphonate)

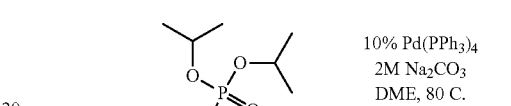

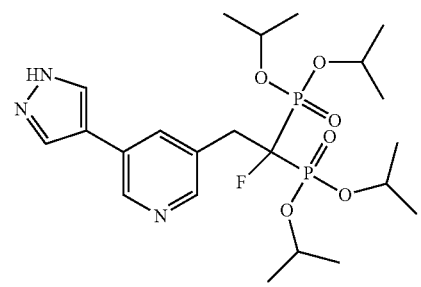

The synthesis of the starting material for this step, tetraisopropyl (2-(5-bromopyridin-3-yl)-1-fluoroethane-1,1-diyl)bis(phosphonate), is described in Example 1, Step 1a-1d.

A sample of this aryl bromide (85 mg; 0.16 mmol) is mixed with Pd(PPh₃)₄ (18 mg; 0.016 mmol) and 1H-pyrazole-4-boronic acid (39 mg; 0.35 mmol). The flask is capped with a septum and carefully flushed with argon. DME (4 mL) is added and the vial is flushed again with argon. Finally, sodium carbonate solution (0.20 mL; 2M) is added and the mixture is flushed again with argon. The reaction mixture is stirred at 80° C. overnight under an atmosphere of argon, then cooled to RT, diluted with EtOAc and filtered through Celite™, the Celite™ is rinsed 3× with EtOAc/MeOH (1:1). The filtrate is deposited on silica and purified by column chromatography on silica gel (pre washed with 1% NEt₃ in hexanes) using a solvent gradient from hexanes to EtOAc and then to 50% MeOH in EtOAc. The product is isolated as a brown oil (56 mg; 68% yield).

¹H NMR (500 MHz, CDCl₃) δ 8.67 (d, J=2.1 Hz, 1H), 8.41 (s, 1H), 7.89 (s, 2H), 7.77 (s, 1H), 4.90-4.74 (m, 4H), 3.56-3.42 (m, 2H), 1.29 (m, 24H).

³¹P NMR (81 MHz, CDCl₃) δ 9.52 (d, J=74.7 Hz).

Step 3b: Synthesis of (2-(5-(1H-pyrazol-4-yl)pyridin-3-yl)-1-fluoroethane-1,1-diyl)diphosphonic acid, monosodium salt

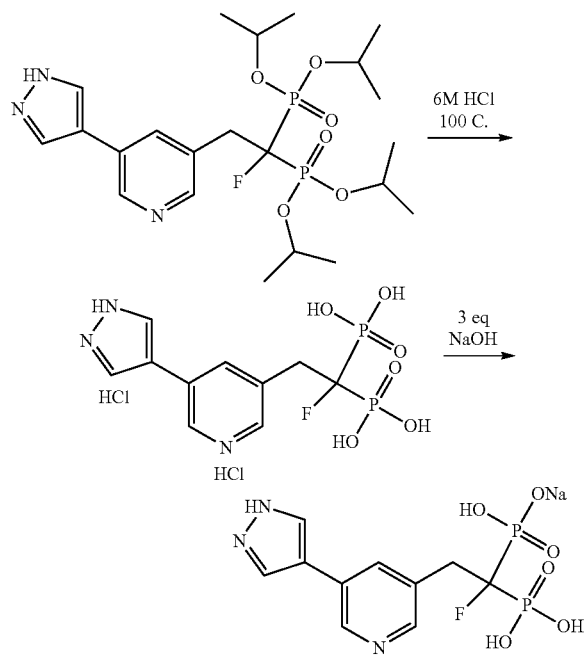

Tetraisopropyl (2-(5-(1H-pyrazol-4-yl)pyridin-3-yl)-1-fluoroethane-1,1-diyl)bis(phosphonate) (56 mg; 0.11 mmol) is transferred to pressure vessel, 4 mL 6M HCl is added and the mixture is stirred overnight at 105° C. The mixture is cooled to RT, filtered through a small cotton plug, concentrating under vacuum and lyophilized to dryness to give 36.8 mg (0.084 mmol) of the product as the bis-HCl salt. The sample is suspended and 0.5 mL of deionized water and 3 equivalents of NaOH (3×84 µL of 1.030 M NaOH solution) are added. The solution is purified by C18 reversed phase chromatography, and lyophilized to give a white powder of the monosodium salt (36.3 mg; 69% yield; sample contained 2 equivalents of NaCl).

$^1$H NMR (500 MHz, D$_2$O) δ 8.35 (d, J=1.7 Hz, 1H), 8.22 (s, 1H), 7.92 (s, 2H), 7.91 (s, 1H), 3.33 (dt, J=23.5, 11.8 Hz, 2H).

$^{13}$C NMR (126 MHz, D$_2$O) δ 148.64 (s), 142.23 (s), 136.58 (s), 135.22-135.02 (m, J=6.5, 3.4 Hz), 132.24 (s), 127.50 (s), 118.30 (s), 99.56 (dt, J=177.8, 136.1 Hz), 36.55 (d, J=18.2 Hz).

{$^{19}$F, $^{13}$C} HMQC NMR (470 MHz, D$_2$O) δ −185 correlates with 99

$^{31}$P NMR (81 MHz, D$_2$O) δ 14.02 (d, J=66.3 Hz).

$^{19}$F NMR (470 MHz, D$_2$O) δ −185.11 (tt, J=66.6, 26.2 Hz).

HRMS (ESI$^-$): calcd 350.01126 (C$_{10}$H$_{11}$O$_6$N$_3$FP$_2$), found (m/z) 350.01134 (M−H$^+$)$^-$ Example 4

Synthesis of (2-(2-(1H-indazol-4-yl)pyridin-4-yl)-1-fluoroethane-1,1-diyl)diphosphonic acid Step 4a: Synthesis of (2-chloropyridin-4-yl)methanol

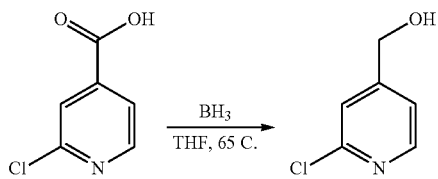

2-Chloroisonicotinic acid (2.0 g; 12.7 mmol) is dissolved in 25 mL THF under anhydrous conditions and borane (1.0 M in THF; 25.4 ml; 25.4 mmol) is added drop wise via a syringe. The solution is stirred overnight at 50° C. The mixture is cooled to RT and quenched with 5 mL MeOH, concentrated under reduced pressure and purified by column chromatography on silica gel using a solvent gradient of hexanes to EtOAc. The final product is isolated as a white powder (1.1 g, 60% yield).

$^1$H NMR (300 MHz, CDCl$_3$): δ 8.34 (d, J=5.1 Hz, 1H), 7.36 (dq, J=1.6, 0.8 Hz, 1H), 7.22-7.19 (m, 1H), 4.75 (s, 2H).

Step 4b: Synthesis of 4-(bromomethyl)-2-chloropyridine

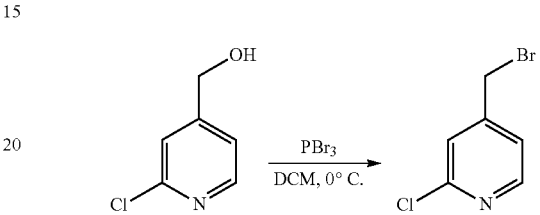

(2-chloropyridin-4-yl)methanol (1.1 g, 7.3 mmol) is dissolved in 20 mL DCM; flushed with argon and cooled to 0° C. PBr$_3$ (0.76 mL; 8.1 mmol) is added drop wise via a syringe (solution turned cloudy) and reaction mixture is stirred at RT for 3 h. Cooled to 0° C. and quenched with 5 mL water. The reaction mixture is adjusted to pH 7 by the addition of 2M K$_2$CO$_3$. The aqueous and organic layer are separated and the aqueous layer is extracted 3× with EtOAc. The organic layers are combined, dried over anhydrous sodium sulfate, filtered and deposited on silica. Column chromatography on silica gel (pre-washed with 1% NEt$_3$), using a solvent gradient from hexanes to EtOAc lead to the isolation of the product as pale pink crystals (700 mg, 50% yield based on recovered starting material).

$^1$H NMR (300 MHz, CDCl$_3$) δ 8.37 (d, J=5.1 Hz, 1H), 7.35 (s, 1H), 7.27-7.20 (m, 1H), 4.35 (s, 2H).

Step 4c: Synthesis of tetraisopropyl (2-(2-chloropyridin-4-yl)ethane-1,1-diyl)bis(phosphonate

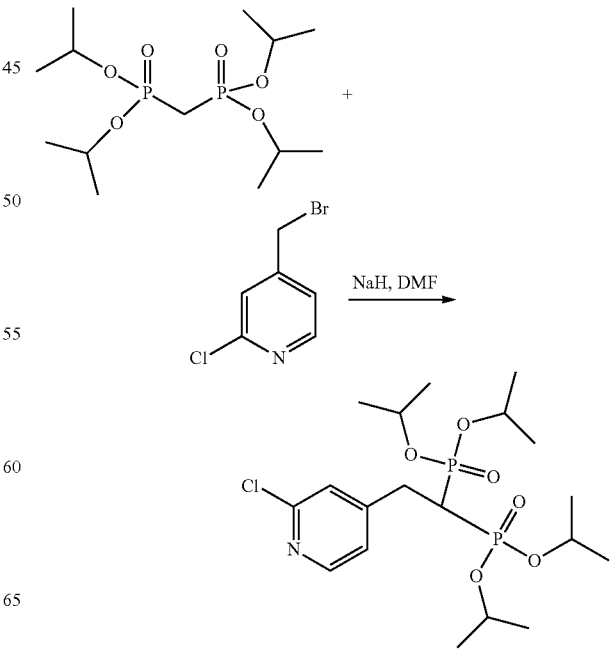

Tetra-iPr-methylene bisphosphonate ester (1.2 g; 3.4 mmol) is dissolved in 20 mL DMF and cooled to 0° C. NaH (150 mg; 3.73 mmol) is added in one portion and stirred at RT for 1 h. The reaction mixture is cooled to 0° C. and 4-(bromomethyl)-2-chloropyridine (700 mg: 3.4 mmol) is transferred with a syringe as a solution in 10 mL DMF. The reaction mixture is stirred overnight. The reaction mixture is quenched by drop wise addition of MeOH, concentrated in vacuo and redissolved in 60 mL EtOAc. Washed three times with water and once with brine, dried over sodium sulfate and deposited on silica. Purification by column chromatography on silica gel (pre washed with 1% NEt$_3$ in hexanes) using a solvent gradient from hexanes to EtOAc and then to 50% MeOH in EtOAc lead to the isolation of the product as a pale yellow oil (979 mg, 57% estimated yields of pure product) contaminated with approximately 6.5% starting bisphosphonate (estimated by $^{31}$P-NMR).

$^1$H NMR (300 MHz, CDCl$_3$) δ 8.27 (d, J=5.1 Hz, 1H), 7.26 (m, 1H), 7.15 (d, J=5.1 Hz, 1H), 4.77 (m, 4H), 3.17 (td, J=16.3, 6.4 Hz, 2H), 2.46 (tt, J=23.9, 6.4 Hz, 1H), 1.41-1.20 (m, 24H). $^{31}$P NMR (81 MHz, CDCl$_3$) δ 17.77.

Step 4d: Synthesis of tetraisopropyl (2-(2-chloropyridin-4-yl)-1-fluoroethane-1,1-diyl)bis(phosphonate)

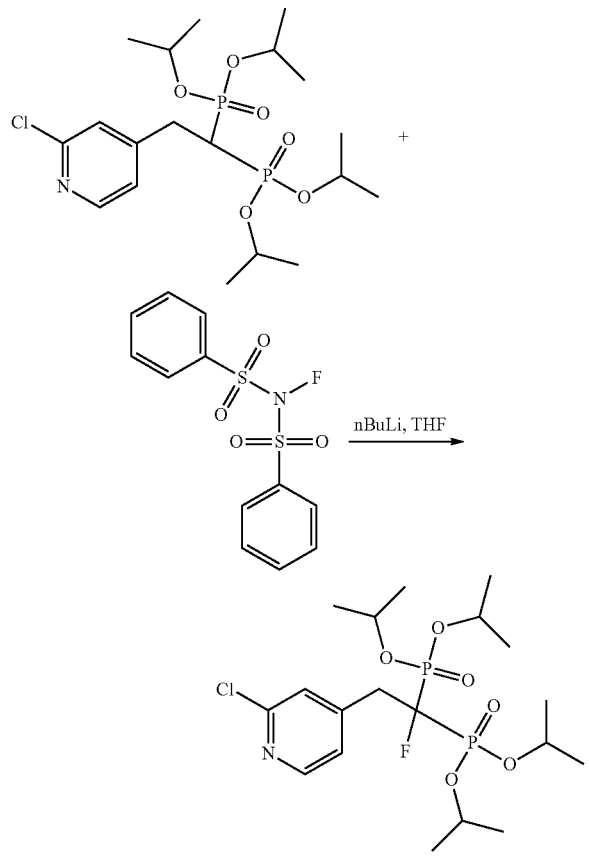

The semi-pure product from Step 4c is dissolved in 50 mL THF and cooled to −78° C. nBuLi (1.6 M in hexanes; 1.60 mL; 2.56 mmol) is added via a syringe and the solution is stirred for 1 h at −78° C. In a vial NFSI (740 mg; 2.35 mmol) is predissolved in 5 mL THF and added dropwise via syringe to the reaction mixture. The reaction mixture is stirred at −78° C. for 10 min and left to stir for 6 h, without replenishing of the cold bath. The reaction mixture is then quenched with 1 mL MeOH, concentrated in vacuo, redissolved in 100 mL EtOAc and washed three times with water and once with brine; dried over sodium sulfate and deposited on silica. Purification by column chromatography using a solvent gradient from hexanes to EtOAc and then to 10% MeOH in EtOAc, led to the isolation 746 mg (79% yield) of the product as a brown oil.

$^1$H NMR (300 MHz, CDCl$_3$) δ 8.27 (dd, J=5.1, 0.5 Hz, 1H), 7.31 (s, 1H), 7.18 (dt, J=5.1, 1.2 Hz, 1H), 4.92-4.73 (m, 4H), 3.52-3.28 (m, 2H), 1.41-1.18 (m, 24H).

$^{13}$C NMR (75 MHz, CDCl$_3$) δ 150.75 (s), 148.66 (s), 146.99 (td, J=8.5, 1.2 Hz), 126.98 (d, J=1.5 Hz), 125.35 (d, J=1.3 Hz), 94.00 (dt, J=194.2, 157.8 Hz), 73.12 (dt, J=40.1, 3.4 Hz), 37.76 (d, J=18.9 Hz), 24.19 (d, J=20.3 Hz), 23.57 (dt, J=28.1, 3.0 Hz).

$^{19}$F NMR (470 MHz, CDCl$_3$) δ −192.79 (tt, J=74.0, 26.2 Hz). $^{31}$P NMR (81 MHz, CDCl$_3$) δ 9.09 (d, J=74.2 Hz).

Step 4e: Synthesis of tetraisopropyl (2-(2-(1H-indazol-4-yl)pyridin-4-yl)-1-fluoroethane-1,1-diyl)bis(phosphonate)

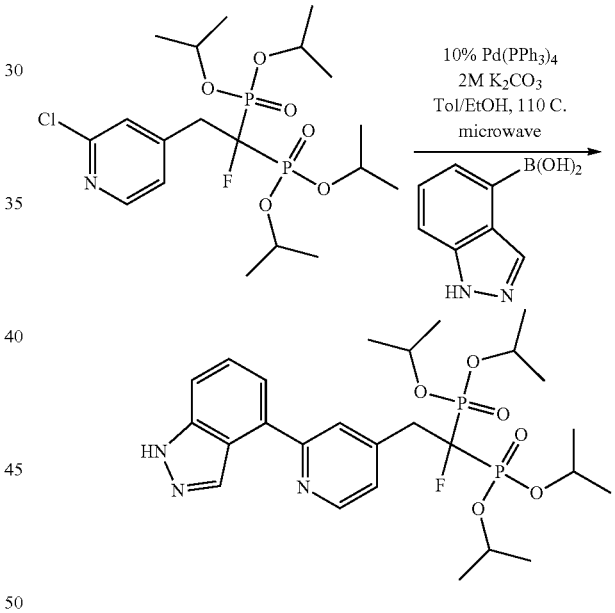

Tetraisopropyl (2-(2-chloropyridin-4-yl)-1-fluoroethane-1,1-diyl)bis(phosphonate) (78 mg; 0.16 mmol), Pd(PPh$_3$)$_4$ (37 mg; 0.032 mmol) and (1H-indazol-4-yl)boronic acid (52 mg; 0.32 mmol) are mixed in microwave vial (2-5 mL). The vial is capped with a septum, 2.0 mL of DME is added and the reaction mixture is immediately flushed with argon. Sodium carbonate solution (0.20 mL; 2M) is added and the mixture is flushed again with argon. The vial is re-capped with Teflon cap and irradiated in microwave for 15 min at 110° C. The mixture is cooled, diluted with EtOAc and filtered through Celite™, the Celite™ is rinsed 3× with EtOAc/MeOH (1:1). The filtrates are concentrated and deposited on silica. Purification by column chromatography on silica gel (pre treated with 1% NEt$_3$ in hexanes) using a solvent gradient from hexanes to EtOAc, and then to 50% MeOH in EtOAc lead to the isolation of the product as a yellow oil (28 mg; 31% yield).

$^{1}$H NMR (400 MHz, CDCl$_{3}$) δ 8.70-8.64 (m, 2H), 7.85 (s, 1H), 7.61 (d, J=7.1 Hz, 1H), 7.55 (d, J=8.0 Hz, 1H), 7.51-7.43 (m, 1H), 7.28 (d, J=5.0 Hz, 1H), 4.93-4.71 (m, 4H), 3.64-3.44 (m, 2H), 1.46-1.15 (m, 24H). $^{31}$P NMR (81 MHz, CDCl$_{3}$) δ 9.30 (d, J=73.3 Hz).

Step 4f: Synthesis of (2-(2-(1H-indazol-4-yl)pyridin-4-yl)-1-fluoroethane-1,1-diyl)diphosphonic acid, monosodium salt

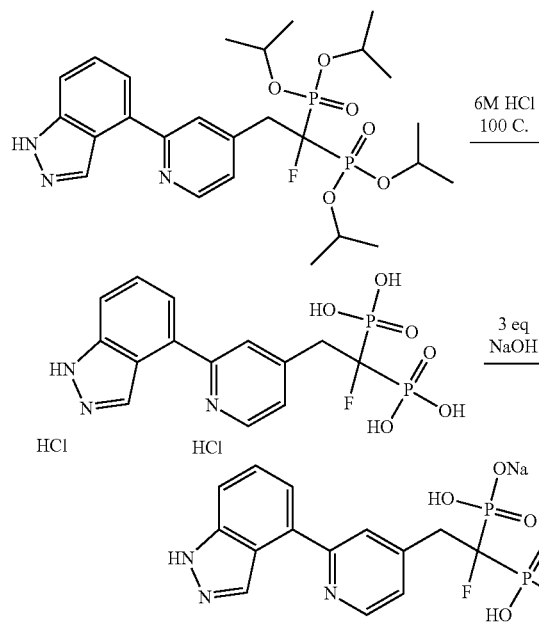

Tetraisopropyl (2-(2-(1H-indazol-4-yl)pyridin-4-yl)-1-fluoroethane-1,1-diyl)bis(phosphonate) (40 mg; 0.070 mmol) and 4 mL 6M HCl are transferred to a pressure vessel and stirred overnight at 105° C. The mixture is cooled, filtered through a small cotton plug and the excess water and HCl is removed under vacuum. The sample is lyophilized to dryness to give a solid of 28.6 mg (0.060 mmol) of bis-HCl salt. The sample is suspended in water (500 μL), three equivalents of NaOH (3×59 μL of 1.030 M solution) are added and purified by C18 reversed phase chromatography. The monosodium salt is isolated as a white powder, containing 2 equivalents of NaCl (29 mg; 76% yield).

$^{1}$H NMR (500 MHz, D$_{2}$O) δ 8.32 (d, J=5.3 Hz, 1H), 8.13 (s, 1H), 7.70 (s, 1H), 7.48 (d, J=8.3 Hz, 1H), 7.40 (d, J=5.5 Hz, 1H), 7.36-7.25 (m, 2H), 3.46-3.31 (m, 2H).

$^{13}$C NMR (75 MHz, D$_{2}$O) δ 155.12 (s), 150.67 (td, J=6.7, 3.7 Hz), 147.34 (s), 141.87 (s), 133.92 (s), 132.70 (s), 126.59 (s), 126.42 (s), 126.28 (s), 120.41 (s), 120.19 (s), 111.54 (s), 99.71 (dt, J=179.5, 135.9 Hz), 39.08 (d, J=18.8 Hz).

{$^{19}$F, $^{13}$C} HMQC NMR (470 MHz, D$_{2}$O) δ −185 correlates with 99

$^{31}$P NMR (81 MHz, D$_{2}$O) δ 13.92 (d, J=66.0 Hz).

$^{19}$F NMR (470 MHz, D$_{2}$O) δ −185.08 (tt, J=66.1, 23.9 Hz).

HRMS (ESI$^{-}$): calcd 400.02691 (C$_{14}$H$_{13}$O$_{6}$N$_{3}$FP$_{2}$), found (m/z) 400.02672 [M−H+]$^{-}$.

The following compounds have been prepared in a manner similar to that of the examples above.

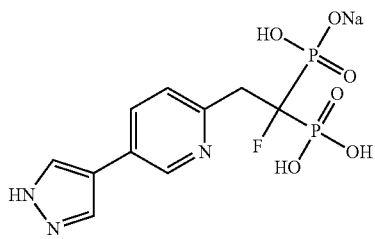

$^{1}$H NMR (500 MHz, D$_{2}$O) δ 8.36 (d, J=1.8 Hz, 1H), 8.19 (s, 1H), 7.88 (s, 2H), 7.83 (s, 1H), 3.29 (dt, J=23.5, 11.5 Hz, 2H).

$^{13}$C NMR (75 MHz, D$_{2}$O) δ 143.57 (s), 133.14 (s), 133.01 (s), 126.88 (s), 126.41 (s), 117.95 (s), 40.84 (d, J=17.2 Hz).

{$^{19}$F, $^{13}$C} HMQC NMR (470 MHz, D$_{2}$O) δ −186 correlates with 99

$^{31}$P NMR (81 MHz, D$_{2}$O) δ 13.65 (d, J=65.9 Hz).

$^{19}$F NMR (470 MHz, D$_{2}$O) δ −185.79--186.24 (m).

HRMS (ESI$^{-}$): calcd 350.01126 (C$_{10}$H$_{11}$O$_{6}$N$_{3}$FP$_{2}$), found (m/z) 350.01147 [M−H+]$^{-}$

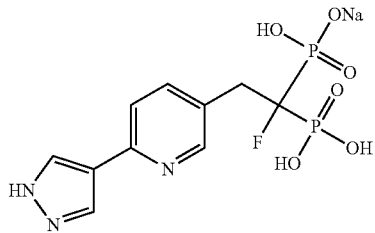

$^{1}$H NMR (500 MHz, D$_{2}$O) δ 8.25 (s, 1H), 7.96 (s, 2H), 7.71 (d, J=7.9 Hz, 1H), 7.42 (d, J=8.2 Hz, 1H), 3.48 (s, 1H), 3.33-3.17 (m, 2H).

$^{13}$C NMR (126 MHz, D$_{2}$O) δ 168.26 (s), 150.46 (s), 149.09 (s), 141.02 (s), 135.00 (s), 120.93 (s), 119.16 (s), 36.33 (d, J=15.6 Hz).

{$^{19}$F, $^{13}$C} HMQC NMR (470 MHz, D$_{2}$O) δ −185 correlates with 99

$^{31}$P NMR (81 MHz, D$_{2}$O) δ 14.08 (d, J=67.4 Hz).

$^{19}$F NMR (470 MHz, D$_{2}$O) δ −184.91--185.35 (m).

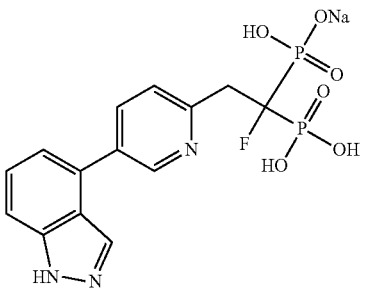

$^{1}$H NMR (500 MHz, D$_{2}$O) δ 8.46 (s, 1H), 8.04 (s, 1H), 7.91 (d, J=7.9 Hz, 1H), 7.53 (d, J=8.2 Hz, 1H), 7.46 (d, J=8.6 Hz, 1H), 7.37-7.31 (m, 1H), 7.12 (d, J=7.1 Hz, 1H), 3.58-3.47 (m, 2H).

$^{13}$C NMR (75 MHz, D$_2$O) δ 158.21-157.87 (m), 145.89 (s), 143.50 (s), 135.71 (s), 132.86 (s), 132.64 (s), 130.72 (s), 126.72 (s), 126.17 (s), 120.62 (s), 119.27 (s), 111.40 (s), 41.03 (d, J=18.1 Hz).

{$^{19}$F, $^{13}$C} HMQC NMR (470 MHz, D$_2$O) δ −186 correlates with 100

$^{31}$P NMR (81 MHz, D$_2$O) δ 13.70 (d, J=65.7 Hz).

$^{19}$F NMR (470 MHz, D$_2$O) δ −185.97 (tt, J=65.7, 25.7 Hz).

HRMS (ESI$^-$): calcd 400.02691 (C$_{14}$H$_{13}$O$_6$N$_3$FP$_2$), found (m/z) 400.02654 [M−H$^+$]$^-$

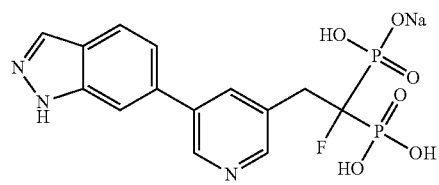

$^1$H NMR (500 MHz, D$_2$O) δ 8.43 (s, 1H), 8.39 (s, 1H), 8.12 (s, 1H), 8.09 (s, 1H), 7.44 (d, J=8.6 Hz, 1H), 7.32 (t, J=7.8 Hz, 1H), 7.13 (d, J=6.7 Hz, 1H), 3.47-3.35 (m, 2H).

$^{13}$C NMR (75 MHz, D$_2$O) δ 150.08 (s), 144.59 (s), 141.53 (s), 139.33 (s), 135.19 (m), 134.03 (s), 133.14 (s), 130.99 (s), 126.88 (s), 120.55 (s), 120.07 (s), 110.63 (s), 99.50 (dt, J=178.6, 136.1 Hz), 36.61 (d, J=18.5 Hz).

{$^{19}$F, $^{13}$C} HMQC NMR (470 MHz, D$_2$O) δ −185 correlates with 99

$^{31}$P NMR (81 MHz, D$_2$O) δ 12.47 (d, J=66.9 Hz).

$^{19}$F NMR (470 MHz, D$_2$O) δ −184.92−−185.37 (m).

HRMS (ESI$^-$): calcd 400.02691 (C$_{14}$H$_{13}$O$_6$N$_3$FP$_2$), found (m/z) 400.02648 [M−H$^+$]$^-$ $^1$H NMR (500 MHz, D$_2$O) δ 8.46 (d, J=2.4 Hz, 1H), 8.00 (s, 1H), 7.89 (s, 1H), 7.81 (dd, J=8.2, 2.4 Hz, 1H), 7.54 (dd, J=24.0, 9.2 Hz, 2H), 7.46 (d, J=8.3 Hz, 1H), 3.51-3.39 (m, 2H).

$^{13}$C NMR (126 MHz, D$_2$O) δ 157.25-156.88 (m), 144.97 (s), 143.55 (s), 134.61 (s), 134.39 (s), 134.15 (s), 129.19 (s), 126.71 (s), 125.01 (s), 123.28 (s), 118.63 (s), 112.70 (s), 40.89 (d, J=17.5 Hz).

{$^{19}$F, $^{13}$C} HMQC NMR (470 MHz, D$_2$O) δ −186 correlates with 100

$^{31}$P NMR (81 MHz, D$_2$O) δ 13.69 (d, J=65.8 Hz).

$^{19}$F NMR (470 MHz, D$_2$O) δ −185.96 (tt, J=66.6, 26.2 Hz).

HRMS (ESI$^-$): calcd 400.02691 (C$_{14}$H$_{13}$O$_6$N$_3$FP$_2$), found (m/z) 400.02683 [M−H$^+$]$^-$ HRMS (ESI$^-$): calcd 400.02691 (C$_{14}$H$_{13}$O$_6$N$_3$FP$_2$), found (m/z) 400.02706 [M−H+]$^-$ Example 11

Synthesis of (((3-cyano-6-(thiophen-2-yl)pyridin-2-yl)amino)methylene)diphosphonic acid

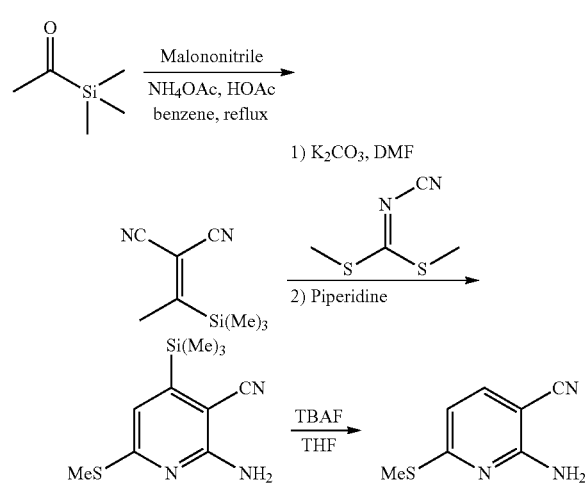

To a mixture of acetyltrimethylsilane (1.0 g, 8.6 mmol), malononitrile (625 mg, 9.46 mmol) and ammonium acetate (126 mg, 1.64 mmol), acetic acid (394 μL, 6.88 mmol) and benzene (30 mL) were added. The reaction flask was attached to a Dean-Stark trap filled with benzene and the solution was heated to 95° C. for 3 h. The orange reaction mixture was cooled, diluted with EtOAc, washed with saturated aqueous NaHCO$_3$ and brine, dried over anhydrous MgSO$_4$, and concentrated. The residue was purified by column chromatography on silica gel (using a solvent gradient from 1% to 30% EtOAc in hexanes) to give 2-(1-(trimethylsilyl)ethylidene) malononitrile as colorless oil (1.13 g, 79.8%).

To a sample of 2-(1-(trimethylsilyl)ethylidene)malononitrile (2.5 g, 15.22 mmol), potassium carbonate (2.42 g, 17.5 mmol), dimethyl N-cyanothioiminocarbonate (2.99 g, 20.4 mmol) and DMF (30 mL) were added. The resulting reaction mixture was stirred at room temperature overnight, then piperidine (2.4 mL) was added and stirring was continued for an additional 24 h at 60° C. The mixture was diluted with EtOAc and extracted with water and brine. The organic layers were collected, dried over anhydrous MgSO$_4$, and concentrated under vacuum. The residue was purified by column chromatography on silica gel (using a solvent gradient from 1% to 30% EtOAc in hexanes) to give the 2-amino-6-(methylthio)-4-(trimethylsilyl)nicotinonitrile intermediate as yellow oil (1.92 g, 53%). Finally, the TMS protecting group was removed by treating this compound (880 mg, 3.712 mmol) with 1M TBAF (4.08 mL, 4.08 mmol) in THF (2 mL) at room temperature for 2 h. The solvent was removed under vacuum, the residue was re-dissolved at EtOAc, extracted with water, dried over anhydrous MgSO₄, concentrated, and purified by column chromatography on silica gel (using a solvent gradient from 1% to 30% EtOAc in hexanes) to give 2-amino-6-(methylthio)nicotinonitrile as light yellow powder (530 mg, 87%).

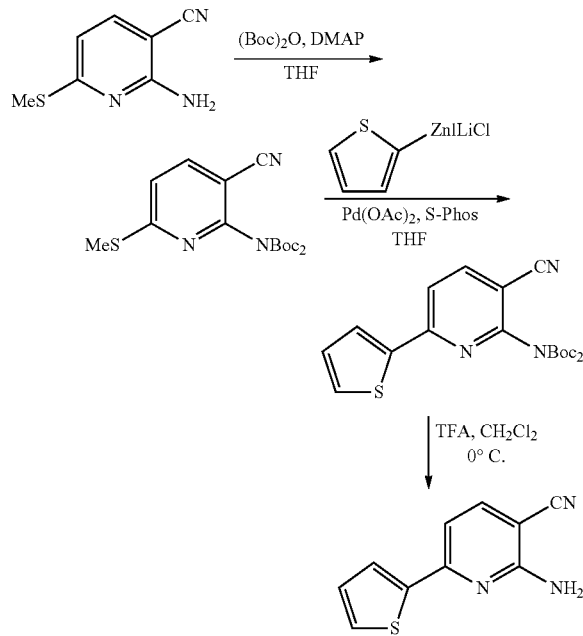

To a pressure vessel with 2-amino-6-(methylthio)nicotinonitrile (100 mg, 0.605 mmol) and DMAP (7.4 mg, 0.061 mmol) in THF (1 mL), (Boc)₂O (330 mg, 1.513 mmol) was added slowly at room temperature. After release of the gas evolved, the resulting mixture was refluxed overnight. The solvent was then removed under vacuum. The residue was dissolved in EtOAc and washed with saturated aqueous NaHCO₃ and brine. The organic layer was dried over anhydrous MgSO₄, concentrated, and purified by column chromatography on silica gel (using a solvent gradient from 1% EtOAc in hexanes to 100% EtOAc) to give bis-Boc protected amino derivative as white solid (210 mg, 94%). ¹H NMR (400 MHz, CDCl₃) δ 7.72 (d, J=8.0 Hz, 1H), 7.20 (d, J=8.0 Hz, 1H), 2.54 (s, 3H), 1.55 (s, 18H); ¹³C NMR (75 Hz, CDCl₃) δ 165.32 (C), 153.64 (C), 149.84 (C), 139.62 (CH), 120.20 (CH), 115.25 (C), 103.32 (C), 84.06 (C), 27.78 (CH₃), 13.30 (CH₃)

In a dry argon-flushed flask equipped with a septum and a magnetic stirring bar, the above intermediate (310 mg, 0.848 mmol), Pd(OAc)₂ (4.8 mg, 2.5 mol %) and S-Phos (17.4 mg, 5 mol %) were dissolved in dry THF (1 mL). After 10 min of stirring, the crude thiophenyl organo zinc reagent (404 mg, 1.27 mmol; prepared as previously described by Knochel's group; *Org. Lett.* 2009, 11, 4228-4231) was added drop wise and the reaction mixture was stirred at room temperature overnight. The reaction mixture was quenched with saturated Na₂CO₃ and extracted with EtOAc. The combined organic layers were dried over MgSO₄, concentrated by reduced pressure, and purified by silica gel (using a solvent gradient from 1% EtOAc in hexanes to 100% EtOAc) to give the desired cross-coupled product as white powder (300 mg, 88%). ¹H NMR (400 MHz, CDCl₃) δ 7.96 (d, J=8.0 Hz, 1H), 7.71 (dd, J=1.3, 4.0 Hz, 1H), 7.69 (d, J=8.0 Hz, 1H), 7.53 (dd, J=1.3, 4.0 Hz, 1H), 7.15 (dd, J=4.0, 4.0 Hz, 1H), 1.49 (s, 18H).

To a solution of the above bis-Boc protected 2-amino-6-(thiophen-2-yl)nicotinonitrile (300 mg, 0.747 mmol) in CH₂Cl₂, TFA (1.15 mL, 14.9 mmol) was added at 0° C. The mixture was stirred at room temperature for 1 h. The solution was diluted with EtOAc and extracted with saturated NaHCO₃. The organic layer was collected, dried over MgSO₄, concentrated, and purified by chromatography on silica gel (using a solvent gradient from 1% to 25% EtOAc in hexanes) to give the free amino intermediate (2-amino-6-(thiophen-2-yl)nicotinonitrile) as white solid (139 mg, 93%). ¹H NMR (400 MHz, CDCl₃) δ 7.66 (d, J=12.0 Hz, 1H), 7.62 (dd, J=1.2, 4.1 Hz, 1H), 7.45 (dd, J=1.2, 4.2 Hz, 1H), 7.11 (dd, J=4.1, 4.2 Hz, 1H), 7.07 (d, J=12.0 Hz, 1H), 5.18 (brs, 2H)

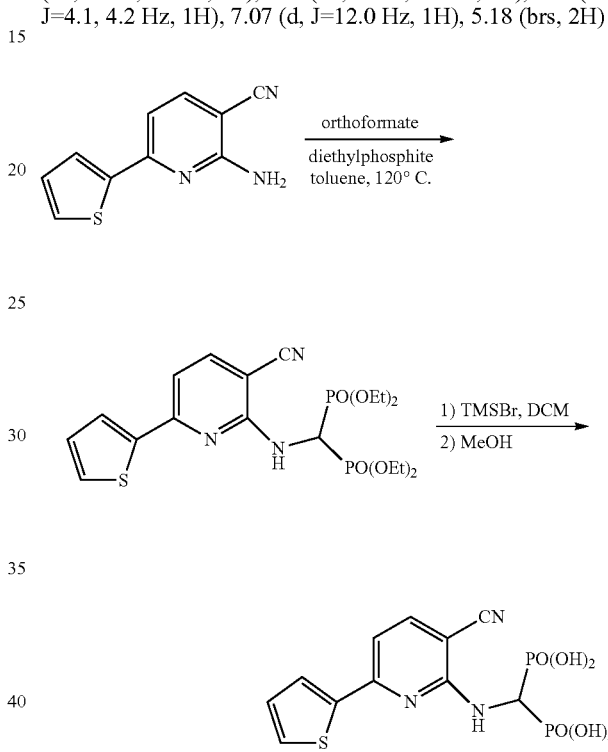

In a pressure vessel containing a toluene solution of 2-amino-6-(thiophen-2-yl)nicotinonitrile (20 mg, 0.066 mmol), triethyl orthoformate (13 μL, 0.08 mmol) and diethylphosphite (51 μL, 0.398 mmol) were added. The reaction mixture was stirred at 130° C. for 3 day. The mixture was cooled to temperature, diluted with EtOAc, extracted with saturated aqueous NaHCO₃, concentrated, and purify by column chromatography on silica gel (using a solvent gradient from 1:1 EtOAc/hexanes to 100% EtOAc and then to 20% MeOH in EtOAc) to give the bisphosphonate tetraester as yellow oil (20 mg, 62%). ¹H NMR (300 MHz, CDCl₃) δ 7.69 (d, J=6.0 Hz, 1H), 7.61 (dd, J=3, 6 Hz, 1H), 7.46 (dd, J=3, 6 Hz, 1H), 7.06-7.12 (m, 2H), 5.49-5.72 (m, 2H), 4.13-4.26 (m, 8H), 1.29 (t, J=9.0 Hz, 3H), 1.21 (t, J=9.0 Hz, 3H); ¹³C NMR (75 MHz, CDCl₃) δ 155.91 (C), 154.23 (C), 143.34 (C), 143.12 (CH), 129.94 (CH), 128.41 (CH), 126.94 (CH), 116.17 (C), 108.58 (CH), 90.20 (CH), 163.56 (CH₂), 16.30 (CH₃).

Finally, a solution of the bisphosphonate tetraester from above (45 mg, 0.092 mmol) in CH₂Cl₂ (5 mL) was cooled to 0° C. and then trimethylsilyl bromide (183 μL, 1.385 mmol) was added. The solution was stirred at room temperature for 2 days. The solvent was removed under reduced pressure and the residue was washed with MeOH (4×2 mL). The solid final

Example 18

Synthesis of (((4-(thiophen-3-yl)pyridin-2-yl)amino)methylene)diphosphonic acid

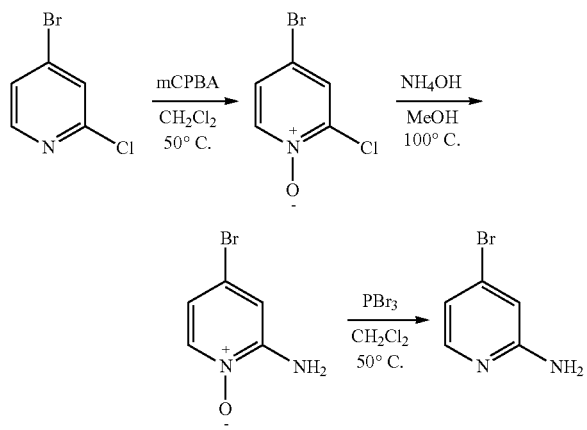

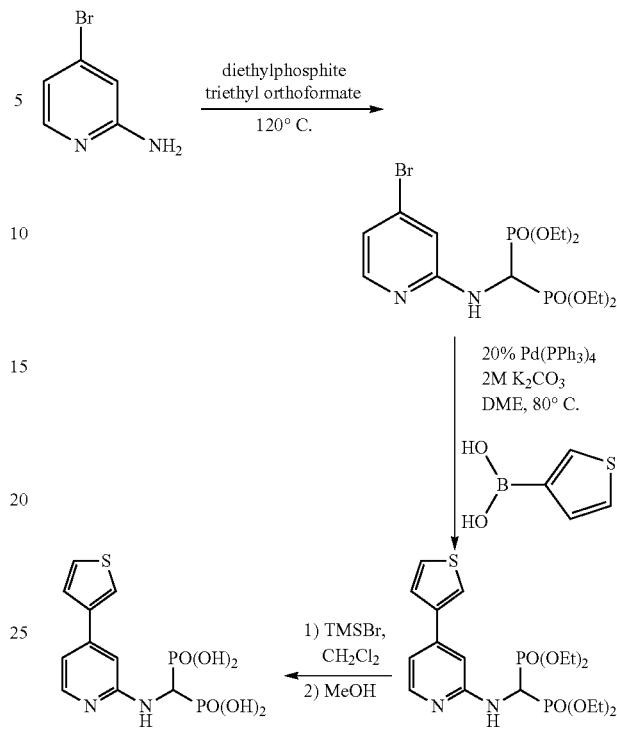

To a flask of 4-bromo-2-chloropyridine (120 μL, 1.08 mmol) in $CH_2Cl_2$ (10 mL) was added with m-chloroperbenzoic acid (932 mg, 3.78 mmol) in portions. The mixture was stirred at 50° C. overnight. The solution was cooled to room temperature, diluted with EtOAc (75 mL), and washed by saturated aqueous sodium bisulfite (50 mL) and saturated aqueous $NaHCO_3$ (50 mL). The organic layer was dried over anhydrous $MgSO_4$, concentrated, and purified by chromatography on silica gel (solvent mixture of 5/1 EtOAc/Hex) to give the N-oxide intermediate as colorless oil (200 mg, 89% yield). $^1$H NMR (300 MHz, $CDCl_3$) δ 8.17 (d, J=5.4 Hz, 1H), 7.64 (d, J=2.1 Hz, 1H), 7.32 (dd, J=5.4, 2.1 Hz, 1H)

A solution of the above N-oxide intermediate (20 mg, 0.096 mmol, in 1 mL of MeOH) was placed in a pressure vessel, excess ammonium hydroxide (~40 eq) was added and the mixture was stirred at 100° C. overnight. The solution was cooled to room temperature, diluted with EtOAc, and extracted with brine. The organic layers were collected, dried over anhydrous $MgSO_4$, concentrated, and purified by chromatography on silica gel (using a solvent gradient of 0% to 20% MeOH in EtOAc) to give the 2-amino-4-bromopyridine 1-oxide product as white solid (12 mg, 66% yield).

A solution of 2-amino-4-bromopyridine 1-oxide (45 mg, 0.24 mmol) in $CH_2Cl_2$ (1 mL) was cooled in an ice bath and $PBr_3$ (224 μL, 2.38 mmol) was added drop wise. The reaction mixture was allowed to warm-up and stir at 50° C. overnight. The solution was cooled to room temperature, diluted with $CH_2Cl_2$, and extracted with 1M NaOH and brine. The organic layer was collected, dried over anhydrous $MgSO_4$, concentrated, and purified by chromatography on silica gel (using a solvent gradient from 1% to 15% of EtOAc in hexanes) to give the final product 2-amino-4-bromopyridine as a white solid (11.6 mg, 28% yield). $^1$H NMR (300 MHz, $CDCl_3$) δ 7.88 (d, J=5.4 Hz, 1H), 6.79 (dd, J=5.4, 1.5 Hz, 1H), 6.67 (d, J=1.5 Hz, 1H).

In a pressure vessel, 2-amino-4-bromopyridine (70 mg, 0.405 mmol), triethyl orthoformate (81 μL, 0.486 mmol) and diethylphosphite (313 μL, 2.428 mmol) were dissolved in toluene (1 mL) and the mixture was stirred at 120° C. overnight. The solution was cooled to room temperature, diluted with EtOAc (50 mL), and extracted with saturated aqueous $NaHCO_3$ (50 mL). The organic layer was collected, dried over anhydrous $MgSO_4$, concentrated, and purified by column chromatography on silica gel (20/1 EtOAc/MeOH) to give the bisphosphonate tetra-ester intermediate as white solid (161 mg, 87%). $^1$H NMR (300 MHz, $CDCl_3$) δ 7.89 (d, J=6.0 Hz, 1H), 6.75-6.77 (m, 2H), 5.45 (td, J=22.2, 9.9 Hz, 1H), 5.15 (d, J=9.9 Hz, 1H), 4.08-4.25 (m, 8H), 1.21-1.28 (m, 12H); $^{13}$C NMR (75 MHz, $CDCl_3$) δ 156.89 (C), 148.21 (CH), 133.10 (C), 117.48 (CH), 112.10 (CH), 63.36 ($CH_2$), 45.07 (CH), 16.33 ($CH_3$); $^{31}$P NMR ($CDCl_3$) δ 18.59.

A sample of the 4-bromopyridinyl bisphosphonate ester (50 mg, 0.11 mmol), $Pd(PPh)_4$ (25 mg, 0.002 mmol), and 3-thiopheneboronic acid (20.9 mg, 0.164 mmol) were dissolved in DME (2 mL) and the mixture was degassed with argon. A solution of 2M potassium carbonate (136 μL) was added and the mixture was flushed with argon again. The reaction mixture was stirred at 80° C. for 4 h. The solution was filtered through Celite, the Celite was washed three times with EtOAc/MeOH (20:1), the solvent was removed under reduced pressure and the residue was purified by chromatography on silica gel (using a solvent gradient from 1:1 EtOAc/hexanes to 100% EtOAc and then to 20% MeOH in EtOAc) to give the expected Suzuki product (48 mg, 98% yield). $^1$H NMR (300 MHz, $CDCl_3$) δ 8.07 (d, J=5.4 Hz, 1H), 7.56 (d, J=1.5 Hz, 1H), 7.36-7.37 (m, 2H), 6.83 (d, J=5.4 Hz, 1H), 6.73 (s, 1H), 5.57 (td, J=22.5, 10.2 Hz, 1H), 5.05 (d, J=10.2 Hz, 1H), 4.09-4.23 (m, 8H), 1.19-1.27 (m, 12H); $^{13}$C NMR (75 MHz, $CDCl_3$) δ 156.62 (C), 147.94 (CH), 143.97 (C), 139.80 (C), 126.70 (CH), 125.73 (CH), 122.64 (CH), 122.24 (CH), 106.11 (CH), 63.42 ($CH_2$), 44.96 (CH), 16.33 ($CH_3$); $^{31}$P NMR ($CDCl_3$) δ 19.06.

A solution of the above bisphosphonate tetraester (40 mg, 0.086 mmol) in CH$_2$Cl$_2$ (5 mL) was cooled to 0° C. and trimethylsilyl bromide (171 μL, 1.297 mmol) was added. The reaction mixture was stirred at room temperature for 5 days. The mixture was diluted with MeOH (5 mL) and stirred for 2 h. The organic solvents were then removed under vacuum. The residue was re-dissolved in 0.5 mL MeOH and the final product was precipitated out of solution with the addition of CH$_2$Cl$_2$. The precipitate was collected by filtration and dried over high vacuum to give Example 18 as a white solid (29.8 mg, 98% yield). $^1$H NMR (300 MHz, D$_2$O) δ 7.77 (dd, J=3.0, 1.5 Hz, 1H), 7.71 (d, J=6.0 Hz, 1H), 7.37-7.42 (m, 2H), 6.87 (s, 1H), 6.78 (d, J=6.0 Hz, 1H), 3.85 (t, J=21.0 Hz, 1H); $^{13}$C NMR (75 MHz, D$_2$O) δ 157.77 (C), 145.04 (CH), 144.33 (C), 138.89 (CH), 127.31 (CH), 125.77 (CH), 124.34 (CH), 110.15 (CH), 105.56 (C), 51.64 (CH); $^{31}$P NMR (D$_2$O) δ 15.07.

The following compounds have been prepared in a manner similar to that described above for Example 18

Example 17

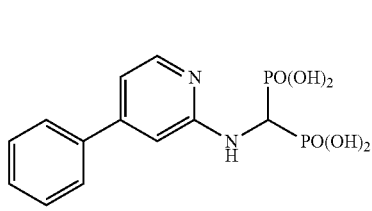

White solid; $^1$H NMR (300 MHz, D$_2$O) δ 7.77 (d, J=5.6 Hz, 1H), 7.62 (dd, J=8.4, 1.8 Hz, 1H), 7.28-7.39 (m, 3H), 6.71 (s, 1H), 6.66 (d, J=5.6 Hz, 1H), 3.79 (t, J=21.3 Hz, 1H); $^{13}$C NMR (75 MHz, D$_2$O) δ 161.79 (C), 152.30 (C), 149.69 (CH), 141.02 (CH), 131.50 (CH), 129.44 (CH), 112.32 (CH), 54.71 (CH);

$^{31}$P NMR (D$_2$O) δ 16.52;

LRMS (ESI$^-$): calcd 343.0327 (C12H14N2O6P2), found (m/z) 343.07 [M−H]$^-$

Example 19

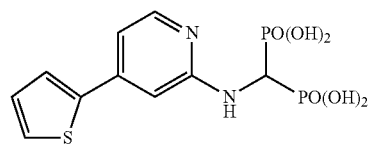

Yellow solid; $^1$H NMR (300 MHz. D$_2$O) δ 7.69 (d, J=5.4 Hz, 1H), 7.48 (d. J=3.0 Hz, 1H), 7.38 (d, J=4.5 Hz, 1H), 6.99-7.03 (m, 1H), 6.83 (s, 1H), 6.74 (d, J=4.5 Hz, 1H), 3.86 (t, J=18.9 Hz, 1H); $^{13}$C NMR (75 MHz, D$_2$O) δ 157.80 (C), 144.83 (C), 143.63 (CH), 140.68 (CH), 128.48 (CH), 127.87 (CH), 126.21 (CH), 109.42 (CH), 140.40 (C), 51.34 (CH, t, J=116 Hz); $^{31}$P NMR (D$_2$O) δ 15.12;

MS (ESI$^-$): calcd 348.9891 (C10H12N2O6P2S), found (m/z) 349.02 [M−H]$^-$

Example 20

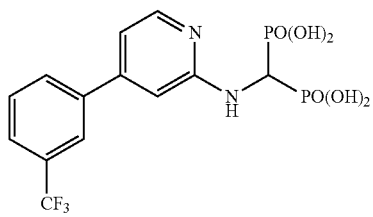

White solid (23 mg, 73%). $^1$H NMR (300 MHz, D$_2$O) δ 7.90 (s, 1H), 7.79-7.81 (m, 2H), 7.60 (d, J=8.0 Hz, 1H), 7.49 (dd, J=8.8, 8.0 Hz, 1H), 6.82 (s, 1H), 6.74 (d, J=5.7 Hz, 1H), 3.89 (t, J=19.8 Hz, 1H)

$^{31}$P NMR (D$_2$O) δ 15.41;

MS (ESI$^-$): calcd 411.0201 (C13H13F3N2O6P2), found (m/z) 411.07 [M−H]$^-$

Example 24

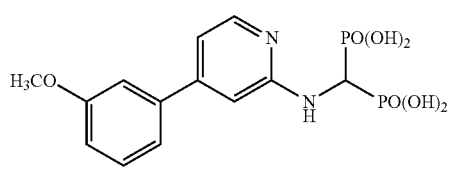

Light yellow solid; $^1$H NMR (300 MHz, D$_2$O) δ 7.77 (d, J=5.7 Hz, 1H), 7.29 (dd, J=7.6, 7.6 Hz, 1H), 7.20 (d, J=7.6 Hz, 1H), 7.15 (d, J=1.5 Hz, 1H), 6.90 (dd, J=7.6, 1.5 Hz, 1H), 6.81 (s, 1H), 6.73 (d, J=5.7 Hz, 1H), 3.91 (t, J=19.2 Hz, 1H), 3.71 (s, 3H); $^{13}$C NMR (75 MHz, D$_2$O) δ 159.2 (CH), 158.0 (C), 150.2 (CH), 145.2 (C), 139.7 (CH), 130.2 (CH), 119.8 (CH), 114.9 (CH), 112.3 (CH), 110.8 (CH), 106.5 (C), 55.3 (CH3), 51.4 (CH, t, J=122 Hz).

$^{31}$P NMR (D$_2$O) δ 15.28;

MS (ESI$^-$): calcd 373.0433 (C13H16N2O7P2), found (m/z) 373.10 [M−H]$^-$

Example 25

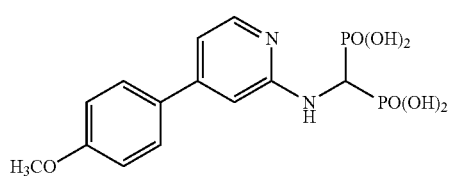

Light yellow solid; $^1$H NMR (300 MHz, D$_2$O) δ 7.71 (d, J=6.2 Hz, 1H), 7.55-7.59 (m, 2H), 6.89-6.94 (m, 2H), 6.82 (s, 1H), 6.74 (d, J=6.2 Hz, 1H), 3.85 (t, J=18.9 Hz, 1H), 3.68 (s, 3H); $^{13}$C NMR (75 MHz, D$_2$O) δ 159.90 (C), 130.19 (C), 128.35 (CH), 114.36 (CH), 110.35 (CH), 105.96 (C), 55.27 (CH3), 51.76 (CH, t, J=121.3 Hz).

$^{31}$P NMR (D$_2$O) δ 14.91;

MS (ESI$^-$): calcd 373.0433 (C13H16N2O7P2), found (m/z) 373.10 [M−H]$^-$

Example 28

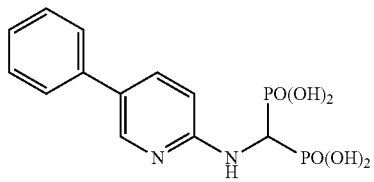

Example 28 was prepared from commercially available 2-aminopyridine, which was first brominated at C-5 (following procedures that are well known in the literature; for example, reacting with NBS) and then all the steps described for the preparation of Example 18 from the corresponding bromide at C-4.

White solid; $^1$H NMR (300 MHz, D$_2$O) δ 8.04 (s, 1H), 7.69 (d, J=8.7 Hz, 1H), 7.46 (d, J=7.6 Hz, 2H), 7.31 (dd, J=7.6, 7.6 Hz, 2H), 7.19 (dd, J=7.6, 7.6 Hz, 1H), 6.62 (d, J=8.7 Hz, 1H), 3.85 (t, J=19.2 Hz, 1H); $^{13}$C NMR (75 Hz, D$_2$O) δ157.47 (C), 143.83 (CH), 137.65 (C), 137.05 (CH), 129.04 (CH), 126.80 (CH), 125.66 (CH), 124.55 (CH), 108.35 (C), 51.29 (CH, t, J=123.75 Hz).

$^{31}$P NMR (D$_2$O) δ15.47;

MS (ESI$^-$): calcd 343.0327 (C12H14N2O6P2), found (m/z) 343.11 [M−H]$^-$

Synthesis of Common Intermediates from Scheme 4

Step 1: Synthesis of 2-bromo-3-(bromomethyl)-5-nitropyridine (Scheme 4, compound 27)

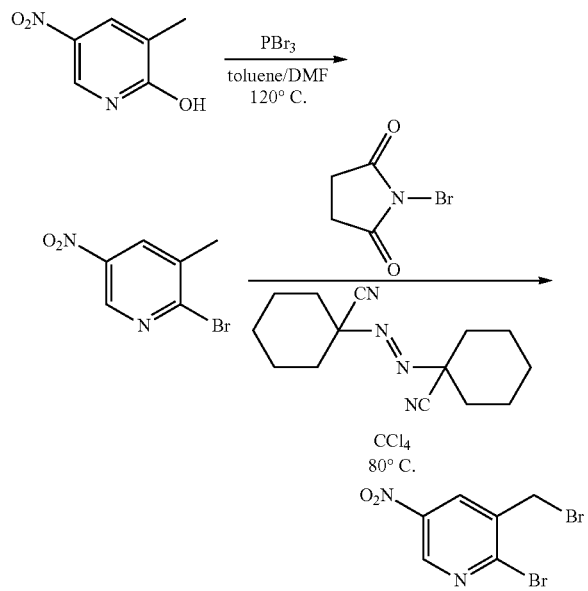

A sample of 3-methyl-5-nitropyridin-2-ol (1.44 g, 9.34 mmol) was placed in 35 mL pressure vessel and dissolved in a mixture of toluene/DMF (10:1 ratio; 15 mL). The vessel was capped with a septum, flushed with Argon and phosphorous tribromide (1.32 mL, 14.0 mmol) was added by syringe. The septum cap was replaced by a Teflon cap and the mixture was stirred for 20 min at 120° C. The mixture was cooled to room temperature, neutralized with a 3M NaOH solution and extracted with toluene (3×). The combined organic phases were dried over anhydrous MgSO$_4$ and concentrated under vacuum to give 2.00 g of the desired 2-bromo-3-methyl-5-nitropyridine product as an orange solid (99%).

$^1$H NMR (400 MHz, CDCl$_3$) δ 9.04 (d, J=2.7 Hz, 1H), 8.29 (d, J=2.5 Hz, 1H), 2.54 (s, 3H).

$^{13}$C NMR (126 MHz, CDCl$_3$) δ 150.65, 142.47, 136.76, 132.75, 22.20.

A 75 mL pressure vessel was charged with 2-bromo-3-methyl-5-nitropyridine (540 mg, 2.49 mmol), N-bromo-succinimide (452 mg, 2.54 mmol), 1,1'-azobis(cyclohexanecarbonitrile) (61 mg, 0.25 mmol) and 25 mL CCl$_4$, The vessel was closed with a rubber septum and thoroughly purged with Argon. The rubber septum was switched to a Teflon cap and the reaction mixture was stirred at 100° C. for 42 h. The mixture was cooled to RT, filtered to remove the succinimide byproduct, washed with CCl$_4$ and concentrated under vacuum. The crude residue was purified by chromatography on silica gel (using a solvent gradient from 1% to 20% EtOAc in hexanes) in order to isolate the desired product as a yellow oil (316 mg; 74% yield based on the amount of recovered starting material), along with some dibromonated byproduct (142 mg) and unreacted starting material (228 mg).

$^1$H NMR (300 MHz, CDCl$_3$) δ 9.12 (d, J=2.7 Hz, 1H), 8.55 (d, J=2.6 Hz, 1H), 4.61 (s, 2H).

$^{13}$C NMR (126 MHz, CDCl$_3$) δ 149.26, 144.42, 136.00, 133.46, 29.75.

Step 2: Synthesis of tetraethyl (2-(2-bromo-5-nitropyridin-3-yl)ethane-1,1-diyl)bis(phosphonate) and tetraethyl (2-(2-bromo-5-iodopyridin-3-yl)ethane-1,1-diyl)bis(phosphonate) (Scheme 4, compounds 30 and 31, respectively)

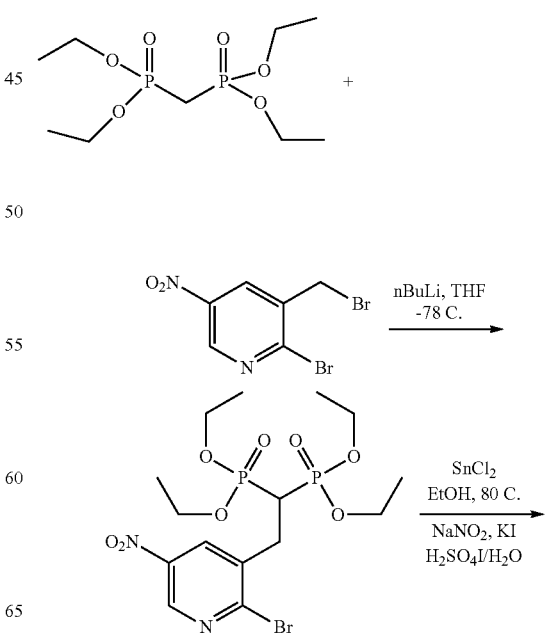

-continued

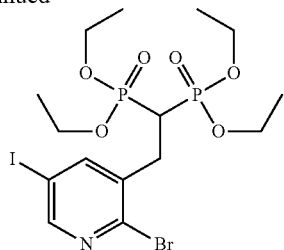

A solution of tetra-ethyl-methylene bisphosphonate ester (3.09 g, 10.73 mmol) in anhydrous THF was placed in a 250 mL RBF, under an atmosphere of argon. The solution was cooled to −78° C. and nBuLi (1.6 M in Hexanes, 7.0 mL) was added drop wise by syringe. The mixture was stirred at 0° C. for 5 min and re-cooled to −78 C. A solution of 2-bromo-3-(bromomethyl)-5-nitropyridine (3.18 g, 10.73 mmol) in 10 mL anhydrous THF was added drop wise by syringe and the reaction was stirred at −78° C. for an additional 4 h. The reaction was quenched with MeOH, concentrated under vacuum and purified by chromatography on silica gel (using a solvent gradient of 1% EtOAc in hexanes to 100% EtOAc and then to 10% MeOH in EtOAc) to isolated the desired bisphosphonate intermediate as a brown oil (2.3 g; 52% yield based on recovered starting material). $^1$H NMR (300 MHz, CDCl$_3$) δ 9.05 (d, J=2.7 Hz, 1H), 8.45 (d, J=2.7 Hz, 1H), 4.22-4.06 (m, 8H), 3.43 (ddd, J=15.4, 13.5, 7.7 Hz, 2H), 3.02 (tt, J=22.9, 7.6 Hz, 1H), 1.38-1.17 (m, 12H). $^{13}$C NMR (126 MHz, CDCl$_3$) δ 149.62 (s), 143.28 (s), 143.13 (s), 137.15 (t, J=9.2 Hz), 134.94 (s), 62.93 (dd, J=41.9, 6.7 Hz), 35.91 (t, J=133.2 Hz), 31.84 (s), 16.30 (d, J=6.2 Hz). $^{31}$P NMR (81 MHz, CDCl$_3$) δ 18.99.

MS (ESI$^+$): calcd 503.0348 and 505.0327, found 503.0 and 505.0[M+H]$^+$; calcd 525.0167 and 527.0147 found 525.0 & 527.0[M+Na]$^+$ A solution of tetraethyl (2-(2-bromo-5-nitropyridin-3-yl)ethane-1,1-diyl)bis(phosphonate) (1.08 g, 2.14 mmol) in EtOH (30 mL) was placed in a pressure vessel and stannous chloride dihydrate (2.42 g, 10.7 mmol, 5 eq) was added. The reaction mixture was stirred at 80° C. for 2 h, then cooled to RT and the mixture was slowly added to a cooled solution of saturated aqueous NaHCO$_3$ (20 mL). The mixture was concentrated under vacuum to remove the EtOH and then extracted with EtOAc (4×80 mL). The EtOAc layers were combined, dried over anhydrous Na$_2$SO$_4$ and concentrated to give a yellow oil (864 mg, 85% yield). A portion of this material (618 mg) was dissolved in 5 mL 2M sulfuric acid in a 25 mL round bottom flask and cooled in an ice bath. NaNO$_2$ (99 mg, 1.44 mmol, 1.1 eq) was slowly added drop wise as a solution in 1 mL water and the mixture was stirred for 15 min. An aqueous solution of KI (325 mg, 1.96 mmol, 1.5 eq, in 1 mL H$_2$O) was added drop wise and the mixture was stirred for 40 min at RT. The reaction was quenched with the addition of 0.3 M sodium thiosulfate (13 mL, 3 eq), followed by the addition of EtOAc and the pH was carefully adjusted to 8 with aqueous 1M NaOH. The mixture was extracted EtOAc (3×100 mL), dried over anhydrous Na$_2$SO$_4$, concentrated under vacuum and purified by column chromatography on silica gel (pre-washed with a dilute solution of NEt$_3$ in hexanes/EtOAc (9:1) and using a solvent gradient from 10% EtOAc in hexanes to 100% EtOAc and then to 10% MeOH in EtOAc). The desired tetraethyl (2-(2-bromo-5-iodopyridin-3-yl)ethane-1,1-diyl)bis(phosphonate) product was isolated as a yellow oil (544 mg, 60% over the two steps). $^1$H NMR (400 MHz, CDCl$_3$) δ 8.43 (d, J=2.3 Hz, 1H), 7.97 (d, J=2.2 Hz, 1H), 4.19-4.04 (m, 8H), 3.31-3.18 (m, 2H), 3.09-2.89 (m, 1H), 1.25 (tt, J=10.6, 5.3 Hz, 12H). $^{13}$C NMR (75 MHz, CDCl$_3$) δ 153.84, 148.42, 143.11, 137.44 (t, J=9.1 Hz), 127.97, 91.17, 62.67 (dd, J=38.8, 6.8 Hz), 35.71 (t, J=133.0 Hz), 16.24 (d, J=6.6 Hz). $^{31}$P NMR (81 MHz, CDCl$_3$) δ 19.17 (s). MS (ESI$^+$): calcd 605.93 & 607.93 found 605.9 & 607.9 [M+Na]+

Example 32

Synthesis of (2-(5-(1H-indazol-5-yl)-2-(thiophen-3-yl)pyridin-3-yl)ethane-1,1-diyl)diphosphonic acid Example 32 was synthesized from the common intermediate 31 (Scheme 4):

Step 32a: Synthesis of tetraethyl (2-(2-bromo-5-(1-(tetrahydro-2H-pyran-2-yl)-1H-indazol-5-yl)pyridin-3-yl)ethane-1,1-diyl)bis(phosphonate)

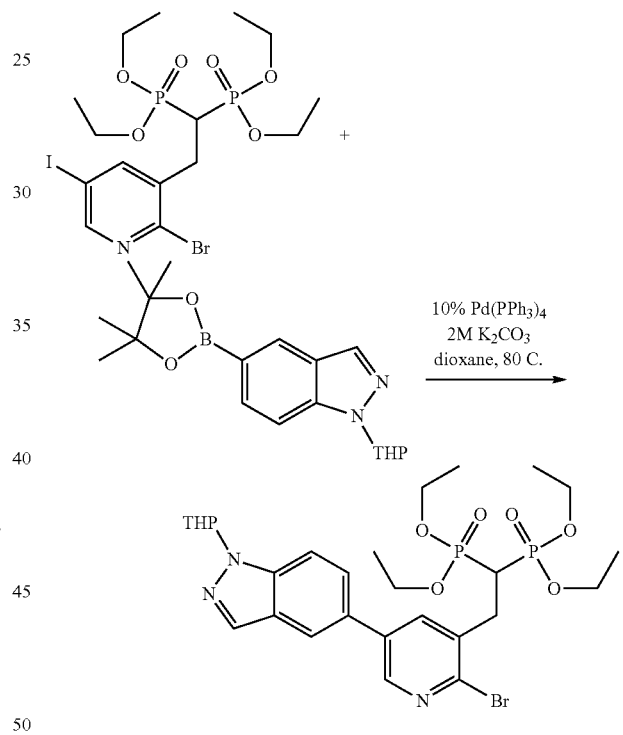

In a 5 mL vial, tetraethyl (2-(2-bromo-5-iodopyridin-3-yl)ethane-1,1-diyl)bis(phosphonate) and Pd(PPh$_3$)$_4$ were dissolved in dioxane (0.5 mL; final concentration of aryl halide dioxane at 0.1M) and the flushed with Argon. The boronate ester (1-(tetrahydro-2H-pyran-2-yl)-5-(4,4,5,5-tetramethyl-1,3,2-dioxaborolan-2-yl)-1H-indazole) was added by syringe (1M solution in dioxane, 0.10 mL, 1.1 eq) and the reaction mixture was flushed again with argon. An aqueous solution of K$_2$CO$_3$ (2.5 mL, 2M, 2.5 eq) was added by syringe and mixture was flushed with Argon. The reaction mixture was heated at 80° C. for 15 h, then cooled to room temperature, diluted with EtOAc and filtered through celite (celite was rinsed 3× with EtOAc/MeOH 1:1). The crude product was purified by chromatography on silica gel (pre-washed with a dilute solution of NEt$_3$ in hexanes/EtOAc (19:1) and using a solvent gradient from 5% EtOAc in hexanes to 100% EtOAc and then to 5% MeOH in EtOAc. The desired product was isolated as yellow oil (30 mg, 89% based on recovered starting material).

$^1$H NMR (400 MHz, CDCl$_3$) δ 8.50 (d, J=2.5 Hz, 1H), 8.10 (s, 1H), 7.98 (d, J=2.5 Hz, 1H), 7.91 (s, 1H), 7.70 (d, J=8.7 Hz, 1H), 7.59 (dd, J=8.7, 1.6 Hz, 1H), 5.76 (dd, J=9.3, 2.6 Hz, 1H), 4.22-4.00 (m, 8H), 3.77 (s, 1H), 3.47-3.34 (m, 2H), 3.24-3.07 (m, 1H), 2.15 (d, J=15.1 Hz, 3H), 1.73 (d, J=29.6 Hz, 4H), 1.25 (dt, J=16.2, 7.1 Hz, 12H).

$^{13}$C NMR (75 MHz, CDCl$_3$) δ 146.37, 142.06, 139.53, 139.27, 136.00, 135.07, 134.32, 129.61, 125.81, 125.41, 119.42, 111.13, 85.49, 69.59, 67.49, 62.68 (dd, J=49.0, 7.0 Hz), 35.96 (t, J=132.7 Hz), 29.38, 25.07, 22.49, 16.68-15.87 (m).

MS (ESI$^+$): calcd 658.14 & 660.14 found: 658.1, 660.0 [M+H]$^+$; calcd 680.13 & 682.12, found 680.1 & 682.1

Step 32b: Synthesis of tetraethyl (2-(5-(1-(tetrahydro-2H-pyran-2-yl)-1H-indazol-5-yl)-2-(thiophen-3-yl)pyridin-3-yl)ethane-1,1-diyl)bis(phosphonate)

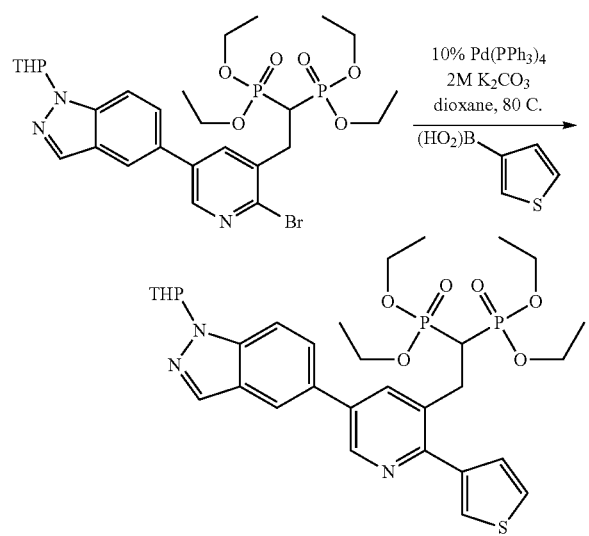

The above compound was synthesized following typical Suzuki coupling reaction conditions as previously described (Step 3)

$^1$H NMR (400 MHz, CDCl$_3$) δ 8.80 (d, J=2.1 Hz, 1H), 8.11 (s, 1H), 7.98-7.93 (m, 2H), 7.74-7.62 (m, 3H), 7.43 (d, J=2.5 Hz, 2H), 5.77 (dd, J=9.2, 2.5 Hz, 1H), 4.10-3.92 (m, 10H), 3.83-3.73 (m, 1H), 3.62-3.50 (m, 2H), 2.67-2.49 (m, 2H), 2.22-2.08 (m, 2H), 1.75 (d, J=38.6 Hz, 4H), 1.20 (q, J=7.0 Hz, 12H).

$^{13}$C NMR (75 MHz, CDCl$_3$) δ 152.44 (s), 145.93 (s), 140.79 (s), 139.19 (s), 137.70 (s), 134.90 (s), 134.33 (s), 132.30-131.38 (m), 130.79 (s), 128.47 (s), 126.03 (s), 125.77 (s), 125.44 (s), 124.63 (s), 119.26 (s), 110.95 (s), 85.46 (s), 67.49 (s), 62.45 (dd, J=35.2, 6.7 Hz), 36.22 (t, J=132.8 Hz), 29.80 (t, J=4.2 Hz), 29.40 (s), 25.09 (s), 22.53 (s), 16.23 (dd, J=6.7, 3.3 Hz).

$^{31}$P NMR (81 MHz, CDCl$_3$) δ 20.16 (s).

MS (ESI$^+$): calcd 662.22, found 662.3 [M+H]$^+$; calcd 684.20 found 684.3 [M+Na]$^+$ Step 32c Finally, a number of different protocols can be used to remove the tetrahydropyranyl (THP-) protecting group and cleave the bisphosphonate ethyl esters in order to obtain the final inhibitor, Example 32.

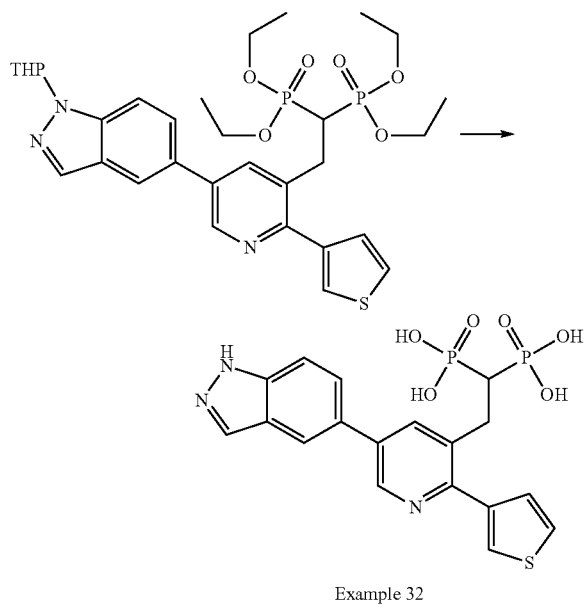

Example 32

(a) The precursor THP-protected bisphosphonate ester was transferred to a pressure vessel, dissolved in 6M HCl, the vessel was tightly sealed and the mixture stirred at 100° C. for 12 h. The reaction mixture was cooled to room temperature and concentrated to dryness under vacuum. The product was passed through a reversed phase column (solvent gradient from 1% formic acid to 1% ammonium formate pH=8) and lyophilized to give the tetra-ammonium salt.

(b) An alternative method can be used that allows the selective removal of the THP protecting group, without affecting the bisphosphonate ethyl esters: A 5 mL vial was charged with the THP protected compound (0.15 mmol) and dissolved in dry EtOH. Ethanolic HCl (0.38 ml, 0.38 mmol, 2.5 eq) was added by syringe for a final concentration of 0.1M HCl. The reaction mixture was stirred at 80° C. for 12 h. The mixture was concentrated under vacuum, re-dissolved in 100 mL EtOAc and washed with 10 mL saturated NaHCO$_3$ and 10 mL brine, dried over anhydrous Na$_2$SO$_4$, filtered and purified by column chromatography on silica gel (pre-washed with a dilute solution of NEt$_3$ in EtOAc; solvent gradient from 25% EtOAc in hexanes to 100% EtOAc and then to 20% MeOH in EtOAc) to isolate the pure tetraester product.

Finally, the bisphosphonate ethyl esters were deprotected using the following protocol: A 15 mL Teflon lined screw cap vial was charged with the tetra-ethyl bisphosphonate compound (0.132 mmol), dissolved in 5 ml distilled CH$_2$Cl$_2$ and cooled in an ice bath. Bromotrimethyl silane (0.26 mL, 1.98 mmol, 15 eq) was added by syringe and the reaction mixture was stirred at RT for 5-7 days. The reaction mixture was transferred to a 10 mL recovery flask and concentrated under vacuum. The resulting residue was treated with excess of NH$_4$OH and triturated (2×) with EtOH and diethyl ether (2×) to obtain the tetra-ammonium salt of Example 32 as a white powder (27% yield).

$^1$H NMR (500 MHz, D$_2$O) δ 8.55 (d, J=2.1 Hz, 1H), 8.29 (m, 1H), 8.15-8.10 (m, 1H), 7.78 (dd, J=8.8, 1.6 Hz, 1H), 7.73-7.70 (m, 1H), 7.65 (d, J=8.7 Hz, 1H), 7.44 (dd, J=4.9, 2.9 Hz, 1H), 7.37 (d, J=5.0 Hz, 1H), 3.28-3.17 (m, 2H), 2.32-2.18 (m, 1H).

$^{13}$C NMR (126 MHz, D$_2$O) δ 170.94, 151.16, 143.43, 139.62, 139.51, 137.11, 135.39, 134.59, 129.76, 128.98, 126.63, 125.76, 125.48, 122.95, 119.08, 110.92, 28.57.

$^{31}$P NMR (81 MHz, D$_2$O) δ 18.96.

MS (ESI$^+$): calcd 464.02, found 464.1 [M−H]$^−$

Example 35

Synthesis of (2-(2-(butylamino)-5-phenylpyridin-3-yl)ethane-1,1-diyl)diphosphonic acid Step 35a Example 35 was synthesized from the common intermediate 30 (Scheme 4) as previously described.

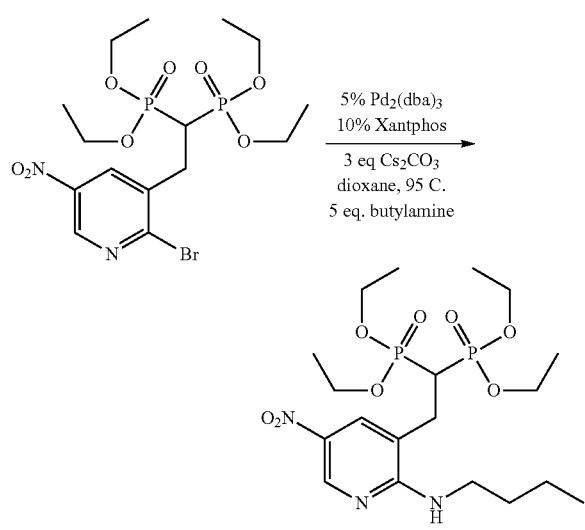

Tetraethyl (2-(2-bromo-5-nitropyridin-3-yl)ethane-1,1-diyl)bis(phosphonate) (77 mg, 0.153 mmol, 1 eq) was transferred to a 12 mL Teflon lined screw cap vial and charged with Cs$_2$CO$_3$ (150 mg, 0.46 mmol, 3 eq), Xantphos (10 mg, 0.017 mmol, 0.11 eq) and Pd$_2$(dba)$_3$ (7 mg, 0.008 mmol, 0.05 eq), capped with a rubber septum and flushed with argon. 1,4-Dioxane (1 mL) was added, the vial was flushed again with argon and the mixture was stirred for 1 min before butylamine (0.08 mL, 0.76 mmol, 5 eq) was added, and mixture flushed again. The reaction mixture was sealed with a Teflon cap and stirred at 95° C. for 16 h. The crude was cooled to room temperature, passed through a celite plug, washed with EtOAc/Acetone 1:1 and purified by column chromatography (using a solvent gradient from 5% EtOAc in hexanes to 100% EtOAc and then to 10% MeOH in EtOAc. The desired product was isolated as a yellow solid (52 mg, 69% yield).

$^1$H NMR (400 MHz, CDCl$_3$) δ 8.98 (d, J=2.7 Hz, 1H), 8.06 (d, J=2.7 Hz, 1H), 7.10 (t, J=5.1 Hz, 1H), 4.26-4.11 (m, 8H), 3.61-3.51 (m, 2H), 3.18-3.04 (m, 2H), 2.26 (tt, J=24.5, 4.5 Hz, 1H), 1.72-1.59 (m, 2H), 1.43 (dt, J=14.9, 7.4 Hz, 2H), 1.39-1.30 (m, 12H), 0.95 (t, J=7.4 Hz, 3H).

$^{13}$C NMR (75 MHz, CDCl$_3$) δ 159.04, 145.60, 134.37, 132.76, 117.14, 117.07, 63.18, 41.96, 35.06 (t, J=132.4 Hz), 31.19, 26.70, 20.28, 16.34, 16.30, 16.26, 13.82.

$^{31}$P NMR (81 MHz, CDCl$_3$) δ 21.27.

MS (ESI$^+$): calcd 518.18 found 518.15 [M+Na]$^+$

Step 35b

The final four steps in the synthesis of Example 35 were carried out following the same procedures as previously described for (i) reduction of the nitro group to the amine using SnCl$_2$ (refer to the synthesis of common intermediates from Scheme 4, step 2), followed by conversion to the bromide via the diazonium salt. The bromide intermediate was then used in a Suzuki coupling reaction (using the standard protocol previously described) to achieve cross-coupling between the bromopyridine scaffold and the phenylboronic acid reagent. Finally, the ester groups of bisphosphonate were removed using TMSBr and MeOH as previously described to give the final inhibitor, compound of Example 35.

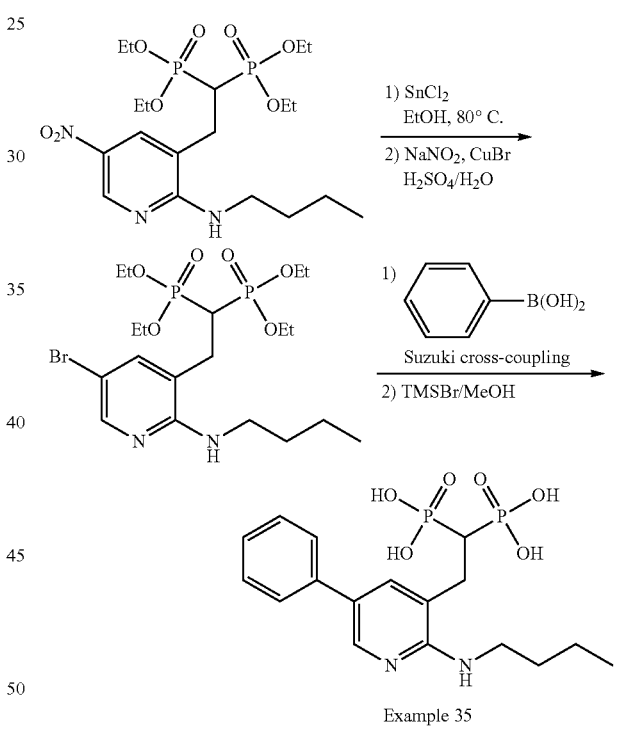

Example 35

Inhibitors of the Human Farnesyl Pyrophosphate Synthase In Vitro Enzymatic Inhibition Assay for hFPPS:

The assay is based on the literature procedure described by Marma M. S. et al. *J. Med. Chem.* 2007, 50, 5967-5975. For initial screening, the protein (enzyme) is only partly purified and the pre-incubation period of inhibitors with the enzyme is reduced to only 5 min. Consequently, the IC$_{50}$ values that we observed in our assay are different from those reported by Marma and coworkers. For example, under the conditions of our initial screening assay, the IC$_{50}$ value of risedronate is approximately 200-300 nM (Table 2) (as compared to an IC$_{50}$ value of ~6 nM that is reported by Marma and coworkers).

TABLE 2

Representative Examples of IC$_{50}$ values using Initial Screening Conditions

| Compound | Risedronate | 2 (mono-Na) | 7 (mono-Na) |
|---|---|---|---|
| IC$_{50}$ (nM) | 270 | 710 | 640 |

Compounds were also tested in a high throughput mode at a fixed concentration of 1 μM (results shown below are the average of three determinations) using a more optimized assay (e.g. a purer sample of the hFPPS protein was used and a 10 min pre-incubation period); Table 3.

TABLE 3

Representative Examples of % Inhibition of hFPPS at 1 μM of Compound

| Compound | % Inhibition at 1 μM |
|---|---|
| 12 | 35 |
| 14 | 45 |
| 17 | 85 |
| 25 | 85 |
| 26 | 65 |
| 40 | 90 |
| 42 | 95 |

The assay conducted on compounds of Examples 1 to 42 is providing IC$_{50}$ values between about nM and 100 μM.

Cell Growth Inhibition Assay:

The cell-based anti-proliferation assay is based on the literature procedure described by Zhang Y. et al. *J. Med. Chem.* 2006, 49, 5804-5814

The NCI-H460 cells (2000 cells/well; lung large cell carcinoma) are seeded in 96-well plates with various concentrations of compound (0-200 μM final concentration in the assay) in a final volume of 100 μL DMEM supplemented with 10% fetal bovine serum. Plates are incubated at 37° C. in 5% CO$_2$ atmosphere for 4 days. After 4 days, 10 μL MTT ((3-(4,5-dimethylthiazole-2-yl)-2,5-diphenyltetrazolium bromide) solution (stock 5 mg/ml) is added to each well and incubated for an additional 45 min at 37° C. and 5% CO$_2$. Media supernatant is then removed and the insoluble purple formazan dissolved in 200 μL DMSO. Quantitation is then performed by measuring the absorbance at 540 nm. All conditions are measured in three separate wells and the percent inhibition as compared to the control without an inhibitor is calculated.

Inhibition in cell proliferation was observed with both risedronate and the monosodium salt of compound 2 with approximately the same potency profile; preliminary data suggests an EC$_{50}$ of approximately 80-100 μM for both compounds.

In addition, select compounds were tested in anti-proliferation assays using multiple myeloma JJN3 cells and breast cancer MCF-7 cells. Cells were cultured with either an hFPPS inhibitor (i.e. representative Examples 1 to 42) at increasing concentrations (from 10 nM to 100 μM) or a vehicle control. Cell viability and cell cycle analysis was performed by MTT, similar to that described above; some data is shown in Table 4 and FIG. 1

TABLE 4

Representative Examples of Anti-Proliferation Effects

| Example | IC$_{50}$ in hFPPS§ (nM) | % inhibition of MM JJN3 cell proliferation* at 50 μM inhibitor | | % inhibition of breast cancer MCF-7 cell proliferation* at 50 μM inhibitor |
|---|---|---|---|---|
| | | 24 h | 48 h | 24 h |
| Risedronate | 50 | 9 | 17 | 16 |
| 2 | 120 | 37 | 19 | Not Determined |
| 36 | 180 | 15 | 26 | 25 |
| 7 | 150 | 28 | 19 | 20 |

§Conditions for the assay used in the determination of IC$_{50}$ values were more optimised than those used in the high throughput screen (all compounds were tested in parallel). The values indicated are the averages of three determinations.
*Cell viability/proliferation of these MTT cell-based assays were compared to the vehicle treated control; the values indicated are the averages of four determinations.

While the invention has been described in connection with specific embodiments thereof, it is understood that it is capable of further modifications and that this application is intended to cover any variation, use, or adaptation of the invention following, in general, the principles of the invention and including such departures from the present disclosure that come within known, or customary practice within the art to which the invention pertains and as may be applied to the essential features hereinbefore set forth, and as follows in the scope of the appended claims.

The invention claimed is:

1. A compound of formula I:

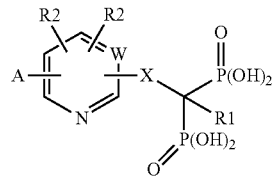

or a pharmaceutically acceptable salt thereof, wherein
A is an optionally substituted 3-11 membered heterocycle or an optionally substituted C6-10 aryl;
W is CH or N;
X is each independently CR10R11 or NR10, and wherein X is connected to a carbon atom of the ring;
R1 is H, OH, or F;
each R2 is hydrogen, or a substituent independently selected from halogen, amino, amido, cyano, hydroxyl, C1-6alkyl, C6-10aryl, C1-6alkoxy, C6-10aryloxy, 3-10 membered heterocycle, —C(O)R24, —C(O)OR24, —NR25C(O)R26 and —SO$_2$NR24R27;
R10 and R11 are each independently H or C1-6 alkyl;
R24 and R27 are each independently H, C1-6 alkyl, C6-10 aryl, C6-10aryl-C1-6alkyl or 3-10 membered heterocycle;
R25 is H or C1-6 alkyl; and
R26 is each independently H, C1-6 alkyl, C6-10 aryl, C6-10aryl-C1-6alkyl or 3-10 membered heterocycle;
or R25 and R26 are taken together with the atoms to which they are attached to form a 3 to 10 membered heterocycle.

2. The compound of claim 1, or a pharmaceutically acceptable salt thereof, wherein A is an optionally substituted monocyclic 3-6 membered heterocycle, an optionally substituted bicyclic 9-10 membered heterocycle or an optionally substituted phenyl.

3. The compound of claim 1, or a pharmaceutically acceptable salt thereof, wherein W is CH.

4. The compound of claim 1, or a pharmaceutically acceptable salt thereof, wherein R1 is H or F.

5. The compound of claim 1, or a pharmaceutically acceptable salt thereof, wherein X is each independently CR10R11 or NR10 wherein R10 and R11 are each independently H or C1-3 alkyl.

6. The compound of claim 1, or a pharmaceutically acceptable salt thereof, wherein X is each independently CH₂ or NH.

7. The compound of claim 1, or a pharmaceutically acceptable salt thereof, wherein R24 and R27 are each independently H, C1-6 alkyl, C6-10 aryl; R25 is H or C1-6 alkyl; and R26 is each independently H, C1-6 alkyl.

8. The compound of claim 1, or a pharmaceutically acceptable salt thereof, wherein R2 is hydrogen.

9. A compound of claim 1 that is

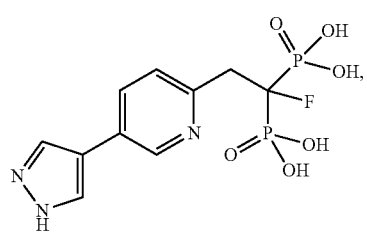

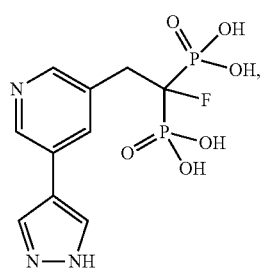

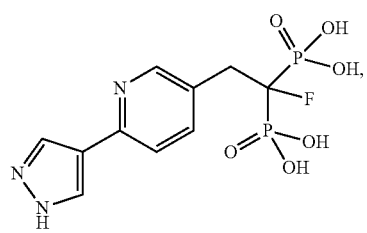

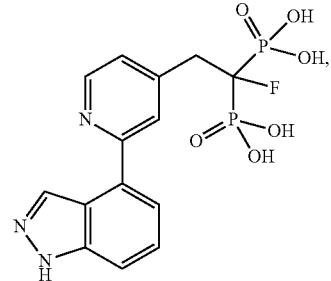

-continued

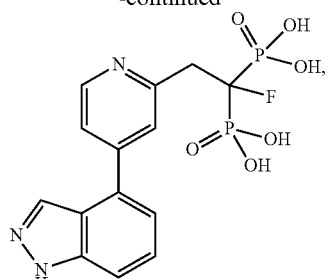

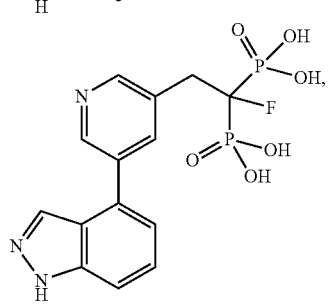

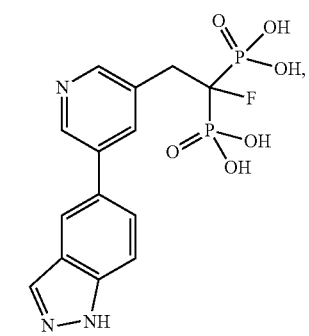

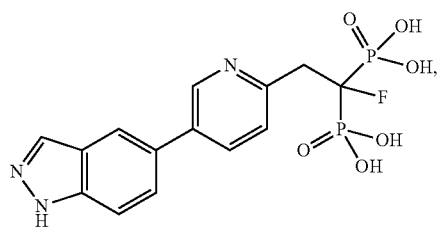

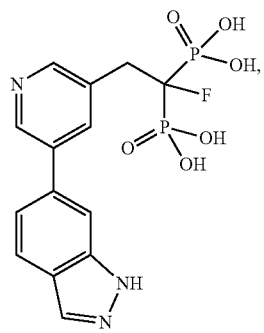

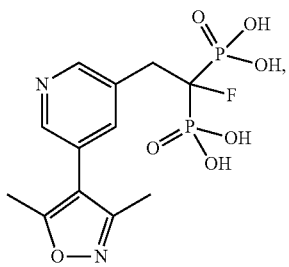

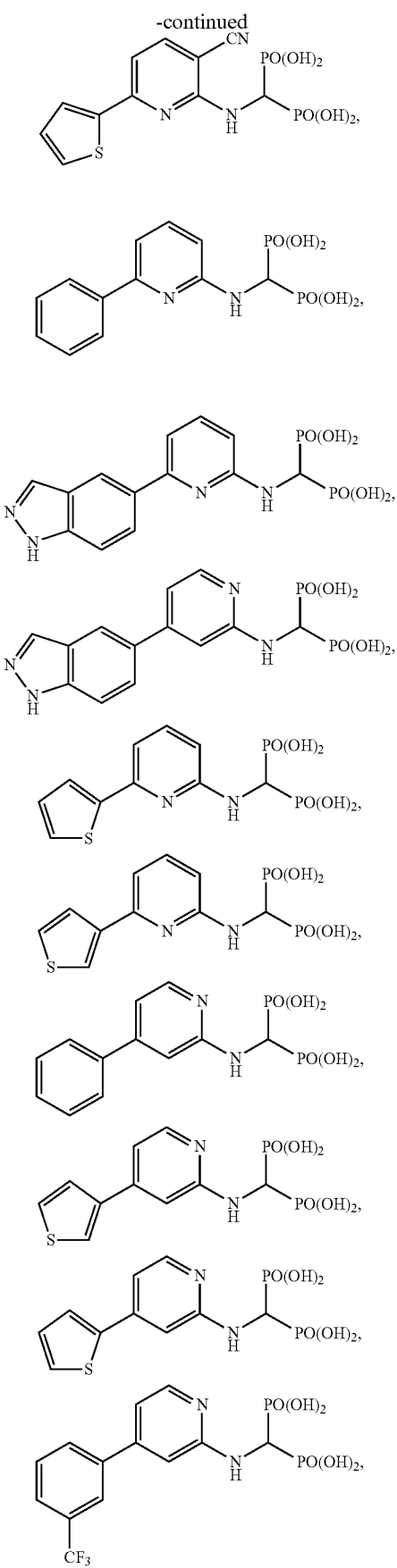
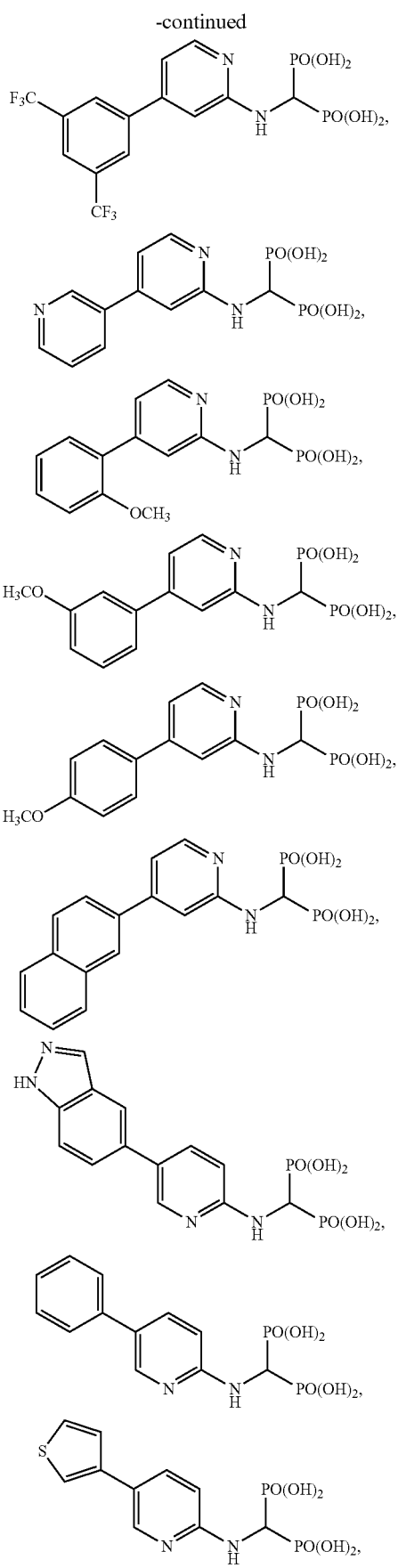

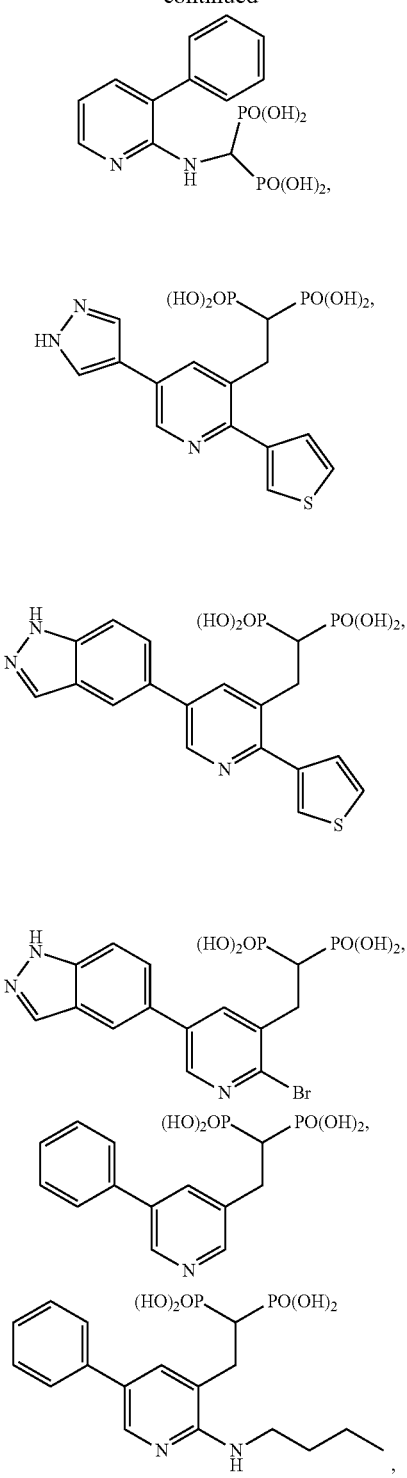

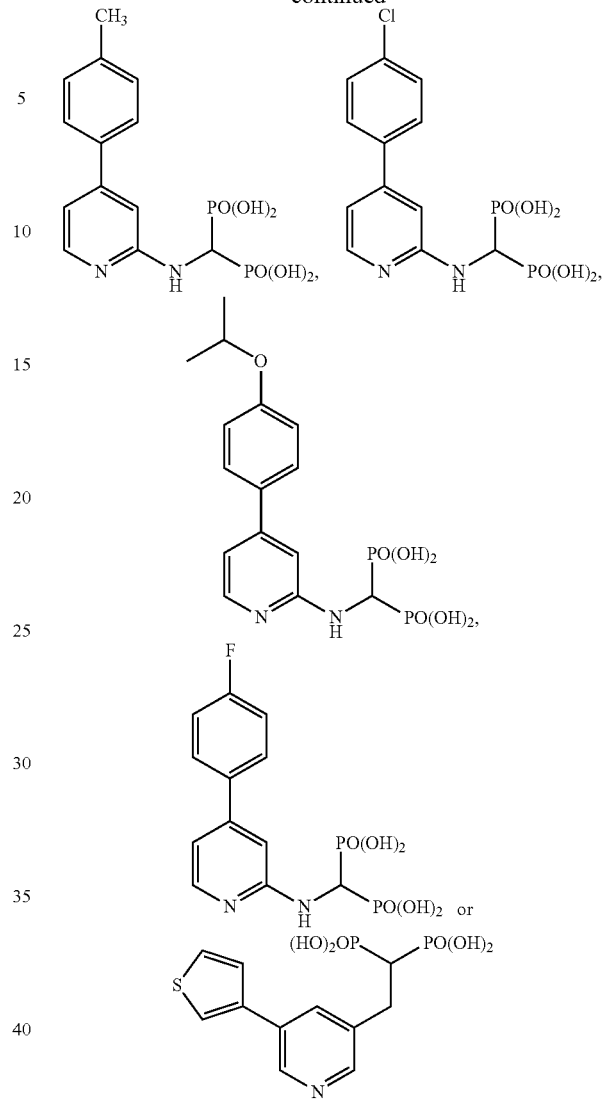

or a pharmaceutically acceptable salt thereof.

10. A pharmaceutical composition comprising a compound as defined in claim 1 or a pharmaceutically acceptable salt thereof, and an acceptable excipient.

11. The compound of claim 1, or a pharmaceutically acceptable salt thereof, wherein A is an optionally substituted phenyl.

12. The compound of claim 1, or a pharmaceutically acceptable salt thereof, wherein A is an optionally substituted 5-6 membered monocyclic heterocycle.

13. The compound of claim 1, or a pharmaceutically acceptable salt thereof, wherein A is an optionally substituted 9 to 10 membered bicyclic heterocycle.

* * * * *